United States Patent
Kühne et al.

(10) Patent No.: US 12,195,466 B2
(45) Date of Patent: Jan. 14, 2025

(54) POLYPROLINE MIMETICS OF PROLINE-DERIVED MODULE-15

(71) Applicants: Forschungsverbund Berlin e.V., Berlin (DE); Universität zu Köln, Cologne (DE)

(72) Inventors: Ronald Kühne, Berlin (DE); Hans-Günther Schmalz, Brühl (DE); Stephan Dohmen, Cologne (DE); Matthias Barone, Berlin (DE); Matthias Müller, Berlin (DE); Slim Chiha, Cologne (DE); Dominik Albat, Cologne (DE)

(73) Assignees: FORSCHUNGSVERBUND BERLIN E.V., Berlin (DE); UNIVERSITÄT ZU KÖLN, Cologne (DE)

( * ) Notice: Subject to any disclaimer, the term of this patent is extended or adjusted under 35 U.S.C. 154(b) by 1003 days.

(21) Appl. No.: 16/975,346

(22) PCT Filed: Feb. 26, 2019

(86) PCT No.: PCT/EP2019/054715
§ 371 (c)(1),
(2) Date: Jul. 15, 2021

(87) PCT Pub. No.: WO2019/162524
PCT Pub. Date: Aug. 29, 2019

(65) Prior Publication Data
US 2021/0332050 A1    Oct. 28, 2021

(30) Foreign Application Priority Data

Feb. 26, 2018 (EP) .................................... 18158650
Jun. 4, 2018 (EP) .................................... 18175731

(51) Int. Cl.
*C07D 487/04* (2006.01)
*C07D 519/00* (2006.01)

(52) U.S. Cl.
CPC ......... *C07D 487/04* (2013.01); *C07D 519/00* (2013.01)

(58) Field of Classification Search
CPC .. C07D 487/00; C07D 487/02; C07D 487/04; C07D 487/12; C07D 487/14; C07D 487/20; A61K 31/55
See application file for complete search history.

(56) References Cited

FOREIGN PATENT DOCUMENTS

WO    WO 2013/030111 A1    3/2013
WO    WO-2016092069 A1 *   6/2016    ............. A61P 35/00

OTHER PUBLICATIONS

Einsiedel (J. Org. Chem vol. 72 pp. 9102-9113 published 2007). (Year: 2007).*
English Translation of International Search Report from PCT/EP2019/054715, mailed Mar. 28, 2019.
Reuter, C., et al., 2014 "Stereoselective synthesis of proline-derived dipeptide scaffolds (ProM-3 and ProM-7) rigidified in a PPII helix conformation," *European Journal of Organic Chemistry* vol. 2014: pp. 2664-2667.

* cited by examiner

*Primary Examiner* — Clinton A Brooks
*Assistant Examiner* — George W Kosturko
(74) *Attorney, Agent, or Firm* — Knobbe Martens Olson & Bear LLP

(57) ABSTRACT

The present invention relates to chemical compounds which can be used in particular as structural mimetics of proline-rich peptides. The compounds of the present invention are capable of selectively inhibiting Ena/VASP-EVH1-mediated protein-protein interactions. The invention further relates to the use of these compounds as pharmaceutical agents and the use of the pharmaceutical agents for the treatment of tumor diseases.

20 Claims, 9 Drawing Sheets

Specification includes a Sequence Listing.

Figure 2:
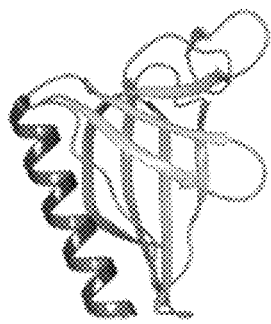

Figure 2.8:
Ena/VASP-EVH1
domain[4]

Ac-[L-2Cl-F]-[ProM-2]-[ProM-1]-OH (43)

Boc-*R,S,R*-Gly-[ProM-15]-OH       Boc-*R,S,R,S*-Phe-[ProM-15]-OH

Ac-[L-2Cl-F]-[ProM-2]-[ProM-15]-R' (115)

Boc-*R,S,R*-Gly-[ProM-15]-O*t*Bu

Boc-*S,R,S*-Gly-[ProM-15]-O*t*Bu

SEQUENCE LISTING

```
<160> NUMBER OF SEQ ID NOS: 3

<210> SEQ ID NO 1
<211> LENGTH: 5
<212> TYPE: PRT
<213> ORGANISM: Artificial Sequence
<220> FEATURE:
<223> OTHER INFORMATION: peptide

<400> SEQUENCE: 1

Phe Pro Pro Pro Pro
1               5

<210> SEQ ID NO 2
<211> LENGTH: 13
<212> TYPE: PRT
<213> ORGANISM: Artificial Sequence
<220> FEATURE:
<223> OTHER INFORMATION: peptide

<400> SEQUENCE: 2

Ser Phe Glu Phe Pro Pro Pro Pro Thr Glu Asp Glu Leu
```

```
<210> SEQ ID NO 3
<211> LENGTH: 5
<212> TYPE: PRT
<213> ORGANISM: Artificial Sequence
<220> FEATURE:
<223> OTHER INFORMATION: peptide

<400> SEQUENCE: 3

Thr Glu Asp Glu Leu
1               5
```

POLYPROLINE MIMETICS OF PROLINE-DERIVED MODULE-15

FIELD

The present invention relates to chemical compounds which can be used in particular as structural mimetics of proline-rich peptides. The compounds of the present invention are capable of selectively inhibiting Ena/VASP-EVH1-mediated protein-protein interactions. The invention further relates to the use of these compounds as pharmaceutical agents and the use of the pharmaceutical agents for the treatment of tumor diseases.

REFERENCE TO SEQUENCE LISTING

A Sequence Listing submitted as an ASCII text file via EFS-Web is hereby incorporated by reference in accordance with 35 U.S.C. § 1.52 (e). The name of the ASCII text file for the Sequence Listing is 35301990_1.TXT, the date of creation of the ASCII text file is Jul. 15, 2021, and the size of the ASCII text file is 1.06 KB.

BACKGROUND OF THE INVENTION

Interactions between proteins play a central role in almost all physiological and biochemical processes in living organisms. Proteins not only perform biocatalytic tasks (for example as enzymes) but are also involved in various biological processes. Selective inhibition of the physical interaction between peptide ligands and the corresponding protein receptors can have a significant influence on various biological mechanisms in the cell.

There is therefore a need in the prior art, particularly in the treatment of diseases, to develop molecules that inhibit specific protein-protein interactions in order to achieve biologically or medically relevant technical effects.

An example of such inhibitors are structural mimetics of diproline units. Compared to other amino acids, proline has a special role due to its chemical structure. Proline is the only secondary, proteinogenic amino acid that does not have a free NH proton to form hydrogen bonds after a peptide bond has been made. For this reason, polyproline sequences are not able to exist in the classic alpha-helix or beta-sheet secondary structures. Due to these special physical properties, polyproline amino acid sequences (e.g. proline-rich motifs (PRM)) are very well suited to form specific protein-protein interactions with receptors (e.g. proline-rich motif-binding domains (PBD)). By providing polyproline mimetics, some of these interactions can be selectively inhibited.

WO 2008/040332, WO 2013/030111 and WO 2016/092069 disclose further chemical compounds that function as diproline mimetics. For example, WO 2013/030111 discloses peptide compounds which have two adjacent diproline mimetics instead of four proline amino acids, the diproline mimetics being flanked by peptide sequences. The peptides described therein show a good affinity for a VASP-EVH1 domain, but are complex to produce on the basis of their special peptide structure. Furthermore, the peptide structures are degraded due to the peptide structure and the presence of endogenous proteases, possibly in vivo. Some of these compounds also show suboptimal cell permeability, which is definitely disadvantageous for use as a medicament. Router et al (Eur. J. Org. Chem., 2014, 13, 2664-2667) disclose a compound similar to that in WO 2008/040332, which has a bicyclic ring structure, namely a "west ring-opened" ProM-1 derivative.

Although the compounds disclosed therein can inhibit protein-protein interactions by selective binding to a receptor, there is still a need to provide further polyproline mimetics which have improved binding properties and corresponding biological effects.

DETAILED DESCRIPTION OF THE INVENTION

In light of the prior art, it was therefore the object of the invention to provide compounds which can be used as mimetics for polyproline-rich peptides, in particular as pharmaceutical agents for the treatment of various diseases. Another object of the invention was to provide novel anti-cancer drugs that are effective against the invasion and motility of cancer cells.

The problem according to the invention is solved by providing a compound according to formula I:

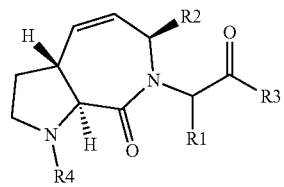

wherein

R1: H, alkyl, aryl, heteroaryl, cycloalkyl, hydroxyalkyl, arylalkyl, alkylheteroaryl, aminoalkyl, aminocarbonyl, alkylaminocarbonyl, alkylcarbonyl, mercaptoalkyl, sulfidoalkyl, preferably an R residue of an amino acid, the residues mentioned being optionally substituted, R2: alkyl, aryl, alkoxy, alkyl, cycloalkyl, mercaptoalkyl, sulfidoalkyl, arylalkyl, fluoro alkyl, the residues mentioned being optionally substituted, R3: OH, alkyl, O-alkyl, O-aryl, NRR' (R, R': H or alkyl), NROR' (R, R': H, alkyl), heteroaryl, R4: H, alkyl, acyl, aryl, heteroaryl, cycloalkyl, alkylheteroaryl, alkylcarbonyl, arylalkyl, arylcarbonyl, alkoxycarbonyl, aminocarbonyl, aryloxycarbonyl, alkylsulfonyl, arylsulfonyl, aminoacyl and/or peptidyl, or R5, the residues mentioned being optionally substituted,

R5:

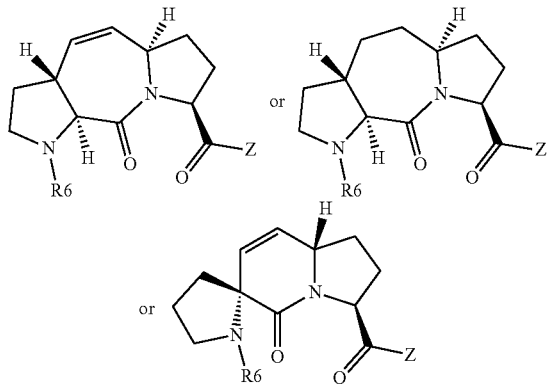

Z: bond to the structure according to formula I,
R6: H, alkyl, aryl, cycloalkyl, alkylcarbonyl, arylcarbonyl, alkoxycarbonyl, arylalkyl, aminocarbonyl, aryloxycarbonyl, alkylsulfonyl, arylsulfonyl, aminoacyl and/or peptidyl, the residues mentioned being optionally substituted, or

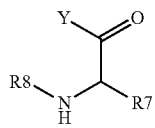

Y: bond to the structure according to R5,
R7: H, alkyl, aryl, heteroaryl, cycloalkyl, hydroxyalkyl, arylalkyl, alkylheteroaryl, aminoalkyl, aminocarbonyl, alkylaminocarbonyl, alkylcarbonyl, mercaptoalkyl, sulfidoalkyl, preferably an R residue of an amino acid, the residues mentioned being optionally substituted,
R8: H, alkyl, aryl, acyl, heteroaryl, cycloalkyl, alkylheteroaryl, alkylcarbonyl, arylalkyl, arylcarbonyl, alkoxycarbonyl, aminocarbonyl, aryloxycarbonyl, alkylsulfonyl, arylsulfonyl, aminoacyl and/or peptidyl, the residues mentioned being optionally substituted.

The compounds according to the invention have surprisingly good binding properties.

As will be shown in detail below, the invention relates to polyproline mimetics similar to WO 2008/040332, WO 2013/030111 and WO 2016/092069, but with a ring substructure "opened". The scaffolds of the present invention are designated ProM-15 in some embodiments with the previous generations are designated with different ProM numbers (e.g. ProM-1, -2 or -9), e.g.:

In a further embodiment, the invention relates to a compound according to formula II-a or formula II-b:

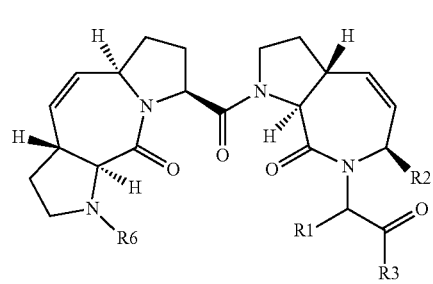

Formula II-a

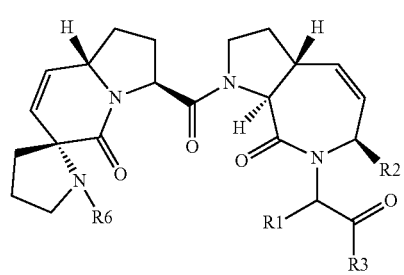

Formula II-b wherein
R1: H, alkyl, aryl, heteroaryl, cycloalkyl, hydroxyalkyl, arylalkyl, alkylheteroaryl, aminoalkyl, aminocarbonyl, alkylaminocarbonyl, alkylcarbonyl, mercaptoalkyl,

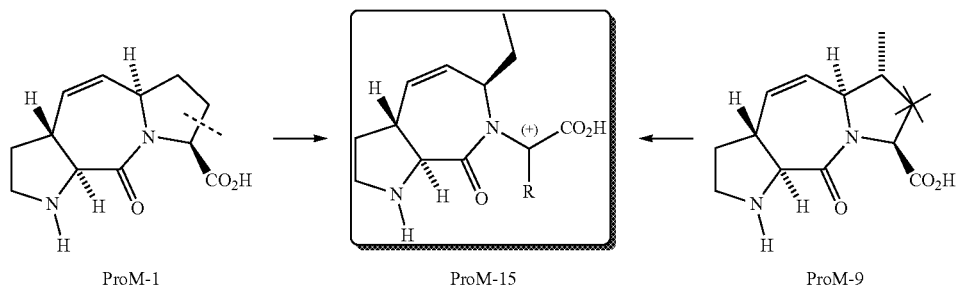

ProM-1       ProM-15       ProM-9

ProM-15 can therefore be understood to be an "east ring-opened" ProM-1 derivative or as a ProM-9 derivative reduced by one carbon atom. The structures of the formula I can be designated as "ProM-15" structures or derivatives.

On the one hand, computer modeling studies show that increased flexibility of the C-terminus of ProM-1 would represent a promising option for increasing the binding affinity to the Ena/VASP-EVH1 domain through the possible formation of hydrogen bonds. Indeed, the structures of the present invention have increased affinity for the Ena/VASP-EVH1 target.

On the other hand, ProM-15 offers the possibility of "mimicking" the methyl substituent of ProM-9 while reducing the molecular weight and thus also using the previously successfully addressed hydrophobic binding pocket. Accordingly, ProM-15 is characterized in that the positive binding properties of ProM-9 are combined with a reduction of the molecular weight and an increase in the C-terminal flexibility.

sulfidoalkyl, preferably an R residue of an amino acid, the residues mentioned being optionally substituted,
R2: alkyl, aryl, alkoxyalkyl, cycloalkyl, mercaptoalkyl, sulfidoalkyl, arylalkyl, fluoroalkyl
R3: OH, alkyl, O-alkyl, O-aryl, NRR' (R, R': H or alkyl), NROR' (R, R': H, alkyl), heteroaryl,
R6: H, alkyl, aryl, cycloalkyl, alkylcarbonyl, arylcarbonyl, alkoxycarbonyl, arylalkyl, aminocarbonyl, aryloxycarbonyl, alkylsulfonyl, arylsulfonyl, aminoacyl and/or peptidyl, the residues mentioned being optionally substituted, or

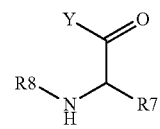

Y: bond to the structure according to formula II-a or II-b,
R7: H, alkyl, aryl, heteroaryl, cycloalkyl, hydroxyalkyl, arylalkyl, alkylheteroaryl, aminoalkyl, aminocarbonyl, alkylaminocarbonyl, alkylcarbonyl, mercaptoalkyl, sulfidoalkyl, preferably an R residue of an amino acid, the residues mentioned being optionally substituted, R8: H, alkyl, aryl, acyl, heteroaryl, cycloalkyl, alkylheteroaryl, alkylcarbonyl, arylalkyl, arylcarbonyl, alkoxycarbonyl, aminocarbonyl, aryloxycarbonyl, alkylsulfonyl, arylsulfonyl, aminoacyl and/or peptidyl, the residues mentioned being optionally substituted.

In a further embodiment, the invention relates to a compound according to formula II-c,

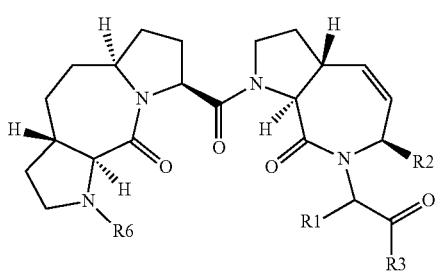

Formula II-c wherein the substituents R1-R8 are the same as above for formula II-a or II-b.

In an embodiment, the invention relates to a compound as described herein, characterized in that R7: is CH$_2$-aryl, in particular substituted-CH$_2$-phenyl, the substituent being positioned in the ortho position of the phenyl group, wherein the substituent preferably is halogen, especially Cl.

In an embodiment, the invention relates to a compound as described herein, characterized in that R6: N-acyl-(2-chlorophenyl) alaninoyl.

In some embodiments of the invention, "optionally substituted" means that one or more hydrogen atoms of the hydrocarbon group are replaced by one or more substituents selected from the group consisting of halogen (preferably fluorine, chlorine, bromine and iodine), —OH, —CN, —SH, amine (preferably —NH$_2$, —NHCH$_3$), —NO$_2$, and -alkyl, wherein alkyl is optionally substituted by one or more substituents; preferably 1, 2, 3 or 4 optional substituents are present. These embodiments of the "optional substitution" apply to all embodiments that name and/or comprise the term "optionally substituted".

In an embodiment, the invention relates to a compound as described herein, characterized in that R1: an R residue of an amino acid which is derived from a natural (canonical) or unnatural D- or L-configured amino acid.

In an embodiment, the invention relates to a compound as described herein, characterized in that R2: CH$_2$OMe, CH$_2$SMe, CH$_2$CH$_2$OR, CH$_2$CH$_2$SR (R: C1-C4 alkyl or H), benzyl, CH$_2$-benzyl, or CH$_2$CH$_2$-benzyl. R2 can also be H.

In an embodiment, the invention relates to a compound as described herein, characterized in that R2: C1-C4 alkyl, preferably methyl, ethyl, propyl, iso-propyl, butyl, iso-butyl, sec-butyl. In an embodiment, ethyl is excluded from the scope of protection as R2.

In an embodiment, the invention relates to a compound as described herein, characterized in that R2: methyl, propyl, iso-propyl, butyl, iso-butyl, sec-butyl.

In preferred embodiments of the invention R2 is iso butyl or propyl, for example in the derivatives ProM-17 (R2: Iso-butyl) or PROM-21 (R2: propyl) described herein. Corresponding substances and examples are listed below. Such compounds differ from ProM-15 at the R2 position (in ProM-15 R2: ethyl). In further preferred embodiments, in the ProM-15, ProM-17 and/or ProM-21 scaffolds R1: H, R3: OMe and R4: H or Boc (tert-butyloxycarbonyl; Boc protecting group).

In an embodiment, the invention relates to a compound as described herein, characterized in that when R3: OH, the compound is present as a salt.

In an embodiment, the invention relates to a compound as described herein, characterized in that R4, R6: can be the same or different, H, alkyl, aryl, acyl, peptidyl, alkylsulfonyl, arylsulfonyl, heteroaryl, the residues mentioned being optionally substituted.

In a further embodiment, the invention relates to a compound according to formula II-a, II-b, or II-c, characterized in that R6:

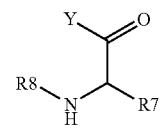

Y: bond to the structure according to formula II-a or II-b,
R7: H, alkyl, aryl, heteroaryl, cycloalkyl, hydroxyalkyl, arylalkyl, alkylheteroaryl, aminoalkyl, aminocarbonyl, alkylaminocarbonyl, alkylcarbonyl, mercaptoalkyl, sulfidoalkyl, preferably an R residue of an amino acid, the residues mentioned being optionally substituted,
R8: H, alkyl, aryl, acyl, peptidyl, alkylsulfonyl, arylsulfonyl, heteroaryl, the residues mentioned being optionally substituted.

In a further embodiment, the invention relates to a compound according to formula II-a, 1l-b, or II-c, characterized in that R6:

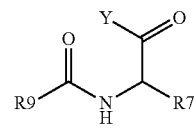

wherein
Y: bond to the structure according to formula II-a or II-b,
R7: H, alkyl, aryl, heteroaryl, cycloalkyl, hydroxyalkyl, arylalkyl, alkylheteroaryl, aminoalkyl, aminocarbonyl, alkylaminocarbonyl, alkylcarbonyl, mercaptoalkyl, sulfidoalkyl, preferably an R residue of an amino acid, the residues mentioned being optionally substituted,
R9: H, alkyl or an optionally substituted alkyl residue.

In an embodiment of the invention, the compound according to the invention, which contains ProM-15, has a structure according to formula I-a, namely:

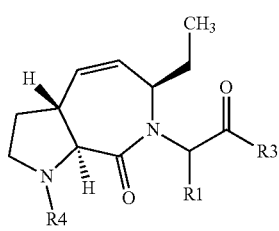

In an embodiment of the invention, the compound according to the invention, which contains ProM-17, has a structure according to formula I-b, namely:

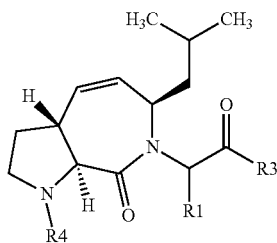

In an embodiment of the invention, the compound according to the invention, which contains ProM-21, has a structure according to formula I-c, namely:

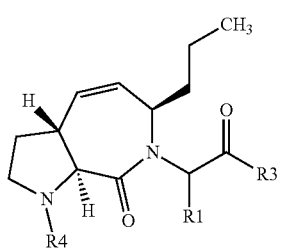

In further embodiments of the invention with structures according to formulae I-a, I-b and I-c, the definitions of groups R4, R1 and R3 apply as for embodiments with structures according to formula I, as described above.

In further embodiments of the invention, the compounds according to the invention have structures according to formulae II-a or II-b, wherein R2 is ethyl, iso-butyl or propyl, e.g., as in the derivatives ProM-15 (R2: ethyl), ProM-17 (R2: Iso-butyl) or PROM-21 (R2: propyl) described herein. These embodiments correspond to the formulae I-a, I-b and I-c.

In an embodiment, the invention relates to a compound according to formula III:

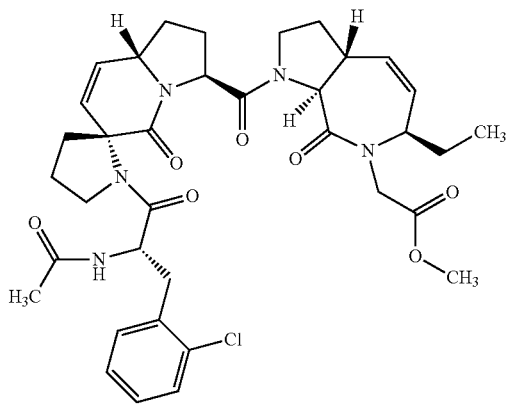 [SMILES: CC[C@@H]1C=C[C@H]2CCN(C(=O)[C@@H]3CC[C@H]4C=C[C@]5(CCCN5C(=O)[C@H](Cc5ccccc5Cl)NC(C)=O)C(=O)N43)[C@@H]2C(=O)N1CC(=O)OC]

The compound according to formula III is referred to with the systematic nomenclature used herein as "Ac-[2Cl-Phe]-[ProM-2]-[ProM-15]-OMe", where according to formula II-a or II-b R6: Ac-[2Cl-Phe] or Ac-[L-2Cl-F], R1: H, R2: ethyl, and R3: OMe. In the examples this compound is designated 247.

The invention also relates to further compounds which have the structure of the ProM-15 basic structure (e.g. formula I), and are coupled to other ProM scaffolds (ProM-1 to 10, preferably ProM-1, -2, -4, -6 and -9, or derivatives thereof). Examples of other ProM scaffolds are mentioned below. Such a coupling is preferably made by the same bond as shown in formulae II-a, -b, c- and III. Further structures according to the invention are represented by the formulae IV to VIII.

In an embodiment, the invention relates to a compound according to formula IV:

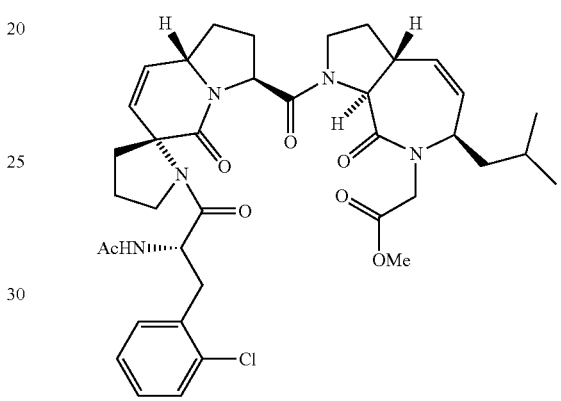

The compound according to formula IV is referred to with the systematic nomenclature used herein as "Ac-[L-2Cl-F]-[ProM-2]-[ProM-17]-OMe".

In an embodiment, the invention relates to a compound according to formula V:

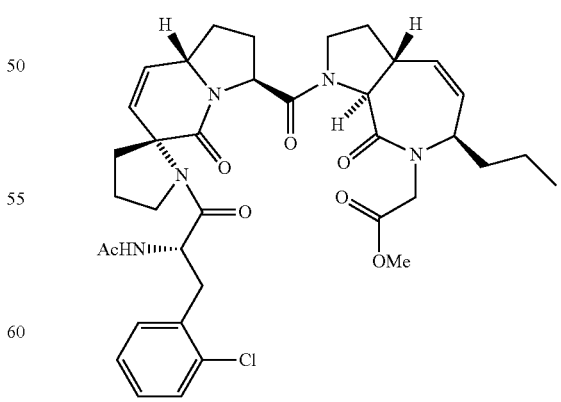

The compound according to formula V is referred to with the systematic nomenclature used herein as "Ac-[L-2Cl-F]-[ProM-2]-[ProM-21]-OMe".

In an embodiment, the invention relates to a compound according to formula VI:

[Chemical structure of formula VI]

The compound according to formula VI is referred to with the systematic nomenclature used herein as "Ac-[L-2Cl-F]-[ProM-1]-[ProM-15]-OMe".

In an embodiment, the invention relates to a compound according to formula VII:

[Chemical structure of formula VII]

The compound according to formula VII is referred to with the systematic nomenclature used herein as "Ac-[L-2Cl-F]-[ProM-1]-[ProM-17]-OMe".

In an embodiment, the invention relates to a compound according to formula VIII:

[Chemical structure of formula VIII]

The compound according to formula VIII is referred to with the systematic nomenclature used herein as "Ac-[L-2Cl-F]-[ProM-1]-[ProM-21]-OMe".

The examples of the application listed below show that the compounds according to the invention have an increased binding affinity to the Ena/VASP-EVH1 domain. This could be due to an increased flexibility of the C-terminus of ProM-1 and a possible formation of hydrogen bonds. The structures of the present invention (at least compounds according to formula III, IV, V, VI, VII, and VIII; Tables 2 and 3) have an increased affinity for the Ena/VASP-EVH1 target in comparison to the prior art (e.g. [ProM-2]-[ProM-1] as in WO 2016/092069).

The structures according to ProM-15, -17, -21 and possibly other similar configurations offer the possibility of "mimicking" the methyl substituent of ProM-9 while reducing the molecular weight and thus using the previously successfully addressed hydrophobic binding pocket. Accordingly, the structures according to the invention are characterized in that the positive binding properties of ProM-9 are combined with a reduction in the molecular weight and an increase in the C-terminal flexibility. In light of the prior art, it would not have been possible for a person of ordinary skill in the art to predict these functional improvements on the basis of the structures according to the invention.

In an embodiment, the invention relates to a compound as described herein, characterized in that it functions or is used as a ligand for an Ena/VASP-EVH1 domain.

In an embodiment, the invention relates to a compound, as described herein, which inhibits an Ena/VASP-EVH1-mediated protein-protein interaction.

In an embodiment, the compound according to the invention is characterized in that the compound has a dissociation constant ($K_d$) in the complex with an Ena/VASP-EVH1 domain of ≤ 5 μM, preferably ≤2 μM, more preferably ≤500 nM.

The invention further relates to a pharmaceutical composition comprising a compound as described herein, preferably with a pharmaceutically acceptable carrier.

The invention further relates to a compound or composition as described herein for use as a medicament for the treatment of tumor diseases. In an embodiment the tumor disease is breast cancer.

The invention further relates to a compound or composition as described herein for use as a medicament for the treatment of tumor diseases, characterized in that the compound inhibits the metastasis of a tumor.

The invention further relates to a compound or composition as described herein for use as a medicament for the treatment of tumor diseases, characterized in that the metastasis of a tumor is inhibited by inhibiting the chemotaxis and/or motility of the tumor cells based on a disruption of the actin filament synthesis.

The invention relates to compounds as a ligand for an Ena/VASP-EVH1 domain. The EVH1 domain consists of around 115 amino acids and occurs in a large number of signaling multi-domain proteins. In addition to a few others, it also includes the family of Ena/VASP proteins, which act as molecular adapters and modulate the actin dynamics of the cytoskeleton. The EVH1 domains are divided into three classes according to their ligand preference. The first class specifically recognizes in particular a [F/W/L] PPPP core motif, which is found in focal adhesion proteins such as vinculin, zyxin or RIAM, in lamellipodin, an important protein of the leading edge, in some proteins of the WAVE complex and also in the ActA protein of the intracellular bacterium *Listeria monocytogenes*. Ena/VASP proteins are also detected in filopodia and invadopodia, where they interact with formins with their EVH1 domain.

In a further aspect, the invention relates to the use of the compounds according to the invention as a ligand for a domain selected from the group comprising Src homology 3 domains, WW domains, GYF domains, UEV domains and/or profilin.

In an embodiment, the compound of the present invention is characterized in that the compound inhibits an Ena/VASP-EVH1-mediated protein-protein interaction. Accordingly, the invention also relates to the use of the new structural mimics of the polyproline II helix as surprisingly good inhibitors of protein-protein interactions, wherein EVH1 domains, SH3 domains, WW domains, GYF domains, UEV domains and profilin are involved in particular. Proteins that contain these domains, such as, e.g., VASP (EVH1 domain) or YAP (WW) play an important role in regulating cell motility (especially VASP) and cell proliferation (especially YAP), among others. For example, VASP is highly overexpressed in highly invasive breast cancer cells.

In an embodiment, the compound of the present invention is characterized in that the compound has a dissociation constant ($K_d$) in complex with an Ena/VASP-EVH1 domain of ≤20 μM, preferably ≤5 or 2 μM, more preferably $500 nM. The particularly low dissociation constants represent a surprising result. It was neither known nor mentioned in the prior art that polyproline mimetics can have such binding properties to EVH1 domains.

In a further aspect, the invention relates to a pharmaceutical composition comprising one or more compounds according to the invention, preferably with a pharmaceutically acceptable carrier. Preferred pharmaceutical carriers are, for example, fillers, extenders, binders, humectants, solution retardants, disintegrants, absorption accelerators, wetting agents, absorbents and/or lubricants.

In a preferred aspect, the invention relates to the use of the compounds mentioned as pharmaceutical agents. The use as a pharmaceutical agent relates to the use for surgical, therapeutic or diagnostic methods. In a further aspect, the invention relates to a pharmaceutical agent which comprises the compounds according to the invention optionally together with a pharmaceutically acceptable carrier.

In a preferred embodiment of the invention, the compounds are used as poly-proline mimetics. Advantageously, proline-rich amino acid sequences are found in particular in peptides which are involved in signal transduction processes, in particular intracellular signal transduction processes. For the purposes of the invention, the term mimetics can also be understood to mean analogs. The use of the compounds according to the invention is preferred for the treatment of diseases which are associated with a modification of intracellular signal transduction processes which are mediated by poly-proline helix structures, selected from the group comprising tumor diseases, bacterial infectious diseases and/or neurodegenerative diseases.

In a further aspect the invention relates to the use of the compounds according to the invention as medicaments for the treatment of tumor diseases. In a preferred embodiment of the invention, the tumor disease is breast cancer.

The use of a compound according to the invention as a medicament for treating a tumor disease is preferably characterized in that the compound inhibits the metastasis of a tumor, preferably by inhibiting the chemotaxis and/or motility of the tumor cells based on a disruption of the actin filament synthesis.

It was completely surprising that the compounds according to the invention would show a particularly good activity against the chemotaxis and/or motility of tumor cells. The inhibition of chemotaxis and/or motility of tumor cells therefore plays a role in particular in the treatment and/or prevention of tumor metastases. This represents a different technical effect compared to the inhibition of cell proliferation.

Actin is a structural protein found in all eukaryotic cells. It is part of the cytoskeleton and one of the five most common proteins in eukaryotes. Actin forms dynamic actin filaments as F-actin. These microfilaments serve the stabilization of the outer cell shape, the formation of cellular extensions, intracellular displacements and directed cellular movements. Many eukaryotic cells have a high degree of mobility, cell motility or, as also referred to, cell migration, for example to render invaders harmless in the body (cells of the immune system), to be able to heal wounds (e.g. skin cells) or to move cells in general (in development or unicellular organisms such as amoeba). Cell migration also plays an essential role in cancer metastases. This mobility is mainly based on two processes: the directed actin polymerization in the direction of movement (regulated by a number of regulators that react to signals from the cell periphery), and the actin-myosin interaction in fibril bundles (stress fibers), contractile traction ropes that run through the cell and brace form-giving elements with the base.

The disruption of the actin filament synthesis caused by the compounds according to the invention also represents a new and advantageous technical effect. By disrupting actin filament synthesis, the compounds according to the invention can inhibit the motility of cancer cells and thus strongly inhibit or prevent cancer metastasis.

The preferred tumor diseases are selected from the group comprising tumor diseases of the ear, nose and throat area, the lungs, the mediastinum, the gastrointestinal tract, the urogenital system, the gynecological system, the breast, the endocrine system, the skin, bone and soft tissue sarcomas, mesotheliomas, melanomas, neoplasms of the central nervous system, cancers or tumor diseases in childhood, lymphomas, leukemias, paraneoplastic syndromes, metastases without a known primary tumor (CUP syndrome), peritoneal carcinomatosis, immunosuppression-related malignancies and/or tumor metastases.

In particular, the tumors can be the following types of cancer: adenocarcinoma of the breast, prostate and large intestine; all forms of lung cancer originating from the bronchi; bone marrow cancer; melanoma; hepatoma; neuroblastoma; papilloma; apudoma; choristoma; branchioma;

malignant carcinoid syndrome; carcinoid heart disease; carcinoma (e.g. Walker carcinoma, basal cell carcinoma, basosquamous carcinoma, Brown-Pearce carcinoma, ductal carcinoma, Ehrlich tumor, in situ carcinoma, cancer-2 carcinoma, Merkel cell carcinoma, colloid carcinoma, non-small cell lung carcinoma, oat cell carcinoma, papillary carcinoma, scirrhous carcinoma, bronchiolo-alveolar carcinoma, bronchial carcinoma, squamous cell carcinoma and transitional cell carcinoma); histiocytic dysfunction; leukemia (e.g., related to B-cell leukemia, mixed-cell leukemia, null-cell leukemia, T-cell leukemia, chronic T-cell leukemia, HTLV-II-associated leukemia, acute lymphocytic leukemia, chronic lymphocytic leukemia, mast cell leukemia, and myeloid leukemia); malignant histiocytosis, Hodgkin's disease, non-Hodgkin's lymphoma, solitary plasma cell tumor; reticuloendotheliosis, chondroblastoma; chondroma, chondrosarcoma; fibroma; fibrosarcoma; giant cell tumors; histiocytoma; lipoma; liposarcoma; leukosarcoma; mesothelioma; myxoma; myxosarcoma; osteoma; osteosarcoma; Ewing's sarcoma; synovioma; adenofibroma; adenolymphoma; carcinosarcoma; chordoma; craniopharyngioma; dysgerminoma; hamartoma; mesenchymoma; mesonephroma; myosarcoma; ameloblastoma; cementome; odontoma; teratoma; thymoma; chorioblastoma; adenocarcinoma; adenoma; cholangioma; cholesteatoma; cylindroma; cystadenocarcinoma; cystadenoma; granulosa cell tumor; gynadroblastoma; hidradenoma; islet cell tumor; Leydig cell tumor; papilloma; Sertoli cell tumor; Theca cell tumor; leiomyoma; leiomyosarcoma; myoblastoma; myoma; myosarcoma; rhabdomyoma; rhabdomyosarcoma; ependymoma; ganglioneuroma; glioma; medulloblastoma; meningioma; neurilemmoma; neuroblastoma; neuroepithelioma; neurofibroma; neuroma; paraganglioma; non-chromaffin paraganglioma; angiokeratoma; angiolymphoid hyperplasia with eosinophilia; sclerosing angioma; angiomatosis; glomangioma; hemangioendothelioma; hemangioma; hemangiopericytoma, hemangiosarcoma; lymphangioma, lymphangiomyoma, lymphangiosarcoma; pinealoma; cystosarcoma phyllodes; hemangiosarcoma; lymphangiosarcoma; myxosarcoma; ovarian cancer; sarcoma (for example Ewing sarcoma, experimental, Kaposi sarcoma, and mast cell sarcoma); neoplasms (for example bone neoplasms, breast neoplasms, neoplasms of the digestive system, colorectal neoplasms, liver neoplasms, pancreatic neoplasms, pituitary neoplasms, testicular neoplasms, orbital neoplasms, neoplasms of the head and neck, of the central nervous system, neoplasms of the hearing organ, pelvis, respiratory tract and urogenital tract); neurofibromatosis and cervical squamous cell dysplasia.

In a further preferred embodiment, the cancer or the tumor is selected from the group: tumors of the ear, nose and throat area comprising tumors of the inner nose, paranasal sinuses, nasopharynx, lips, oral cavity, oropharynx, larynx, hypopharynx, ear, salivary glands and paragangliomas, tumors of the lung comprising non-small cell bronchial carcinoma, small cell bronchial carcinoma, tumors of the mediastinum, tumors of the gastrointestinal tract including tumors of the esophagus, stomach, pancreas, liver, gall bladder and the bile ducts, small intestine, colon and rectal carcinomas and anal carcinomas, urogenital tumors comprising tumors of the kidneys, ureters, bladder, prostate, urethra, penis and testes, gynecological tumors comprising tumors of the cervix, vagina, vulva, corpus carcinoma, malignant trophoblastic disease, ovarian cancer, tumors of the fallopian tube (tuba faloppii), tumors of the abdominal cavity, mamma carcinomas, tumors of endocrine organs comprising tumors of the thyroid gland, parathyroid gland, adrenal cortex, endocrine pancreatic tumors, carcinoid tumors and carcinoid syndrome, multiple endocrine neoplasms, bone and soft tissue sarcomas, mesotheliomas, skin tumors, melanomas comprising cutaneous and intraocular melanomas, tumors of the central nervous system, tumors in childhood comprising retinoblastoma, Wilms tumor, neurofibromatosis, neuroblastoma, Ewing's sarcoma tumor family, rhabdomyosarcoma, lymphomas comprising non-Hodgkin's lymphomas, cutaneous T-cell lymphomas, primary lymphomas of the central nervous system, Hodgkin's disease, leukemias comprising acute leukemias, chronic, myeloid and lymphatic leukemias, plasma cell neoplasms, myelodysplastic syndromes, paraneoplastic syndromes, metastases without a known primary tumor (CUP syndrome), peritoneal carcinomastosis, immunosuppression-related malignancy comprising AIDS-associated malignancies such as Kaposi's sarcoma, AIDS-associated lymphomas, AIDS-associated central nervous system lymphomas, AIDS-associated Hodgkin's disease and AIDS-associated anogenital tumors, transplant-related malignancies, metastatic tumors comprising brain metastases, lung metastases, liver metastases, bone metastases, pleural and pericardial metastases, and malignant ascites.

In a further preferred embodiment the cancer or tumor is selected from the group comprising cancerous diseases or tumor diseases of the mammary carcinomas, gastrointestinal tumors, including colon carcinomas, stomach carcinomas, pancreas carcinomas, colon cancer, small intestine cancer, ovarian carcinomas, cervical carcinomas, lung cancer, prostate cancer, renal cell carcinoma and/or liver metastases.

In the treatment of the diseases mentioned, it is particularly preferred to prepare and/or to use the pharmaceutical agent comprising the compounds according to the invention, as a gel, powders of various kind, tablet, retard tablet, premix, emulsion, infusion formulation, drops, concentrate, granulate, syrup, pellet, boluses, capsules, aerosol, spray and/or inhalant.

The pharmaceutical agent comprising the compounds according to the invention is present preferably in a concentration of 0.1 to 99.5, preferably 0.5 to 95.0, particularly preferably 20.0 to 80.0% by weight in a preparation.

This preparation is preferably applied orally, subcutaneously, intravenously, intramuscularly, intraperitoneally and/or topically.

The pharmaceutical agent containing the compounds according to the invention is preferably used in total amounts from 0.05 to 500 mg per kg, preferably from 5 to 100 mg per kg of body weight, per 24 hours.

The compound according to the invention or the pharmaceutical composition is preferably administered to the patient orally, via injection, topically, vaginally, rectally and/or nasally.

The invention also relates to a kit which comprises at least one of the compounds according to the invention and/or one of the pharmaceutical agents according to the invention, optionally with information for combining the contents of the kit—e.g., a package leaflet or an Internet address that refers to homepages with further information, etc. The information for handling the kit can comprise, for example, a therapy regimen for the diseases mentioned above, in particular for the preferred diseases. However, the information can also comprise details of how the products according to the invention are to be used in a diagnosis of the diseases mentioned. The kit according to the invention can also be used in basic research.

The invention also relates to the use of the kit for the prophylaxis and/or therapy of neurodegenerative diseases, bacterial infectious diseases or tumor diseases.

According to the invention, "alkyl" means a straight-chain or branched, open-chain, saturated hydrocarbon residue which is optionally mono- or polysubstituted. Preferred substituents are halogen atoms, alkoxy, haloalkoxy, cyano, alkylthio, haloalkylthio, amino or nitro groups, methoxy, methyl, fluoroalkyl, cyano, nitro, fluorine, chlorine, bromine or iodine are particularly preferred. "Haloalkyl", "-alkenyl" and "-alkynyl" denote alkyl, alkenyl or alkynyl substituted by identical or different halogen atoms, partially or completely, e.g. monohaloalkyl.

The term "aryl" means an optionally substituted mono-, bi- or polycyclic aromatic system with preferably 6 to 14, in particular 6 to 10 ring carbon atoms, for example phenyl, naphthyl, anthryl, phenanthrenyl and the like, preferably phenyl. The term "optionally substituted aryl" also encompasses multicyclic systems, such as tetrahydronaphthyl, indenyl, indanyl, fluorenyl, biphenylyl, the binding site being on the aromatic system. From a systematic point of view, "aryl" is generally also comprised in the term "optionally substituted phenyl".

According to the invention, the term "heteroaryl" stands for heteroaromatic compounds, i.e. completely unsaturated aromatic heterocyclic compounds, preferably for 5- to 7-membered rings with 1 to 4, preferably 1 or 2 identical or different heteroatoms, preferably O, S or N. Examples for heteroaryl are also 5- or 6-membered benzofused rings.

The term "cycloalkyl" means a carbocyclic, saturated ring system with preferably 3-8 ring carbon atoms, e.g., cyclopropyl, cyclobutyl, cyclopentyl or cyclohexyl. In the case of optionally substituted cycloalkyl, cyclic systems with substituents are comprised, with substituents with a double bond on the cycloalkyl residue, e.g. an alkylidene group such as methylidene are also comprised. In the case of optionally substituted cycloalkyl, multicyclic aliphatic systems are also comprised.

The term "alkoxy" means an alkyl residue bonded via an oxygen atom, alkenyloxy means an alkenyl residue bonded via an oxygen atom, alkynyloxy means an alkynyl residue bonded via an oxygen atom, cycloalkyloxy means a cycloalkyl residue bonded via an oxygen atom and cycloalkenyloxy means a cycloalkenyl residue bonded via an oxygen atom.

According to the invention, "hydroxyalkyl" means an alkyl group as defined above which is substituted with a hydroxy group.

According to the invention, "arylalkyl" means an aryl group as defined above which is substituted with an alkyl group.

According to the invention, "alkylheteroaryl" means an alkyl group as defined above which is substituted with a heteroaryl group.

The term "aminoalkyl" denotes an amino group which is linked via an alkyl group. Representative but not limiting examples of aminoalkyl are aminomethyl, 2-(amino) ethyl, benzyl-(methyl) aminomethyl, dimethylaminomethyl.

The term "aminocarbonyl" denotes an amino group which is linked via a carbonyl group. Representative but non-limiting examples of aminocarbonyl are diethylaminocarbonyl, benzylaminocarbonyl, ethylaminocarbonyl.

The term "alkylaminocarbonyl" denotes an aminocarbonyl group which is linked via an alkyl group. Representative but not limiting examples of aminocarbonylalkyl are 2-amino-2-oxoethyl, 2-(benzylamino)-2-oxoethyl, 2-(methylamine)-2-oxoethyl, 4-amino-4-oxobutyl, 4-(dimethylamino)-4-oxobutyl.

The term "alkylcarbonyl" denotes an alkyl group which is linked via a carbonyl group. Representative but not limiting examples of alkylcarbonyl are acetyl, 1-oxopropyl, 2,2-dimethyl-1-oxopropyl, 1-oxobutyl, 1-oxopentyl.

The term "halogen" means, for example, fluorine, chlorine, bromine or iodine. If the term is used for a residue, "halogen" means, for example, a fluorine, chlorine, bromine or iodine atom.

According to the invention, "mercaptoalkyl" means an alkyl group having a mercaptan (thiol) substituent.

According to the invention, "sulfidoalkyl" means an alkyl derivative of hydrogen sulfide ($H_2S$). Such alkyl sulfides have the structure R—S—R', where at least R or R' is alkyl. They are also known as thioethers.

According to the invention, "alkylsulfonyl" or "arylsulfonyl" means an alkyl group or aryl group containing a sulfonyl group (—$SO_2$—). This group is also known as the sulfone group. Sulfonyl compounds belong to the organic derivatives of oxygen acids of sulfur, wherein the two organic residues are bonded directly to the sulfur atom.

The term "peptidyl" means, for example, a residue formed from a peptide, e.g. by removing an $NH_2$ group from an amide group, or from part of a peptide or by several coupled amino acids, e.g. a polypeptide. The peptidyl group can therefore comprise COCHRxNHRy, where Rx is preferably an R residue of an amino acid (optionally substituted) and Ry can preferably be H, or a further peptidyl group or part thereof (optionally substituted). The peptidyl group is preferably a structure comprised by the following formula:

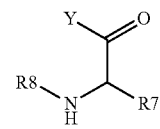

Y: bond to the adjacent structure (e.g. according to R5 of formula I),

R7: H, alkyl, aryl, heteroaryl, cycloalkyl, hydroxyalkyl, arylalkyl, alkylheteroaryl, aminoalkyl, aminocarbonyl, alkylaminocarbonyl, alkylcarbonyl, mercaptoalkyl, sulfidoalkyl, preferably an R residue of an amino acid, the residues mentioned being optionally substituted, R8: H, alkyl, aryl, acyl, heteroaryl, cycloalkyl, alkylheteroaryl, alkylcarbonyl, arylalkyl, arylcarbonyl, alkoxycarbonyl, aminocarbonyl, aryloxycarbonyl, alkylsulfonyl, arylsulfonyl, aminoacyl and/or peptidyl, the residues mentioned being optionally substituted.

In various embodiments of the invention, R residues of an amino acid are provided as possible substituents, the residues mentioned being optionally substituted. The R residues of an amino acid are preferably selected from the list set forth below. An optional substitution of the R residues is also possible, e.g. by halogen (preferably fluorine, chlorine, bromine and iodine), —OH, —CN, —SH, amine (preferably —$NH_2$, —$NHCH_3$), —$NO_2$, or -alkyl, with alkyl optionally substituted with one or more substituents; preferably wherein 1, 2, 3 or 4 optional substituents are present, preferably from the list set forth above. These embodiments of the "optional substitution" apply to all embodiments that name and/or comprise the term "optionally substituted".

| Amino acid residue | Abbr. | Code | Side chain (R residue of the amino acid) |
|---|---|---|---|
| Alanine | Ala | A | — |
| Arginine | Arg | R | —$CH_2CH_2CH_2NH$—$C(NH)NH_2$ |

| Amino acid residue | Abbr. | Code | Side chain (R residue of the amino acid) |
|---|---|---|---|
| Asparagine | Asn | N | —$CH_2CONH_2$ |
| Aspartic acid | Asp | D | —$CH_2COOH$ |
| Cysteine | Cys | C | —$CH_2SH$ |
| Glutamic acid | Glu | E | —$CH_2CH_2COOH$ |
| Glutamine | Gln | Q | —$CH_2CH_2CONH_2$ |
| Glycine | Gly | G | —H |
| Histidine | His | H | —$CH_2(C_3H_3N_2)$ |
| Isoleucine | Ile | I | —$CH(CH_3)CH_2CH_3$ |
| Leucine | Leu | L | —$CH_2CH(CH_3)_2$ |
| Lysine | Lys | K | —$CH_2CH_2CH_2CH_2NH_2$ |
| Methionine | Met | M | —$CH_2CH_2SCH_3$ |
| Phenylalanine | Phe | F | —$CH_2(C_6H_5)$ |
| Proline | Pro | P | —$CH_2CH_2CH_2$— |
| Serine | Ser | S | —$CH_2OH$ |
| Threonine | Thr | T | —$CH(OH)CH_3$ |
| Tryptophan | Trp | W | —$CH_2(C_8H_6N)$ |
| Tyrosine | Tyr | Y | —$CH_2(C_6H_4)OH$ |
| Valine | Val | V | —$CH(CH_3)_2$ |

FIGURES

Figure 1:
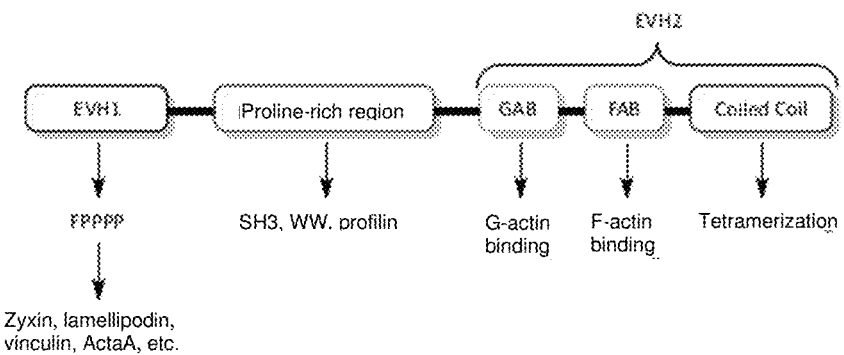

FIG. 1: Schematic structure of the Ena/VASP proteins.

FIG. 2: EVH1 domain. The EVH1 domain consists of a twisted β-sandwich structure, which is closed on one side by an a-helix.

Figure 3:
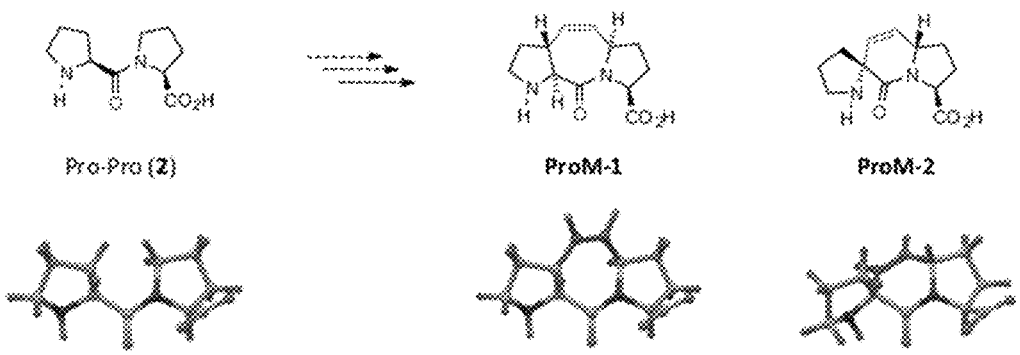

FIG. 3: Concept for the production of conformationally fixed diproline analogs in ideal PPII conformation.

Figure 4:
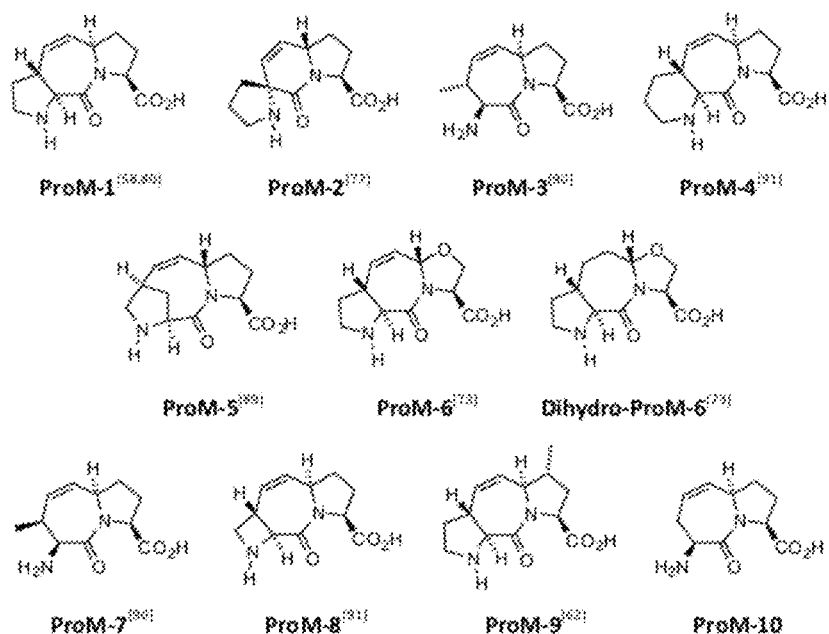

FIG. 4: Synthesized PPII secondary structure mimetics (ProMs). The publications that have appeared to date are given for all ProM building blocks shown. 58: J. Zaminer, C. Brockmann, P. Huy, R. Opitz, C. Reuter, M. Beyermann, C. Freund, M. Müller, H. Oschkinat, R. Kühne, H.-G. Schmalz, Angew. Chem. 2010, 122, 7265-7269., 80: C. Reuter, P. Huy, J.-M. Neudörfl, R. Kühne, H.-G. Schmalz, Chem. Eur. J. 2011, 17, 12037-12044, 77: C. Reuter, R. Opitz, A. Soicke, S. Dohmen, M. Barone, S. Chiha, M. T. Klein, J.-M. Neudörfl, R. Kühne, H.-G. Schmalz, Chem. Eur. J. 2015, 21, 8464-8470. 90: C. Reuter, M. Kleczka, S. d. Mazancourt, J.-M. Neudörfl, R. Kühne, H.-G. Schmalz, Eur. J. Org. Chem. 2014, 2664-2667, 91: A. Soicke, C. Reuter, M. Winter, J.-M. Neudörfl, N. Schlörer, R. Kühne, H.-G. Schmalz, Eur. J. Org. Chem. 2014, 6467-6480, 89: V. Hack, C. Reuter, R. Opitz, P. Schmieder, M. Beyermann, J.-M. Neudörfl, R. Kühne, H.-G. Schmalz, Angew. Chem. Int. Ed. 2013, 52, 9539-9543, 73: P. Huy, dissertation, University of Cologne, 2011, 62: A. Soicke, dissertation, University of Cologne, 2014.

Figure 5:
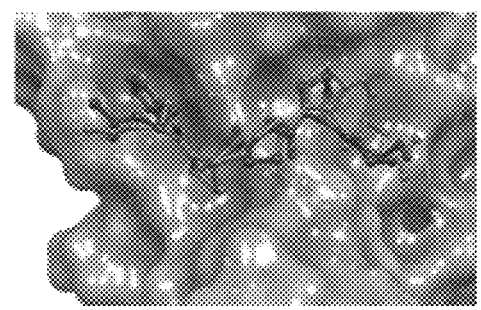

FIG. 5: Development of an Ena/VASP-EVH1 inhibitor. ($K_d$=binding constant, LE= "Ligand efficiency", Da=Dalton). Top right: FPPPP SEQ ID NO: 1) (green) of 1evh overlaid with 43 (orange) from X-ray of EnaH-EVH1 in the complex with 43.

Figure 6:
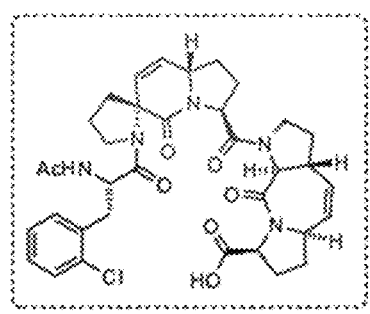

FIG. 6: Ena/VASP-EVH1 Inhibitor 43 (R. Opitz, M. Müller, C. Reuter, M. Barone, A. Soicke, Y. Roske, K. Piotukh, P. Huy, M. Beerbaum, B. Wiesner, M. Beyermann, P. Schmieder, C. Freund, R. Volkmer, H. Oschkinat, H.-G. Schmalz, R. Kühne, PNAS 2015, 112, 5011-5016).

Figure 7:
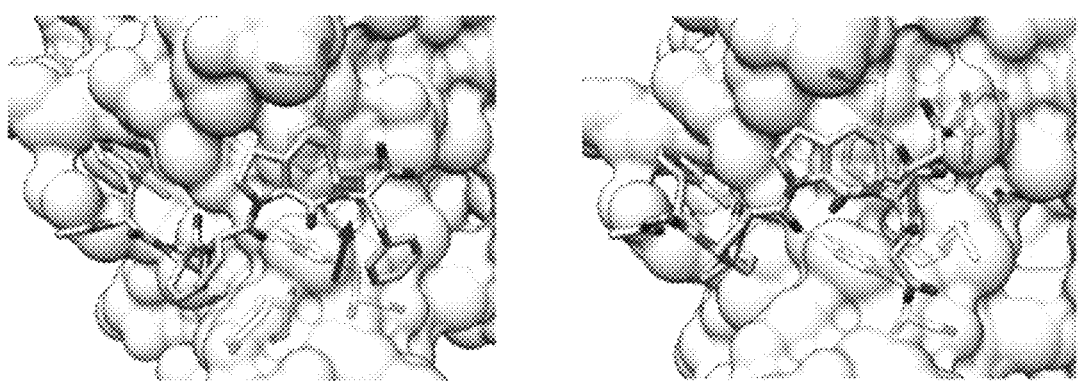

FIG. 7: Models of the ligands. Models of the ligands Ac-[L-2Cl-F]-[ProM-2]-[ProM-15 (R=Bn)]-OH (left; the red arrow points to the hydrophobic pocket also addressed by ProM-9) and Ac-[L-2Cl-F]-[ProM-2]-[ProM-15 (R=$(CH_2)_2CO_2H$)]-OH (right) on the EnaH-EVH1 domain (based on the crystal structure of Ac-[L-2Cl-F]-[ProM-2]-[ProM-1]-OH (43) with EnaH-EVH1.

Figure 8:
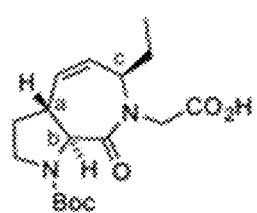
Figure 8:
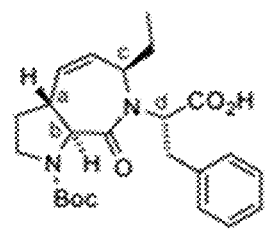

FIG. 8: The glycine and L-phenylalanine-based PPII secondary structure mimetics Boc-R,S,R-Gly-[ProM-15]-OH and Boc-R,S,R,S-Phe-[ProM-15]-OH. The letters are included to clarify the nomenclature.

Figure 9:
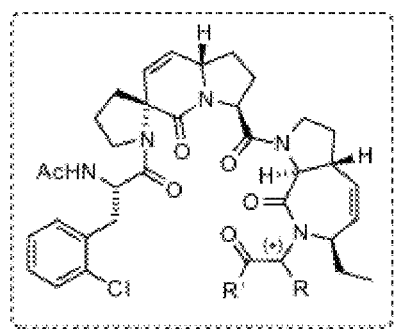

FIG. 9: Novel ProM-15-based Ena/VASP-EVH1 inhibitor 115.

Figure 10:
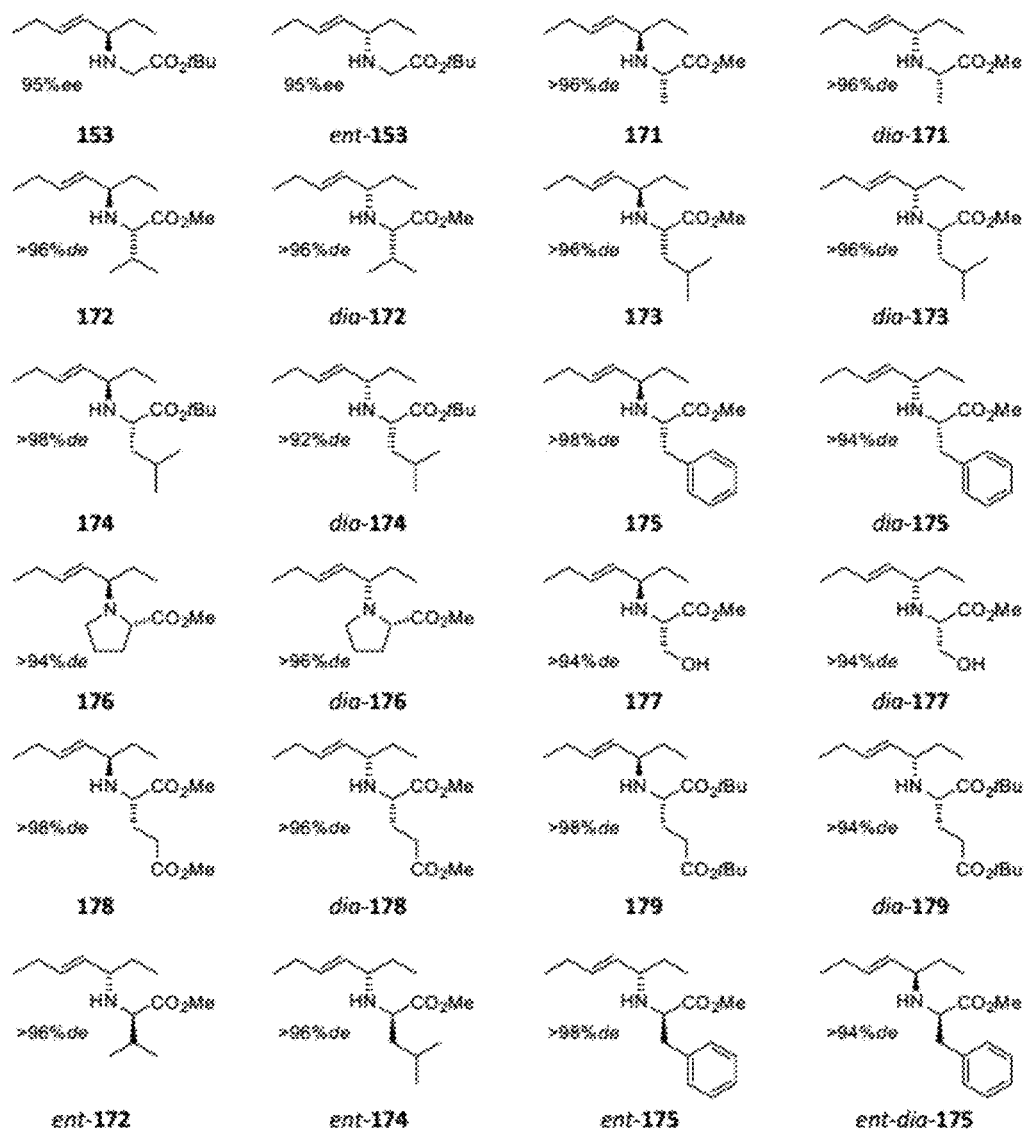

FIG. 10: Various α-amino acid ester-synthesized allylamines. The illustration shows the allylamines synthesized by Pd-catalyzed N-allylation of various α-amino acid esters and the diastereomeric excesses achieved under optimized conditions when using the chiral bisphosphine ligands 168 or ent-168 according to Scheme 4.15 (in the de values given the two diastereomers resulting from the catalysis were considered, wherein the amino acid stereocenter was defined by the choice of the corresponding N-nucleophile).

Figure 11:
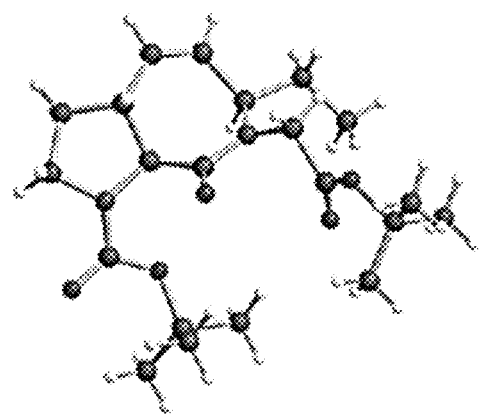
Figure 11:
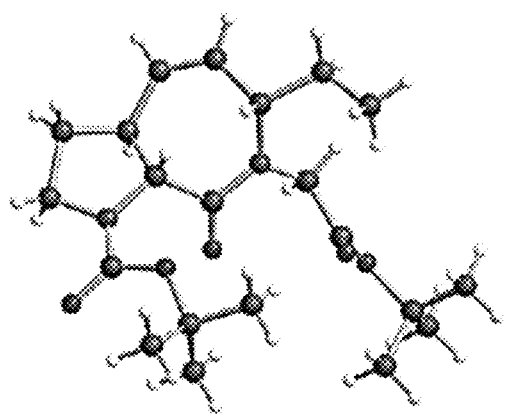
Figure 11:
Figure 11:

FIG. 11: Crystal structures of the bicyclic compounds Boc-R,S,R-Gly-[ProM-15]-OtBu and Boc-S,R,S-Gly-[ProM-15]-OtBu above the corresponding formulae.

Figure 12:
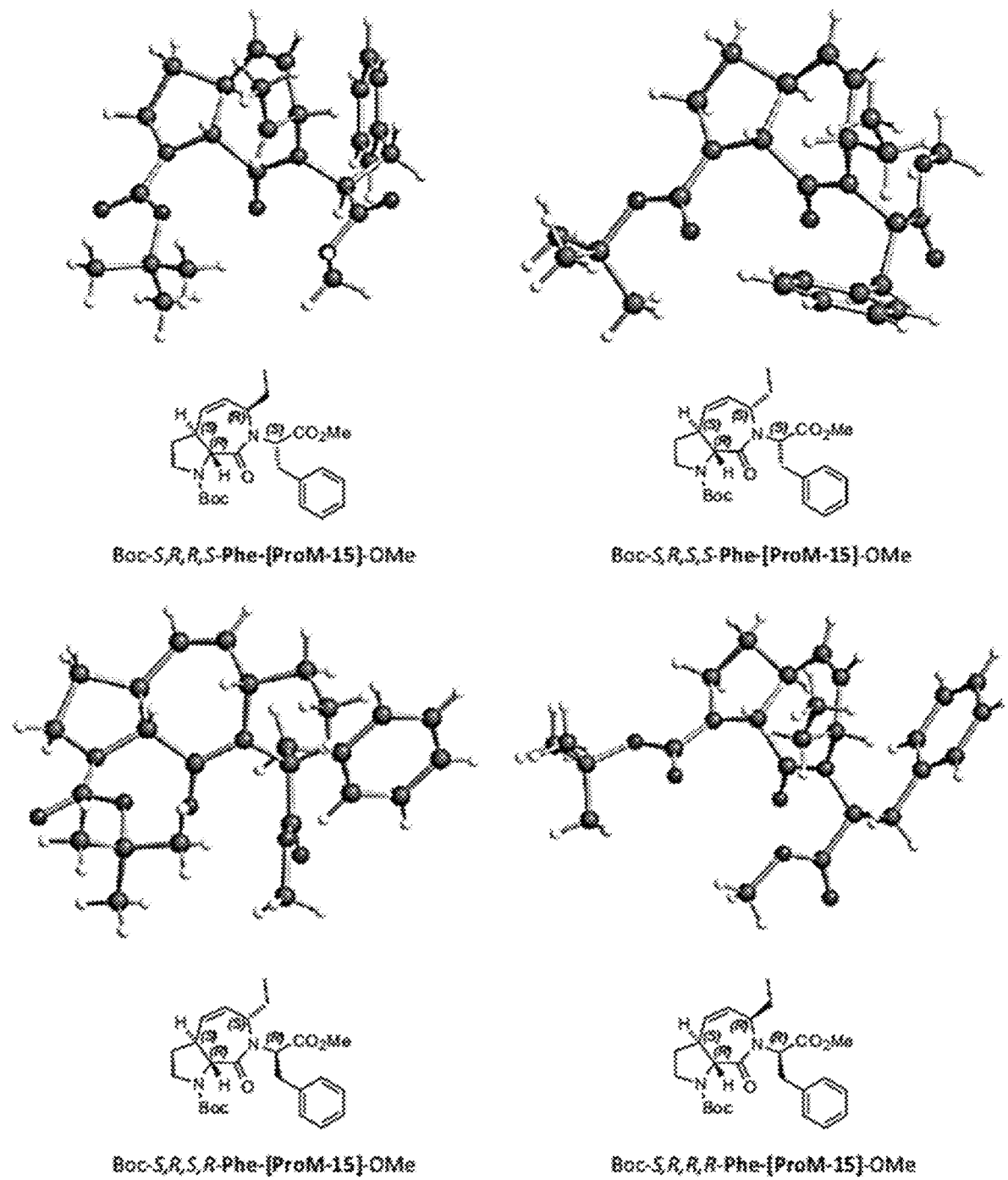

FIG. 12: Crystal structures of the diastereomeric Phe-[ProM-15] bicyclic compounds above the corresponding formulae.

Figure 13:
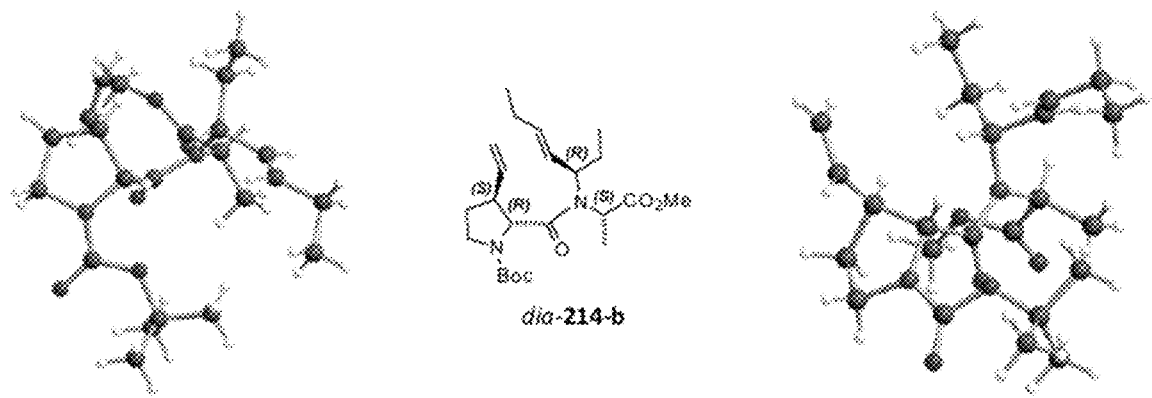

FIG. 13: Crystal structure of the dipeptide dia-214-b in two views next to the corresponding formula.

Figure 14:
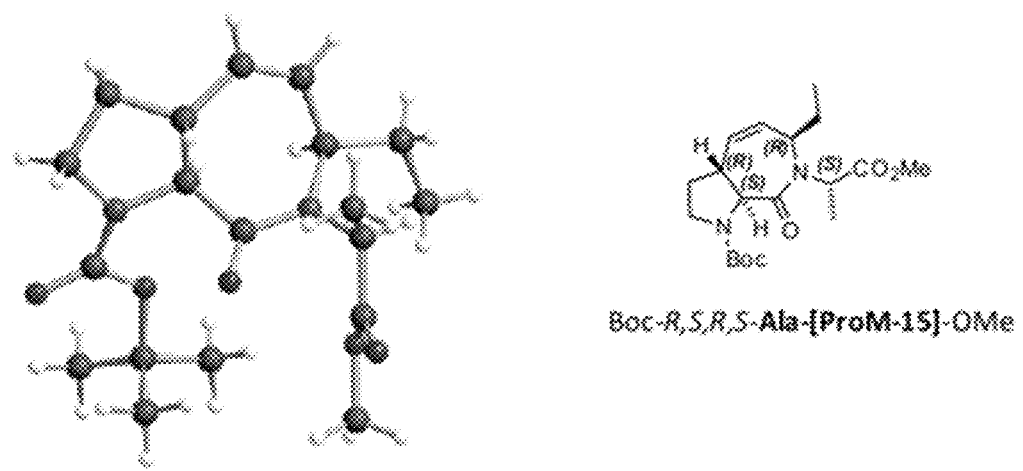

FIG. 14: Crystal structure of the bicyclic compound Boc-R,S,R,S-Ala-[ProM-15]-OMe next to the corresponding formula.

Figure 15:
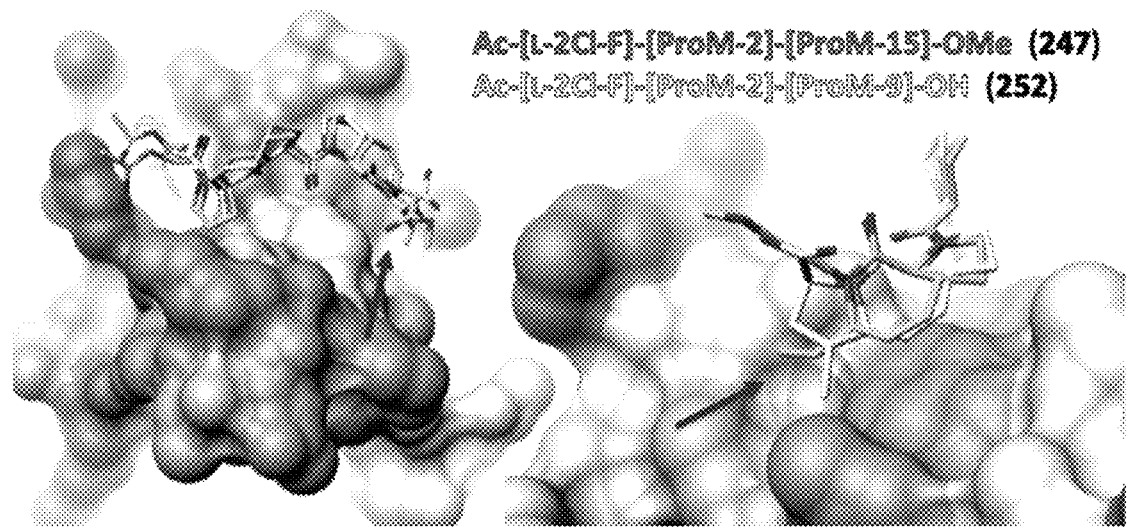

FIG. 15: Superposition of the crystal structures of ligands 247 and 252 in the complex with the EnaH-EVH1 domain. Left: Complete view of the binding groove. Right: Detailed top view of ProM-15 and ProM-9.

Figure 16:
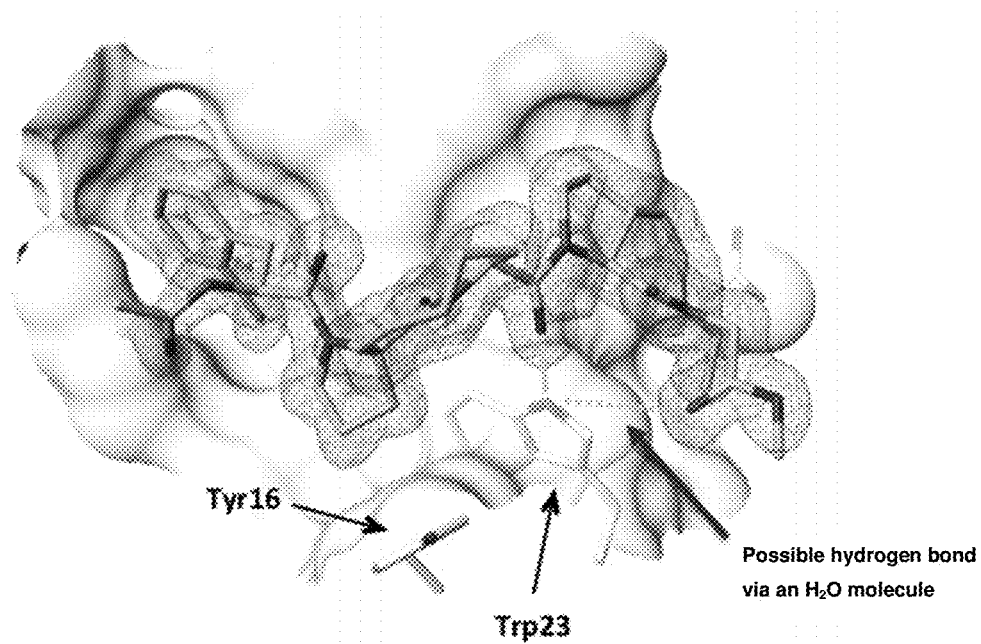

FIG. 16: Crystal structure of the ProM-15 ligand 247 in the complex with the EnaH-EVH1 domain. The electron density of the individual atoms is shown. The central, stabilizing hydrogen bond from the ProM-2 scaffold to Trp23 was included, with the presumed new hydrogen bond shown with a dashed line.

Figure 17:
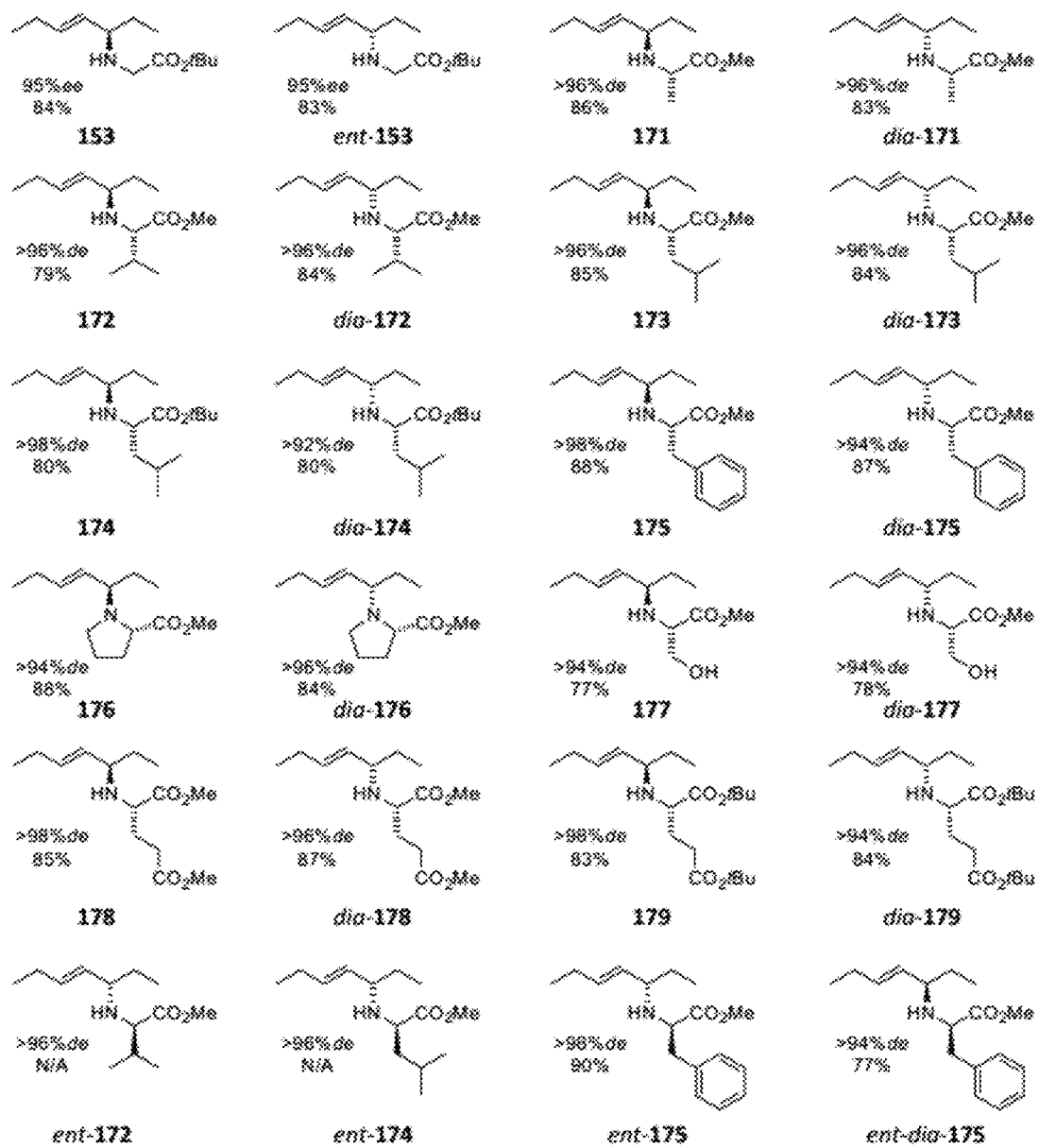

FIG. 17: All allylamines synthesized in the context of the invention by Pd-catalyzed N-allylation of various α-amino acid esters according to Scheme 5.3 and the enantiomeric or diastereomeric excesses and isolated yields achieved under optimized conditions are shown.

EXAMPLES

Ena/VASP Homology 1 Domains (EVH1)

The EVH1 domains, consisting of around 115 amino acids, play a role in numerous biological processes and are found in a large number of signaling multidomain proteins. To date, three families of EVH1 domains are known, their classification being based on ligand preference.

The first class consists of the Ena/VASP proteins, which are significantly involved in the building up and degradation of the actin cytoskeleton. Class II EVH1 domains (Homer/Vesl family) are found in postsynaptic receptor-associated proteins, and the third class of EVH1 domains are the Wiscott-Aldrich syndrome proteins (WASP) involved in actin aggregation in a regulating manner.

The Ena/VASP EVH1 Domain (Class 1 EVH1)

The Ena/VASP proteins (Ena, Mena, VASP, Evl) modulate the actin dynamics in the cytoskeleton and thus play a key role in the area of cell motility. As a result, they affect a number of important physiological processes, such as, e.g., the development of the nervous system or the function of the immune system. As a result, they also play a critical role in disease-related processes such as tumor metastasis and thus represent a highly interesting pharmacological "target", e.g. to develop a metastasis inhibitor.

All proteins of the Ena/VASP family have the same basic structure that is shown schematically in FIG. 1.

The EVH1 domain is located at the N terminus of an Ena/VASP protein. Its structure was elucidated by X-ray crystal structure analysis and NMR spectroscopy and shows great similarity with the structures of the Pleckstrin homology (PH) and the phosphotyrosine binding (PTB) domains, although the respective amino acid sequences only slightly match.

The EVH1 domain consists of a twisted β-sandwich structure which is closed on one side by an α-helix (FIG. 2).

Following the EVH1 domain there is a proline-rich region which serves to bind to proteins containing SH3 and WW domains and to profilin.

An EVH2 domain containing a G-actin and an F-actin binding site is located at the C-terminus. It also has a "coiled coil" motif that mediates the tetramerization of the system.

It is obvious that a modulation of the function over all subunits is conceivable. This study focused on addressing the PRM-EVH1 interaction, which is considered in more detail below.

The EVH1 domains of Ena/VASP proteins specifically recognize the proline-rich sequence "FPPPP" (SEQ ID NO: 1), which is found, for example, in all focal adhesion proteins (e.g. zyxin and vinculin) or in lamellipodine. These cytoskeleton-associated binding partners of the EVH1 domain serve to localize the Ena/VASP proteins at the required sites of action (e.g. focal adhesions or lamellipodia).

A delocalization of the Ena/VASP proteins from these sites by the PRM or PPII helix mimicking peptide ligands thus represents a potential modulation concept.

Another binding partner of the Ena/VASP-EVH1 domain is the ActA surface protein of the intracellular pathogen *Listeria monocytogenes*, which also contains the "FPPPP" (SEQ ID NO: 1) binding motif. As a result, the bacterium is able to localize Ena/VASP proteins on its surface and thus use their function, the formation of actin filaments, for locomotion.

However, it has been shown that by inhibiting this PRM-EVH1 interaction, e.g. by removing the FPPPP (SEQ ID NO: 1) motif from the ActA protein or injecting FPPPP (SEQ ID NO: 1)-containing peptides into the cytoplasm, the motility of the pathogen could be drastically reduced.

Design of the ProM Scaffolds

The concept behind the diproline mimetics developed by Schmalz and Kühne is illustrated in FIG. 3.

Computer-aided molecular modeling carried out by Kühne and Brockmann showed that the introduction of a "rigid" C2-vinylidene bridge (shown in green) between two neighboring prolines (2) in a stereodefined form results in a tricycle (ProM-1, "proline-rich module"), which is fixed in an almost perfect PPII conformation. In the course of their investigations, they modeled a second spirocyclic structure (ProM-2), which also mimics an almost ideal PPII helix.

Synthesis and Use of ProM-1

The first diproline mimetic synthesized was produced as an N-terminal Fmoc-protected variant (Fmoc-[ProM-1]-OH) (Scheme 1)

Scheme 1: Synthesis of Fmoc-[ProM-1]-OH.

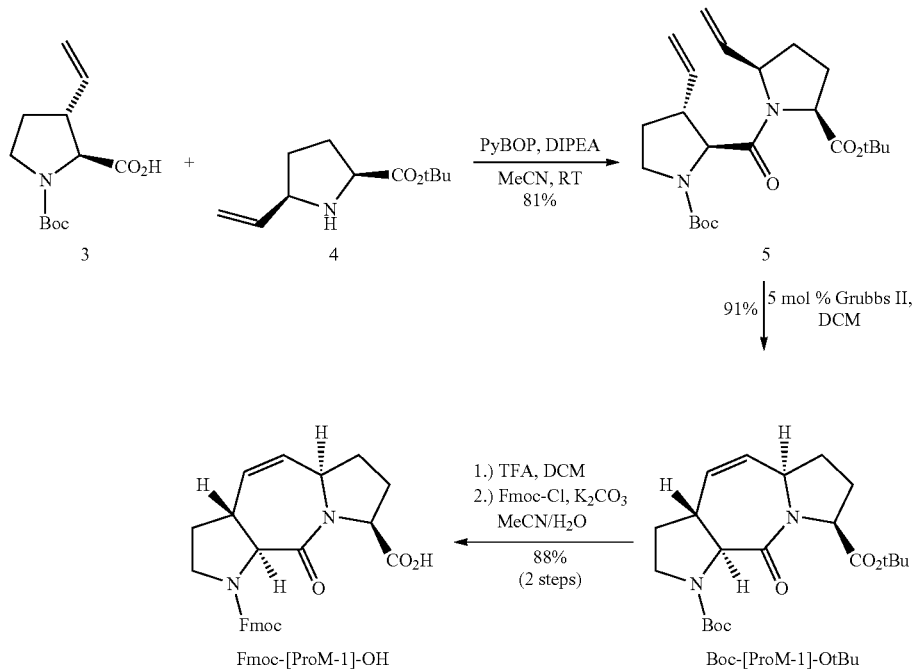

Starting from the two enantiomerically pure vinylproline building blocks 3 and 4, the Boc- and tert-butyl-protected tricycle Boc-[ProM-1]-OtBu was obtained first after peptide coupling and subsequent ruthenium-catalyzed ring-closing metathesis. Subsequent manipulation of the protecting groups provided the desired Fmoc-[ProM-1]-OH which was suitable for later solid-phase peptide syntheses.

Synthesis of ProM-2

The preparation of the spirocyclic diproline analog Fmoc-[ProM-2]-OH is possible in analogy to the synthesis of Fmoc-[ProM-1]-OH (Scheme 2)

Scheme 2: Synthesis of Fmoc-[ProM-2]-OH

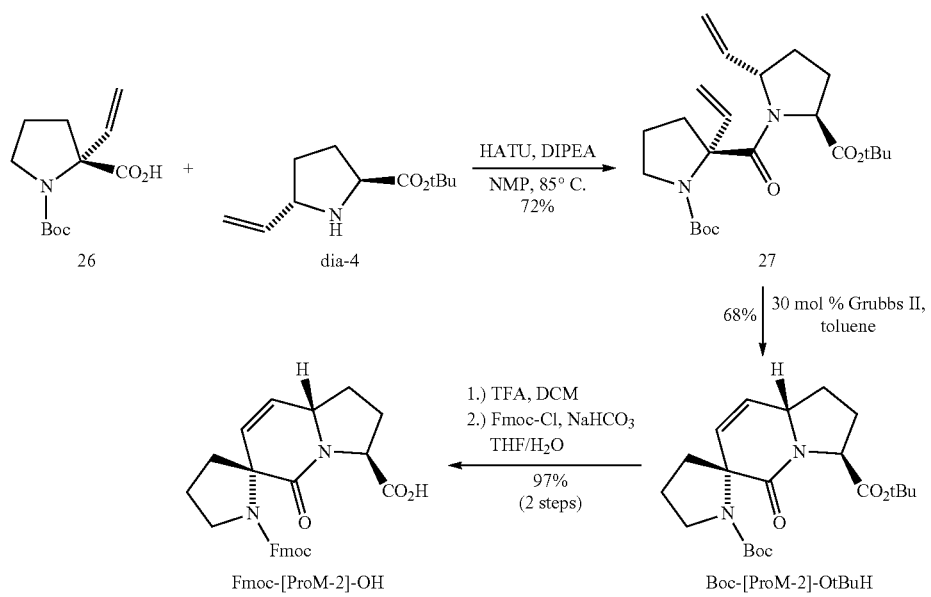

Starting from vinylprolines 26 and dia-4, the dipeptide 27 could be obtained first after peptide coupling and, after ring-closing metathesis, the tricycle Boc-[ProM-2]-OtBu could be obtained. The increased steric hindrance of building block 27 compared to 5 in the synthesis of ProM-1, however, required somewhat harsher coupling conditions and the use of larger amounts of metathesis catalyst. Final protecting group manipulation provided also here the desired Fmoc-[ProM-2]-OH which is suitable for solid-phase peptide synthesis.

Modular ProM Building Blocks-ProM Library

The general synthesis strategy of the ProM building blocks 33 can be seen on the basis of the syntheses of ProM-1 and ProM-2 (Scheme 3).

Scheme 3. General retrosynthetic disassembly of the ProM scaffolds.

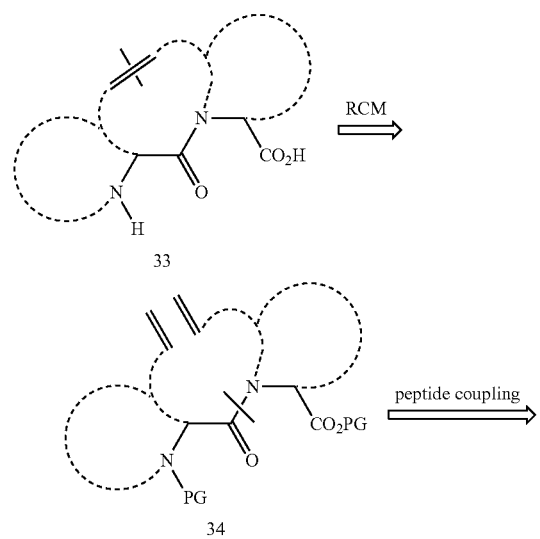

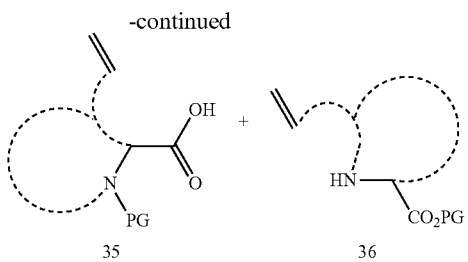

-continued

Retrosynthetically, they can be traced back to a dipeptide 34 via ring-closing metathesis (RCM) and broken down into an enantiomerically pure, vinylated acid building block 35 and an enantiomerically pure, vinylated amine building block 36 by peptide coupling. By structural variation of building blocks 35 and 36, it should therefore also be possible to adapt or optimize the final ProM diproline mimetics to the needs of the respective protein surface.

In addition to the discussed mimetics ProM-1 and ProM-2, nine further ProM scaffolds have already been synthesized (FIG. 4). The publications that have appeared to date are given for all of the ProM building blocks shown.

The ProM-8, ProM-1, ProM-4 series and the ProM-9 scaffold are specific examples of the structural variability of ProMs (Scheme 4).

Scheme 4: Retrosynthesis of the building blocks ProM-8, ProM-1 and ProM-9.

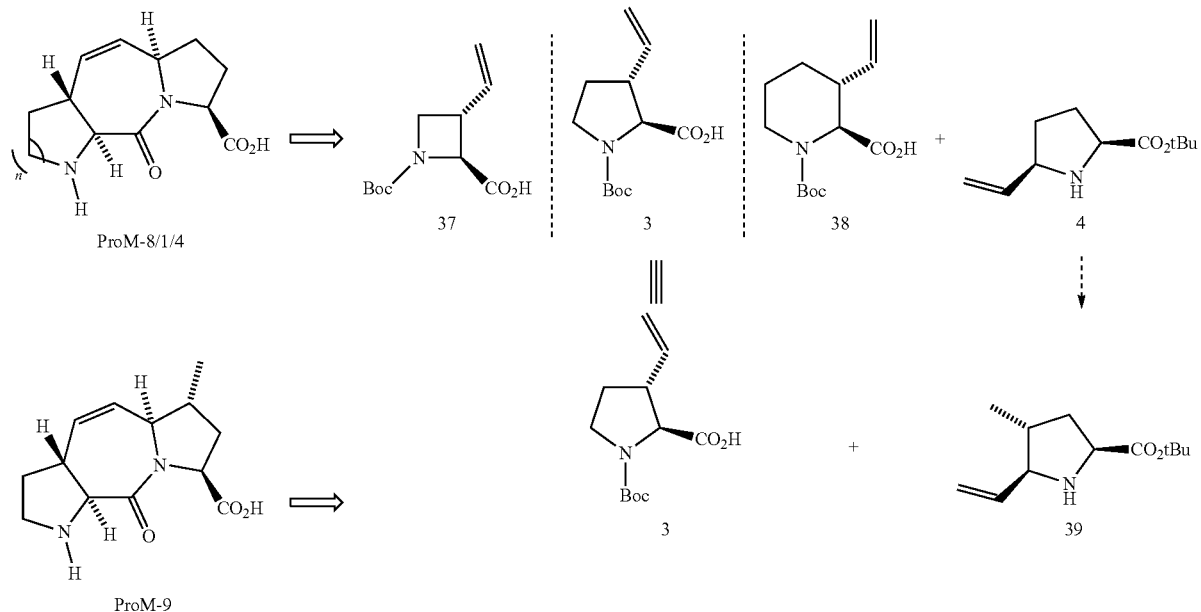

Through targeted synthesis of the homologous series of acid building blocks 37, 3 and 38, the concept of ring reduction or expansion could be used to address shallower and deeper binding grooves on the PBD surface.

The targeted introduction of an additional methyl group into the amine building block 4, however, enabled access to a ProM-1 derivative with an additional hydrophobic interaction site.

Some of these ProM diproline mimetics (ProM-1 to ProM-4) have already been used to develop a low-molecular, highly selective, peptidic, but fully synthetic Ena/VASP-EVH1 inhibitor (PPII secondary structure mimic).

Development of an Ena/VASP-EVH1 inhibitor

Opitz et al. reported in a publication published in 2015 (R. Opitz, M. Müller, C. Reuter, M. Barone, A. Soicke, Y. Roske, K. Piotukh, P. Huy, M. Beerbaum, B. Wiesner, M. Beyermann, P. Schmieder, C. Freund, R. Volkmer, H. Oschkinat, H.-G. Schmalz, R. Kühne, PNAS 2015, 112, 5011-5016) on the successful use of ProM scaffolds as diproline mimetics in the development of a "small molecule" Ena/VASP-EVH1 inhibitor (FIG. 5).

Starting from the ActA-derived peptide ligand Ac-SFEFPPPPTEDEL-NH$_2$ (SEQ ID NO: 2) (40) which binds to the Ena/VASP-EVH1 domain in the micromolar range, all four prolines in the core motif (FPPPP; SEQ ID NO: 1) of the ligand were systematically replaced by the rigidized scaffolds ProM-1 to ProM-4. The best results resulted from the substitution of the first proline pair with ProM-2 (FPPPP; SEQ ID NO: 1) and the second pair with ProM-1 (FPPPP; SEQ ID NO: 1). In further studies it was also shown that replacing the phenylalanine (F) with the unnatural amino acid L-2-chlorophenylalanine (L-2CI-F) led to a drastic gain in affinity. The resulting compound 41 represented the first.peptide ligand with a fully synthetic core motif (canonical binding mode), binding to the Ena/VASP-EVH1 domain in the nanomolar range.

However, to develop a "small molecule" it was necessary to significantly reduce the molecular weight of compound 41. Interestingly, it was possible to remove the flanking epitopes (SFE & TEDEL; SEQ ID NO: 3) without a significant loss of the binding affinity of 41, whereas in the case of wt ligand 40 this led to an almost complete loss of binding ability (see 42 & 43). The ligand Ac-[L-2CI-F]-[ProM-2]-[ProM-1]-OH (43) was the most efficient, small-molecule inhibitor for addressing all three Ena/VASP-EVH1 domains. Compound 43 showed a 180-fold (EVL- and Ena-EVH1) or even 280-fold (VASP-EVH1) increased binding affinity compared to the natural peptide 42, which was reduced to the binding sequence. In addition, the canonical binding mode of the ligand 43 could be demonstrated via crystal structures and a cell-permeable substance 44 could be produced by esterification of the free acid.

The successful development of an Ena/VASP-EVH1 inhibitor could also be confirmed in biological studies. It has been shown that compound 44 delocalizes the protein VASP from focal adhesions and out of the "leading edge", as a result reduces the formation of actin filaments and thus drastically reduces the motility of highly metastatic colorectal and breast cancer cells.

In summary, the ProM diproline mimetics are useful, modular and rationally designed building blocks for the development of specific peptide mimetics for addressing PRM-PBD interactions.

Objective and Conception of the Present Invention

The present invention is based on the above-mentioned studies in the area of PPII secondary structure mimetic development, e.g. the production of modular diproline analogs in PPII conformation (ProMs) and their use as Pro-Pro equivalent in the core motif of a PRM for the synthesis of a highly selective Ena/VASP-EVH1 inhibitor 43 (FIG. 6).

With the aim of further increasing the binding affinity of the peptide ligand to the EVH1 domain or to address further PBDs, numerous "structurally optimized" ProM scaffolds (ProM-1 to ProM-10) have been synthesized in recent years through analysis of the results obtained and further modeling studies. Starting from ProM-1, these are all due to either a change in the stereoconfiguration or a modification of the carbon structure (variation of size and substituents) in order to specifically address further binding pockets in the domain or to meet steric requirements.

The methyl-substituted ProM-1 derivative ProM-9 is a relevant example for this work.

As a ProM-1 replacement in the Ena/VASP-EVH1 inhibitor Ac-[L-2Cl-F]-[ProM-2]-[ProM-1]-OH (43), it produced a binding affinity that was increased by a factor of 5-10.

The added methyl substituent addressed a hydrophobic pocket of the domain and thus contributed positively to the binding.

As a result of these investigations, the interest in ProM-1 and ProM-9 derived bicyclic structures of the type ProM-15 (Scheme 5) grew:

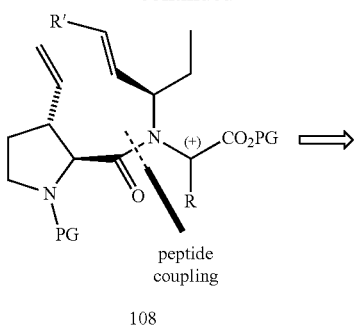

peptide coupling

108

Scheme 5: Derivation of the ProM-15 scaffold from the known structures ProM-1 and ProM-9.

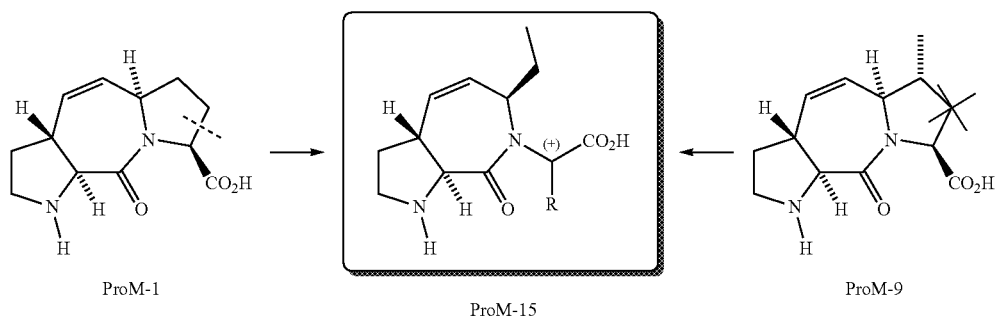

ProM-1      ProM-15      ProM-9

In the case of R=H, ProM-15 can be regarded as an "east ring-opened" ProM-1 derivative or as a ProM-9 derivative reduced by one carbon atom. On the one hand, computer modeling studies showed that increased flexibility of the C-terminus of ProM-1 in 43 would represent a promising option for increasing the binding affinity to the Ena/VASP-EVH1 domain through the possible formation of hydrogen bonds.

On the other hand, ProM-15 would offer the possibility of "mimicking" the methyl substituent of ProM-9 while reducing the molecular weight and thus also using the previously successfully addressed hydrophobic binding pocket. Accordingly, ProM-15 should combine the positive binding properties of ProM-9 with a reduction in molecular weight and an increase in C-terminal flexibility.

According to the established, general synthesis strategy of the ProM scaffold, ProM-15 can be traced back to the enantiomerically pure acid and amine building blocks 3 and 109 (Scheme 6).

Scheme 6: Retrosynthetic synthesis of diproline analogs of the type ProM-15.

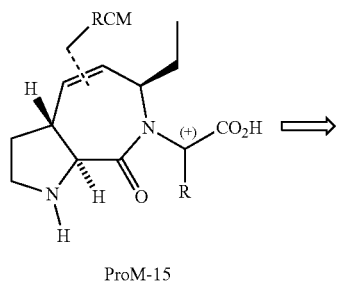

ProM-15

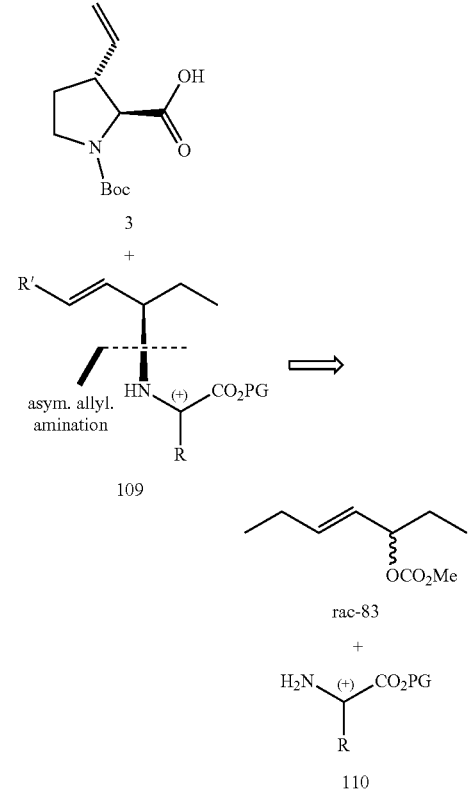

The target structure ProM-15 results from ruthenium-catalyzed ring-closing metathesis (RCM) from a dipeptide of type 108, which in turn can be traced back to the already known "Zaminer's acid" (3) and an allylamine 109 by peptide coupling. The stereoselective synthesis of allylamines of type 109 poses a particular challenge. For this purpose, a transition metal-catalyzed asymmetric allylic amination of symmetrically 1,3-disubstituted substrates (to avoid regioisomers) using amino acid N nucleophiles could be used. Starting from the racemic carbonate rac-83 and a simple amino acid ester 110, available in both absolute configurations, in principle all four stereoisomers could be prepared in a targeted manner using chiral ligands. Based on the few (moderately successful) literature examples, it was planned to develop first reliable conditions for the efficient and stereoselective synthesis of N-allylated amino acid esters of type 112 under palladium catalysis (Scheme 7).

L-phenylalanine could enter into additional hydrophobic interactions with the EVH1 domain. L-glutamic acid appeared to be beneficial because the "TEDEL" (SEQ ID NO: 3) residue of the ActA peptide would be mimicked and thus the formation of hydrogen bonds with surrounding amino acids would be possible. Furthermore, ProM-15 derivatives of L-tyrosine could open up a way to address WW domains with a core motif "PPxY". Accordingly, the objective was to synthesize the desired diproline analogs of the ProM-15 type (e.g. as a Boc-protected variant) based on glycine and, for example, L-phenylalanine, after the successful production of allylamines of type 112 (FIG. 8).

If necessary, it was planned to optimize the final, already established synthesis steps (peptide coupling, ring-closing metathesis) for the special systems. The nomenclature of the

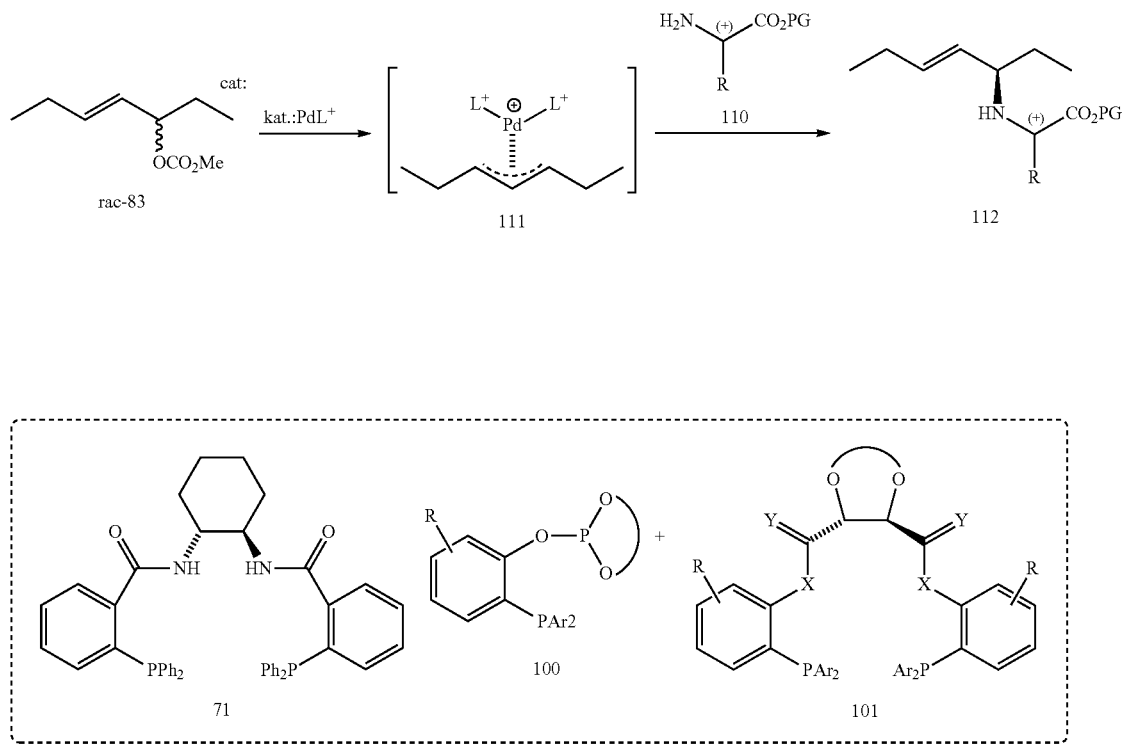

Scheme 7: Intended synthesis of N-allylated amino acid esters of type 112 using chiral ligands.

It was particularly important to identify suitable chiral ligands that allow the configuration of the new stereocenter to be controlled in a highly selective manner, regardless of the absolute configuration of the amino acid building block 110 used. In this context, in addition to established ligands such as the Trost ligand, it was also planned to test the developed phosphine-phosphite ligands 100 and the C2-symmetrical bisphosphine ligands of type 101, the modular structure of which allows a comparatively simple (individual) structure optimization. The use of various amino acid esters 110 could provide access to a large number of ProM-15 derivatives, which could enter into further interactions with the domain through the additional substituents (FIG. 7).

The modeling studies carried out revealed that in addition to glycine (R═H), phenyl alanine (R═Bn) or functionalized amino acids such as glutamic acid (R═(CH$_2$)$_2$CO$_2$H) would also be of interest. ProM-15 derivatives based on target compounds is defined as follows: N-terminus-configuration of the centers a,b,c,d-amino acid [ProM-15]-C-terminus.

Due to the very positive results in the development of an Ena/VASP-EVH1 inhibitor, in vivo experiments were aimed at. This required the provision of large amounts of substance (>2 g) of the selected peptide ligand Ac-[L-2Cl-F]-[ProM-2]-[ProM-1]—NH$_2$ (113), which were not accessible via the previously used solid phase peptide synthesis to build up the inhibitor (<5% yield over 2 steps to form the free acid 43). Therefore, a further focus of this invention was on the development of an efficient strategy for linking the ProM building blocks in the liquid phase and the establishment of a multi-gram synthesis of ligand 113 (Scheme 8).

Scheme 8: Structure of the peptide ligand 113 from the building blocks ProM-1, ProM-2 and L—2Cl—F (114).

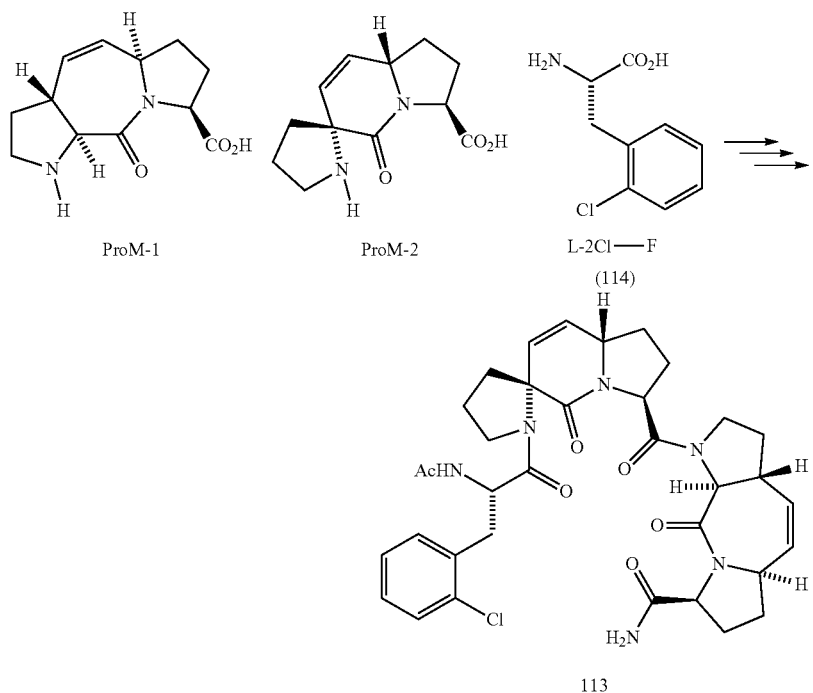

113

In addition to the scaffold ProM-1, which was provided in sufficient quantities, ProM-2 was planned to be produced on a multi-gram scale using the well-known synthesis route according to Reuter and Soicke.

In this respect, the relatively inefficient final steps of the peptide coupling (55% yield) and ring-closing metathesis (30 mol % Grubbs II catalyst required) had to be re-examined and optimized.

Furthermore, there was the challenge to produce the peptide ligand 113 with a C-terminal amide function. To date, the free acid 43 resulting from the solid phase peptide synthesis has been converted into the ethyl ester 44 in order to make the ligand permeable to cells. However, it was expected that the amide derivative 113 would have an increased metabolic stability with similar binding affinity and permeability and could thus deliver even better results in the planned in vivo experiments.

Last but not least, after the successful development of a ligand synthesis in the liquid phase for the ProM-1-based ligand 113, it was planned to use this method subsequently also for the synthesis of ProM-15-containing ligands 115 (FIG. 9).

By finally measuring the binding affinity of the new ligands 115 to the EVH1 domain and crystallizing 115 with it, the in silico postulated effects of a substitution of ProM-1 or ProM-9 by ProM-15 had to be experimentally evaluated.

Results
Catalysis Results

In the context of the invention, a highly selective methodology for the synthesis of allylamines of type 112* by palladium-catalyzed asymmetric allylic amination of the carbonate rac-83 and the use of various α-amino acid esters 110 as N-nucleophiles was successfully developed (Scheme 9).

Scheme 9: Synthesis of allylamines of type 112* or 153* by the palladium-catalyzed asymmetric allylic amination of the carbonate rac-83 using various a-amino acid esters 110 as N-nucleophiles, as developed in this study. Under the optimized reaction conditions, the formation of carbamate by-products ambo-136 could be completely suppressed.

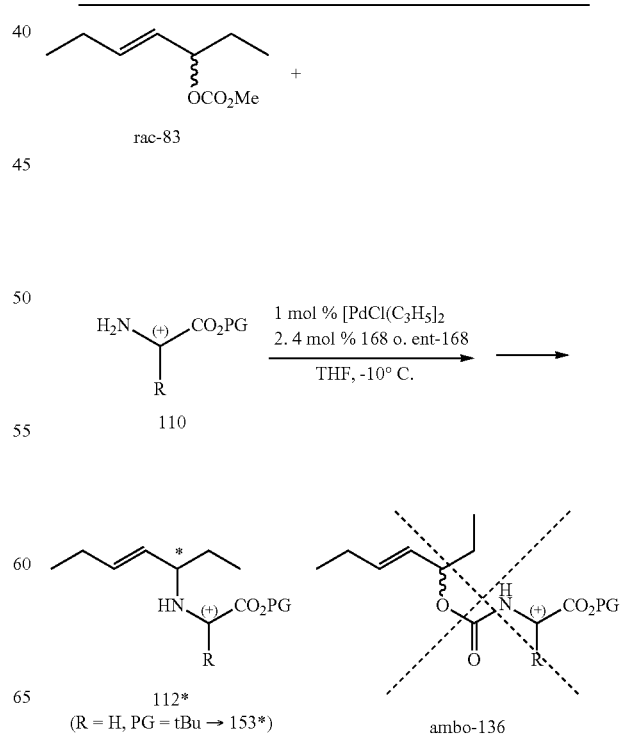

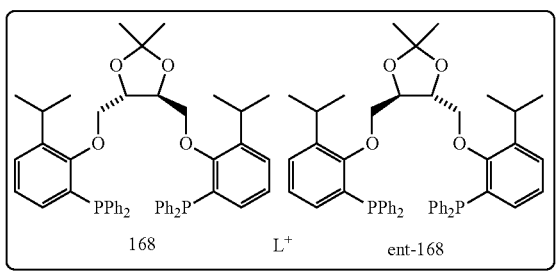

168  L+  ent-168

In the first experiments, allylic carbamates of the ambo-136 type were surprisingly obtained using a literature procedure, the formation of which could be suppressed by a drastic increase in the concentration of the reaction solution. After ligand screening and further optimization steps, conditions were found which, using only 1 mol % of a Pd source and 2.4 mol % of a chiral ligand (168 or ent-168), lead to the formation of the glycine-based allylamine 153* in 95% ee and with a yield of 74-84%. The control of the configuration of the new stereocenter was possible through the choice of the corresponding chiral ligand (168-+S; ent-168-+R).

Even when using chiral nucleophiles 110, the substrate-induced diastereoselectivity previously demonstrated could be overridden. The occurrence of matched/mismatched combinations was not observed, so that equivalent access to all four stereoisomers was possible. The selectivities and yields achieved were all in an excellent range and clearly surpass the few known literature examples for similar transformations.

The synthesized allylamines and the selectivities achieved in the catalysis are shown again in summary in FIG. 10:

Synthesis of Dipeptidic Structures of Type 180

According to the retrosynthetic synthesis of ProM-15 presented above, the dipeptidic structures of type 180 had to be generated by linking the Zaminer's acid building block (3) and the allylic amines 112 produced by the allylic aminations (Scheme 10).

Scheme 10: For the synthesis of the target structure ProM-15, the preparation of dipeptidic structures of type 180 by peptide coupling of building blocks 3 and 112 is important.

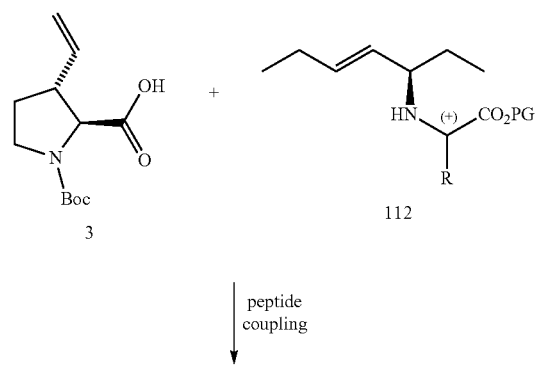

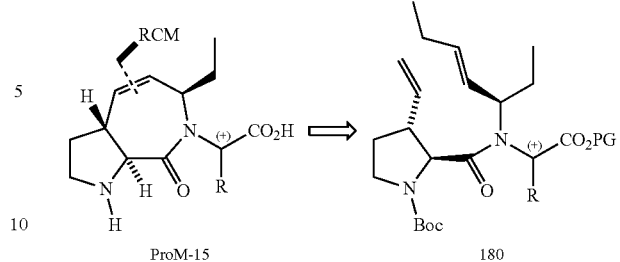

ProM-15  180

In the context of the various ProM syntheses, two different coupling reagents were generally used to achieve such peptide couplings. In most cases a linkage was achieved under mild reaction conditions (at rt) by using PyBOP (181) in combination with Hünig's base (DIPEA).

Synthesis of the Dipeptide Mimetic Boc-Gly-[ProM-15]-OMe

For the synthesis of the glycine-based ProM-15 derivative, the enantiomerically pure Zaminer's acid building block (3) had to be coupled with the allylic amine 153, which was accessible in 95% ee by palladium-catalyzed allylic amination (Scheme 11).

Scheme 11: Synthesis of the dipeptidic structure 183 using Ghosez's reagent.

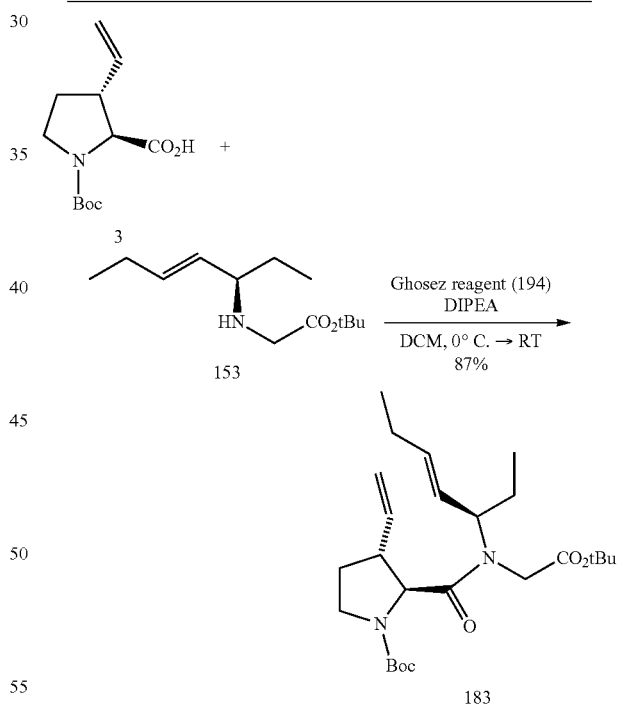

By using the coupling strategy developed previously, the desired dipeptide 183 was prepared after activation of the acid 3 by Ghosez's reagent, as well as using 1.1 eq. of amine 153 and DIPEA with a very good yield of 87%. In addition to the significantly milder reaction conditions and the increased yield compared to the previously described coupling using the coupling reagent HATU, an almost quantitative conversion of the allyl amine 153 took place here (determined by TLC). The removal of the small amount of the remaining amine building block 153 was no longer a problem and, after washing with dilute HCl, could be achieved by column chromatography without major losses.

The corresponding enantiomer ent-183 could be prepared under the same conditions and in a comparable yield. Said enantiomer was then used to optimize the next synthesis steps, since the 2R,3S enantiomer of the Zaminer's acid (ent-3) required for the preparation, unlike 3 itself, was available in large quantities at the time the synthesis was developed.

The H-NMR spectra of the two diastereomers differ significantly from each other, so that the diastereomeric purity of the selectively synthesized substances could be clearly demonstrated. The determination of the diastereomeric ratio from previously synthesized mixtures of the stereoisomers was not successful because there were no completely isolated signals of the individual diastereomers.

In addition, the spectra showed a very high complexity due to the occurrence of multiple sets of signals, which by 2D H,H-NOESY spectroscopy could be clearly traced back to the presence of rotamers (differentiation between NOE and exchange signals possible). Interestingly, dipeptides 183 and ent-dia-183 each formed four rotamers, whereas for all further dipeptides based on other amino acids only two rotamers could be observed. Since very different chemical shifts were always apparent for the two "glycine protons" (in the a position to the nitrogen atom and to the ester carbonyl carbon), it is assumed that the two additional rotamers are due to the formation of a probably intramolecular hydrogen bond.

In the next step of the synthesis, it was planned to form the bicyclic ProM-15 structure by ruthenium-catalyzed ring-closing metathesis (RCM). In the preparation of all previous ProM scaffolds, the metathesis reaction was carried out using the Grubbs II catalyst (208), wherein the required high catalyst loading of 10-30 mol % was a problem that had not yet been resolved. During the synthesis of replenishment of the ProM-2 building block, which was carried out within the scope of this work, however, a slightly optimized synthesis procedure was developed that allowed the amount of Grubbs II to be reduced. These improved conditions have now been applied to the ProM-15 system, with initial synthesis attempts initially being made with the enantiomeric form of the dipeptide ent-183, which is accessible in large quantities (Scheme 12).

Scheme 12. RCM of ent-183 to form Boc-S,R,S-Gly-[ProM-15]-OtBu using the Grubbs II catalyst (208).

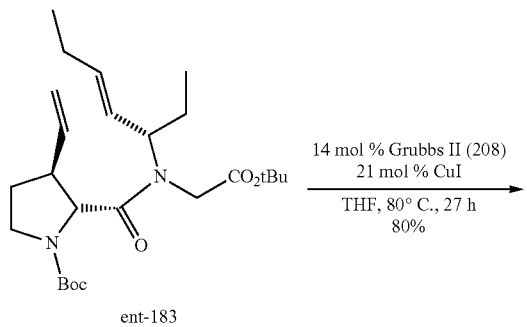

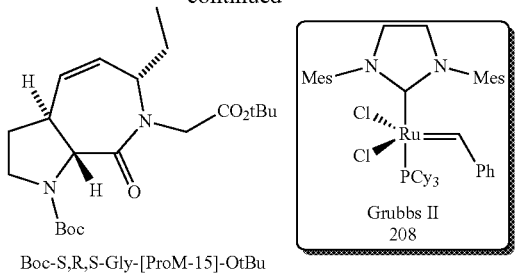

Boc-S,R,S-Gly-[ProM-15]-OtBu

By adding a total of 14 mol % Grubbs II catalyst (208) and 21 mol % copper (I) iodide (CuI) to the dipeptide ent-183 in portions and refluxing the reaction mixture in THF for 27 h, the desired product could be isolated in a good yield of 80%. Based on the findings gained from the ProM-2 metathesis, optimization of Grubbs II (208) to reduce the high catalyst loading, which is also necessary here, was abandoned and instead a subsequent screening of various metathesis catalysts was aimed at. During the literature search to identify suitable catalyst candidates, it was found that the reaction is very complex and a rational choice of the catalyst is usually difficult. The success of the metathesis depends in a special way very heavily on the interaction of all reaction parameters (solvent, concentration of the reaction mixture, temperature, reaction time), which have to be adapted highly specifically for each substrate.

As a rule, the best results for sterically demanding metatheses were achieved with the nitro Grela catalyst (209) or the Hoveyda II catalyst (210) in toluene at 70° C. These parameters served as the starting point for the optimization of the RCM of ent-183 aimed at here, wherein the substrate concentration of 0.1 mol/l was initially retained. Another catalyst was compound 211 developed by Stewart et al., which was particularly convincing in the challenging formation of tetra-substituted double bonds by RCM.

The catalyst was always added in portions, since better yields could be achieved in connection with the optimization of the ProM-2 metathesis. An amount of 6 mol % was defined as the maximum tolerable catalyst loading.

The results of the screening are summarized in Scheme 13.

Scheme 13: Screening of various catalysts in the ring-closing metathesis of the dipeptide ent-183 and optimization of the reaction conditions.

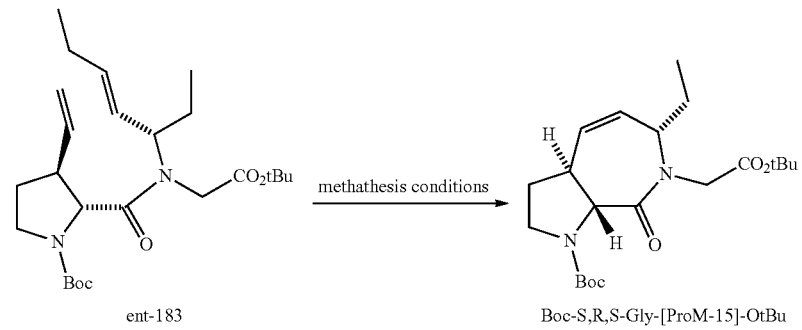

ent-183    methathesis conditions    Boc-S,R,S-Gly-[ProM-15]-OtBu

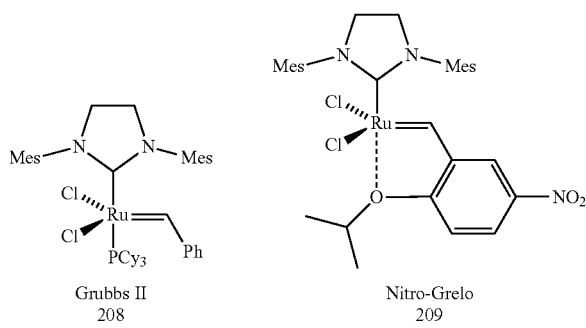

Grubbs II
208

Nitro-Grelo
209

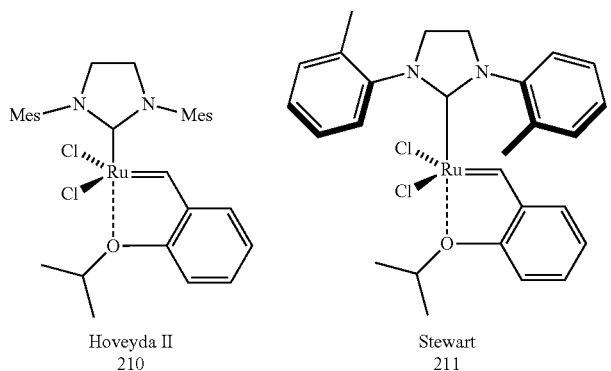

Hoveyda II
210

Stewart
211

Under the standard conditions chosen, the nitro Grela and Hoveyda II catalysts recommended by Bieniek et al. showed in fact the best results.

With only 6 mol % catalyst and a significantly shortened reaction time of only 5 h, 78% and 80%, respectively, of the cyclized product Boc-S,R,S-Gly-[ProM-15]-OtBu could be isolated. Extending the reaction time to 22.5 h did not lead to any significant increase in the yield. It is known, that the change from toluene to perfluorinated aromatic solvents results in a substantial increase in activity of many metathesis catalyst. This could be confirmed here by using hexafluorobenzene (HFB). For the two best catalysts to date, 209 and 210, an increase in yield of around 10% was achieved, with the Hoyveda II catalyst providing the best result with 91%. However, here also, a prolonged reaction time did not lead to an improvement in yield. Since the metatheses were carried out in significantly more dilute reaction mixtures, the reaction solution was then diluted by half.

However, the minimally increased yield resulting from this was in no relation to the value of the solvent used. Finally, it was found that in comparison to adding the catalyst 210 in portions three times at 2 mol % each after 0 h, 2 h and 3.5 h, the same results were achieved with an addition of 4 mol % at the beginning and a further 2 mol % after 3.5 h.

The best reaction conditions obtained from the screening were subsequently used for the synthesis of the desired stereoisomer Boc-R,S,R-Gly-[ProM-15]-OtBu (Scheme 14).

Scheme 14: Synthesis of Boc-R,S,R-Gly-[ProM-15]-OtBu by RCM of 183 under optimized conditions.

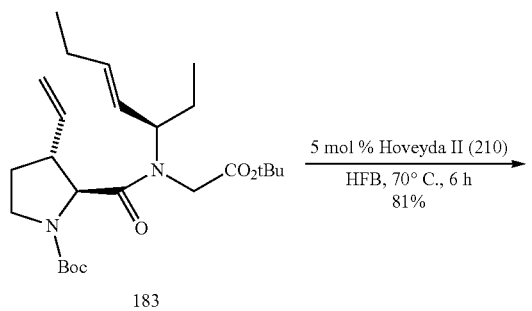

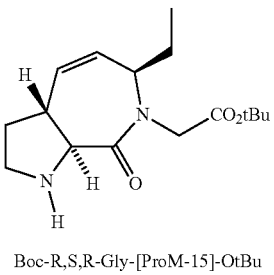

Boc-R,S,R-Gly-[ProM-15]-OtBu

In the significantly larger reaction batch, the desired cyclization product was obtained with a somewhat reduced but still very good yield of 81%. This yield was not higher than when Grubbs II was used as the catalyst, but a significant reduction in the amount of catalyst from 14 mol % to 6 mol % and the reaction time from 27 h to 6 h, as well as a drastic simplification of the reaction procedure could be achieved. After purification by column chromatography, ruthenium residues were removed by stirring using Quadra-Sil AP, a silica-based metal scavenger. This final purification was carried out at the end for all metatheses described in this work and provides the products as almost white solids.

The two enantiomers Boc-R,S,R-Gly-[ProM-15]-OtBu and Boc-S,R,S-Gly-[ProM-15]-OtBu could be crystallized from a mixture of n-heptane/EtOAc=1/1 at this step, and thus for the first time information about the configuration of the stereocenter generated in the Pd-catalyzed allylic amination could be obtained. The quality of the crystals produced was sufficient for a clear determination of the relative configuration by X-ray crystal structure analysis.

In FIG. 11, the crystal structures are shown above the corresponding formulae.

Finally, it should be noted that attempts were always made to re-isolate unreacted dipeptide 183 or ent-183. Interestingly, this could not be achieved in any case, with the substance isolated instead having the same Rt value (0.52, silica, cHex/EtOAc=1/1) as the substrate. A complete elucidation of the structure of this compound was not possible, however, a structural relationship to the original substrate 183 could be clearly identified by NMR analysis, since the "characteristic" signals of the dipeptide 183 were still present. However, significant signal shifts were noted in the area of the double bond protons, which are presumably due to an isomerization of the olefin, a well-known side reaction of RCM.

Apparently, the resulting compound did not cyclize or significantly more slowly than the original compound 183 because no significant quantities of other by-products could be detected. Similar observations with regard to the re-isolation of starting material were also made in the subsequent metatheses for the preparation of ProM-15 derivatives, wherein small amounts of a by-product that was difficult to separate from the product were also obtained.

For the upcoming synthesis of a ProM-15-containing peptide ligand, Boc-R,S,R-Gly-[ProM-15]-OtBu had to be converted into a methyl ester by manipulating the protecting group in a final synthesis step. This transesterification was carried out according to a slightly modified two-step procedure from Reuter.

Using thionyl chloride in MeOH, all protecting groups were removed first and the methyl ester was formed. This was followed by another N-terminal Boc protection of the intermediate 213 with di-tert-butyl dicarbonate ($Boc_2O$) in an aqueous alkaline solution (Scheme 15).

Scheme 15: Final protecting group manipulation for the synthesis of Boc-R,S,R-Gly-[ProM-15]-OMe.

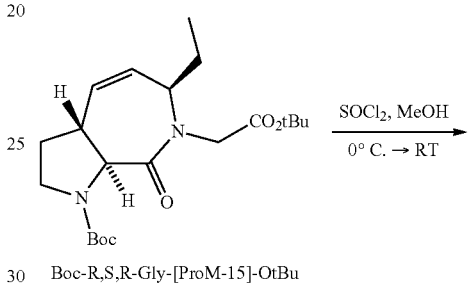

Boc-R,S,R-Gly-[ProM-15]-OtBu

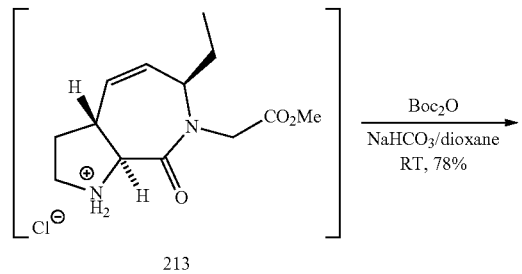

213

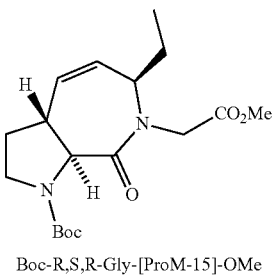

Boc-R,S,R-Gly-[ProM-15]-OMe

After purification by column chromatography (silica, DCM/EtOAc=1.5/1), the desired final target structure Boc-R,S,R-Gly-[ProM-15]-OMe was obtained in 78% yield as a colorless, highly viscous oil.

Finally, the three-step synthesis of the targeted diproline analog Boc-R,S,R-Gly-[ProM-15]-OMe, starting from the enantiomerically pure building blocks Zaminer's acid 3 and allylamine 153, is clearly summarized (Scheme 16).

Scheme 16: Synthesis of Boc-R,S,R-Gly-[ProM-15]-OMe starting from Zaminer's acid (3) and the allylamine 153

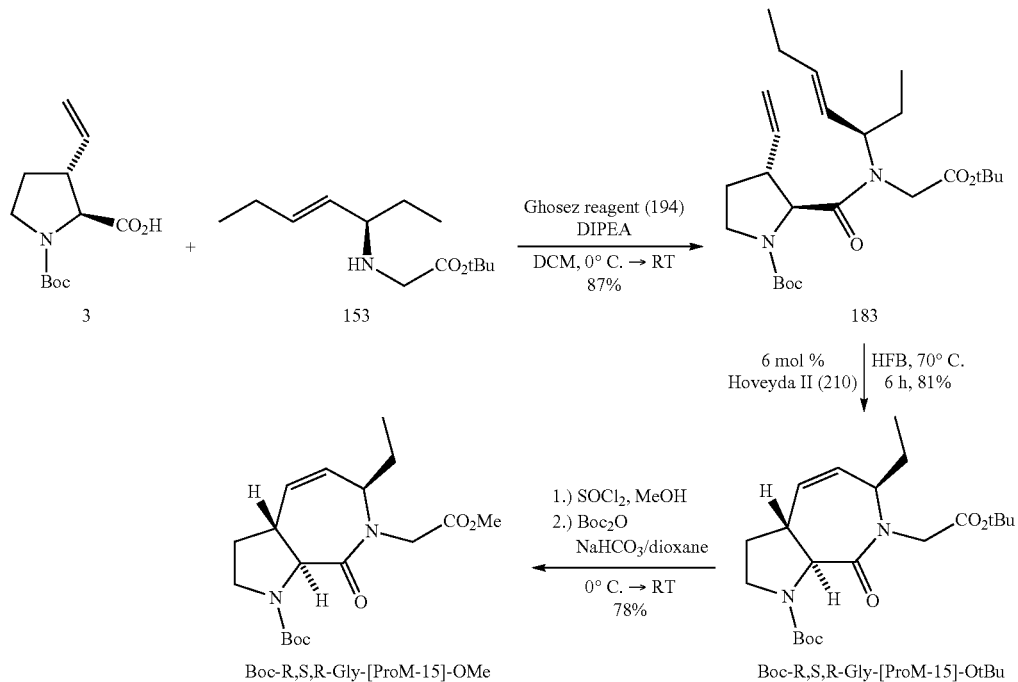

Synthesis of the Dipeptide Mimetic Boc-Phe-[ProM-15]-OMe

As described above, in addition to the glycine-based R,S,R-Gly-[ProM-15], a derivative based on L-phenylalanine with otherwise the same relative configuration was also of interest. However, since the 2S,3R-Zaminer's acid 3 required for the preparation of this building block was not available at the time of the synthesis development, it was decided to synthesize first the enantiomeric compound S,R,S,R-Phe-[ProM-15]-OMe from 2R,3S-Zaminer's acid ent-3 available in copious amounts. Furthermore, since all four stereoisomers of the phenyl alanine-based allylamine 175* were accessible in a targeted manner through the previously developed Pd-catalyzed allylic amination, the remaining three diastereomers of this compound were prepared in addition to the desired target structure.

The results of the peptide coupling of the individual stereoisomers of 175* with the 2R,3S enantiomer of the Zaminer's acid ent-3 are summarized in Scheme 17:

Scheme 17: Peptide coupling of Zaminer's acid (ent-3) with the diastereomerically pure dipeptides 175* after activation with Ghosez's reagent (194). The isolated yields of the four diastereomers are provided after purification by column chromatography.

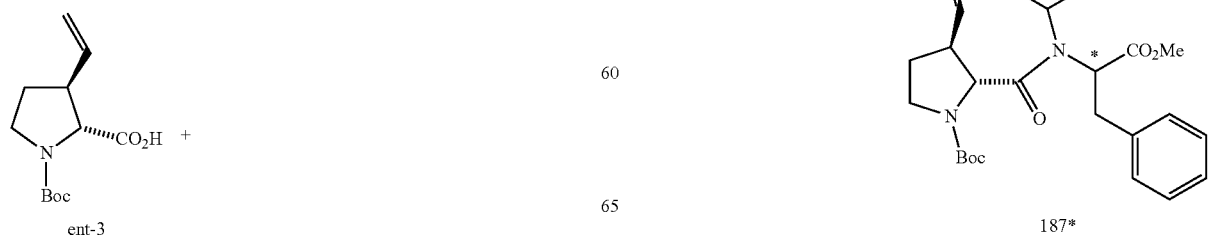

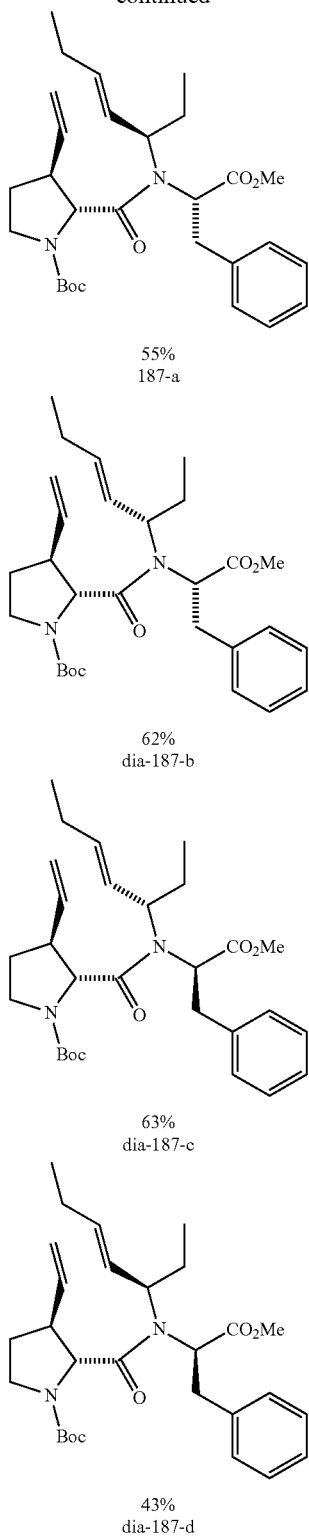

55%
187-a

62%
dia-187-b

63%
dia-187-c

43%
dia-187-d

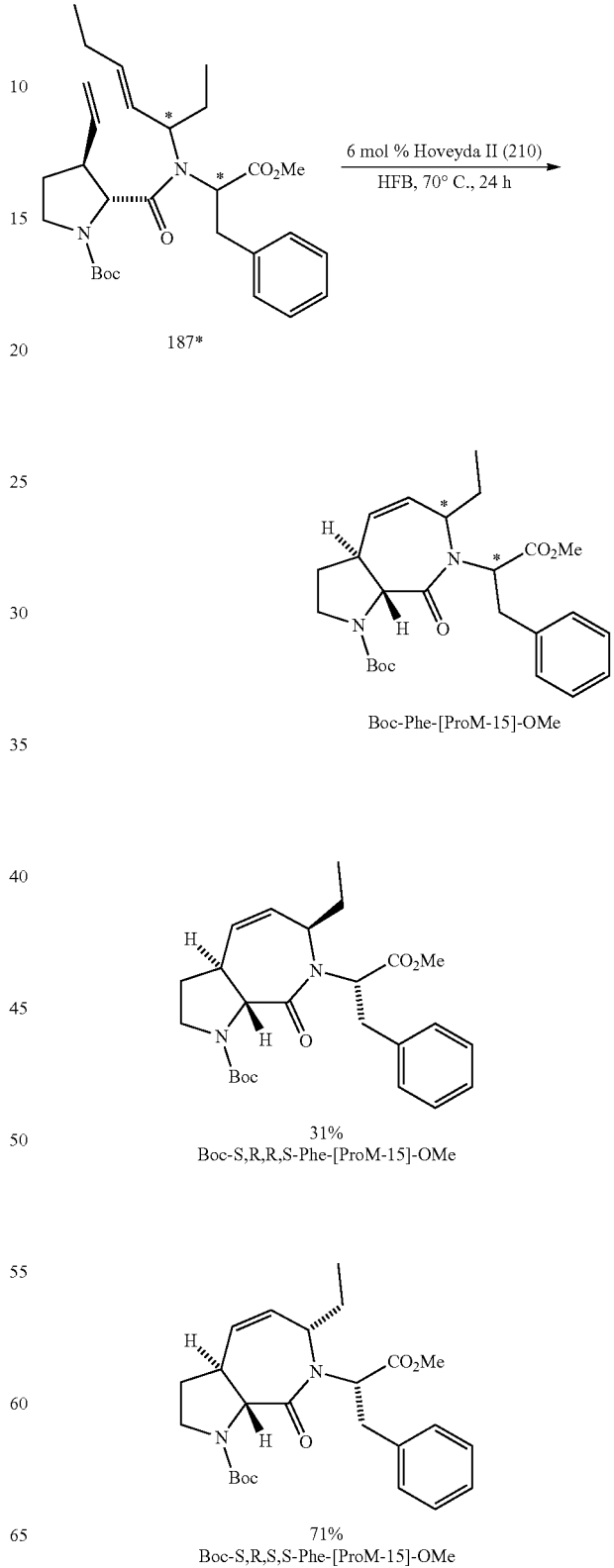

Scheme 18: RCM of dipeptides 187* using Hoveyda II catalyst (210) in hexafluorobenzene (HFB). The isolated yields of the cyclization products Boc-Phe-[ProM-15]-OMe after purification by column chromatography and removal of ruthenium residues by QuadraSil AP are provided.

31%
Boc-S,R,R,S-Phe-[ProM-15]-OMe

71%
Boc-S,R,S,S-Phe-[ProM-15]-OMe

Accordingly, it was possible to prepare the dipeptides 187-a to dia-187-d in a targeted manner as enantiomerically and diastereomerically pure substances. In the following step, the desired Phe-[ProM-15] building blocks could be prepared successfully by Hoveyda II-mediated ring-closing metathesis (Scheme 18).

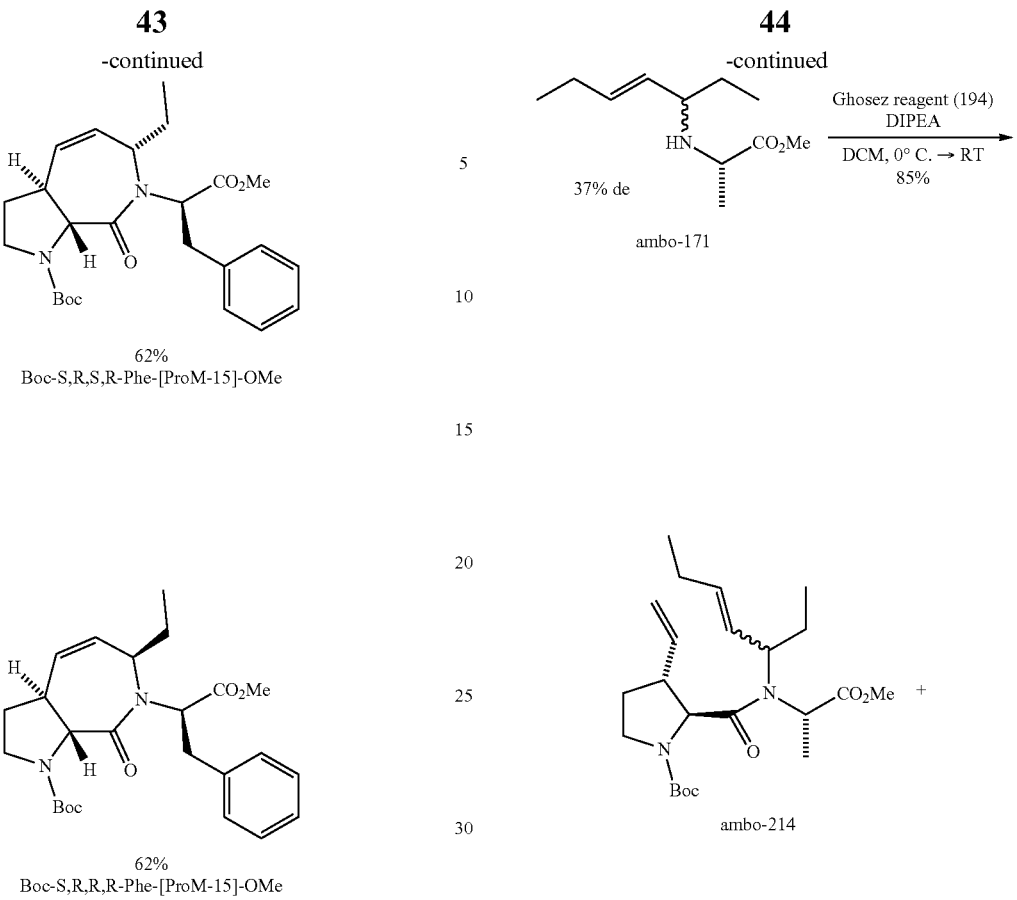

62%
Boc-S,R,S,R-Phe-[ProM-15]-OMe

62%
Boc-S,R,R,R-Phe-[ProM-15]-OMe

Under the metathesis conditions previously developed for the Gly-[ProM-15] derivative, all four diastereomers of Phe-[ProM-15] were prepared in moderate to good yields by using 6 mol % ruthenium catalyst 210 in hexafluorobenzene at 70° C.

For all four diastereomers it was possible to grow single crystals of sufficient quality to confirm the relative configuration of the stereocenters by X-ray crystal structure analysis (FIG. 12).

Synthesis of the Dipeptide Mimetic Boc-R,S,R,S-Ala-[ProM-15]-OMe

Because the coupling of rac-3 with the L-alanine-based allylamine ambo-171 was initially not possible under "HATU conditions", the coupling was then tested using the newly developed methodology (Scheme 19).

Scheme 19: Peptide coupling of racemic Zaminer's acid (rac-3) with the diastereomer mixture ambo-171.

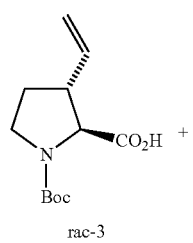

rac-3

In fact, the synthesis of the dipeptic compounds ambo-214 and ambo-dia-214 was also successful here in a very good yield of 85%. The ratio of the four diastereomers could not be determined at this point, but a partial separation of the stereoisomers was observed by thin-layer and column chromatography (3 spots). However, it was initially not possible to identify the separable pair of diastereomers. For this reason, the racemic Zaminer's acid (rac-3) was reacted individually with the two diastereomerically pure allylamines 171 and dia-171, respectively, which are accessible via the Pd-catalyzed allylic amination in a targeted manner (Scheme 20).

In the case of the R,S-configured allylamine 171, a good column chromatographic separation of the resulting diastereomers 214-a and dia-214-b was achieved, whereas the products of the coupling of rac-3 with the S,S-allylamine dia-171 could not be separated.

Scheme 20: peptide coupling of racemic Zaminer's acid (rac-3) with the R,S-configured allylamine 171 (top); and with the S,S-configured allylamine dia-171 (bottom).
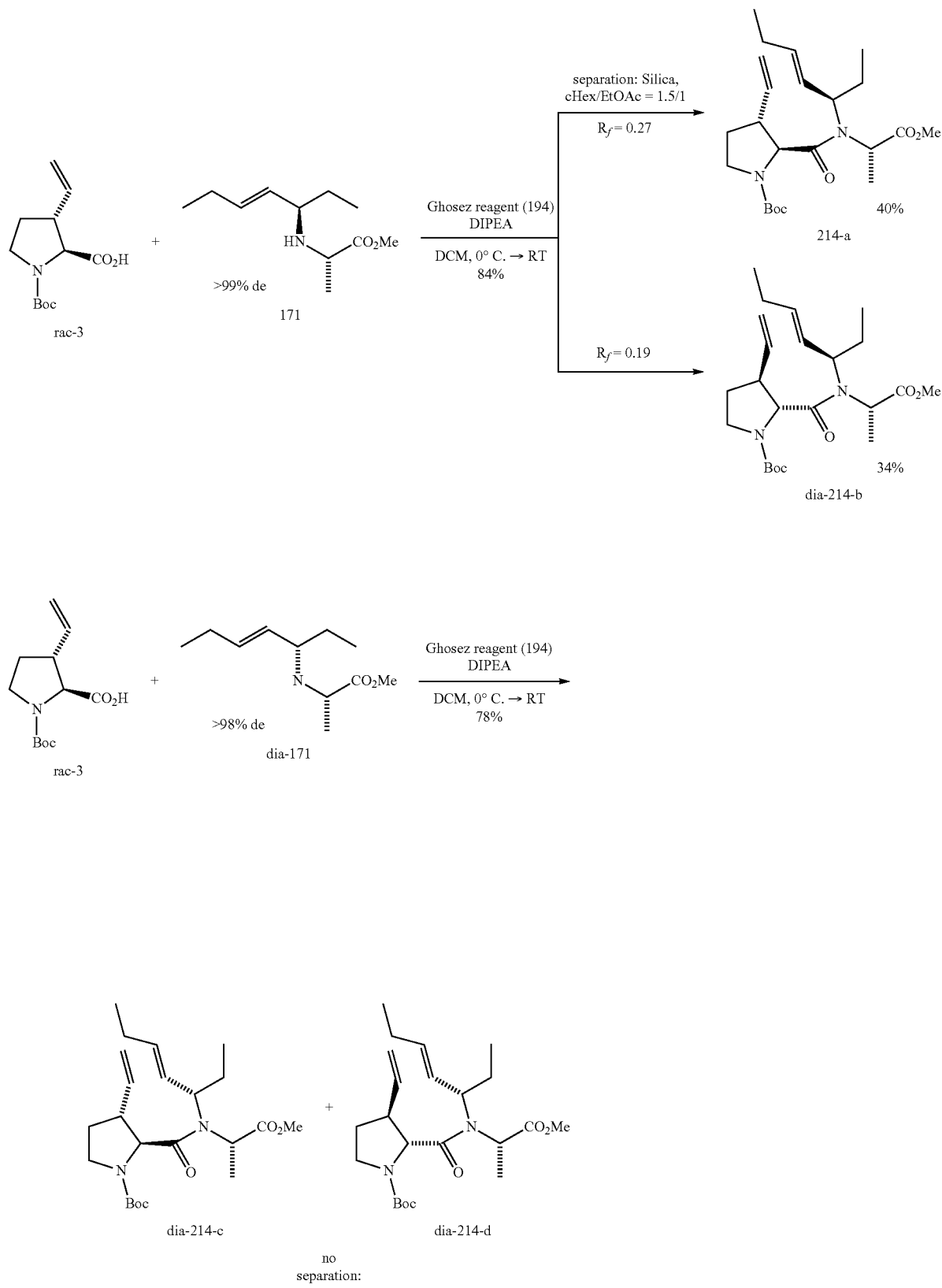

The compound dia-214-b was the only one of the four diastereomers that was a colorless solid instead of a colorless, viscous oil. After crystallization of dia-214-b, the relative configurations of the stereocenters of 214-a and dia-214-b could then be identified by X-ray crystal structure analysis (FIG. 13).

This lucky coincidence opened up the possibility of synthesizing another ProM-15 derivative with the correct relative configuration of the stereocenters. Ring-closing metathesis of dipeptide 214-a under the established conditions with Hoveyda II catalyst in HFB at 70° C. yielded the desired target structure Boc-R,S,R,S-Ala-[ProM-15]-OMe after purification by column chromatography in a yield of 61% (Scheme 21).

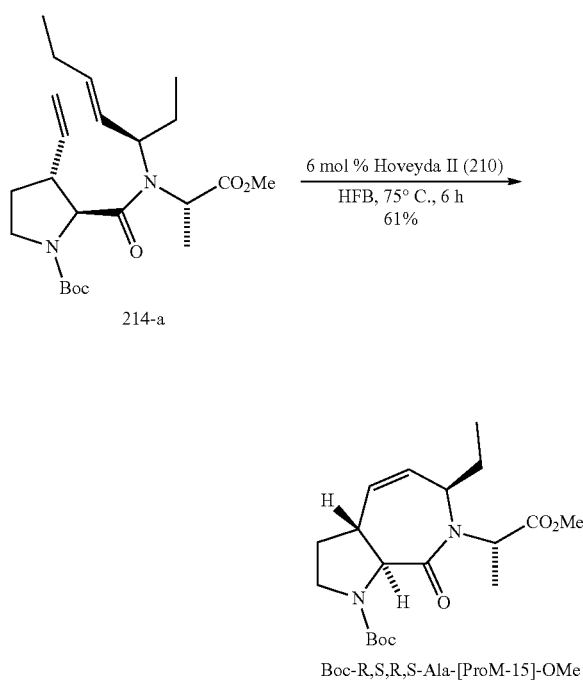

Scheme 21: RCM of dipeptide 214-a using Hoveyda II catalyst (210) in hexafluorobenzene (HFB).

Finally, it was also possible to crystallize the final compound and to confirm the relative configuration by X-ray crystal structure analysis (FIG. 14).

Synthesis of the Dipeptide Mimetic ProM-2

Preparation of Fmoc-[ProM-2]-OH

In the course of the intended development of a ligand synthesis in the liquid phase, larger quantities of the ProM-2 scaffold were required. The synthesis of the Fmoc-[ProM-2]-OH known from the literature was basically carried out according to the known procedures.

To build up the dipeptide structure ambo-27, the two building blocks 26 and dia-4 were coupled with HATU and DIPEA in NMP at 85° C. under conditions known from the literature. The cyclization of the spiro building block ambo-27 by ring-closing metathesis has required large amounts of Grubbs II catalyst (30 mol %) in the past. An increase in yield up to 75% with a simultaneous reduction of the amount of catalyst up to 50% could be achieved when the reaction was carried out in refluxing THF and also copper (I) iodide (CuI) was added in catalytic amounts (Scheme 22).

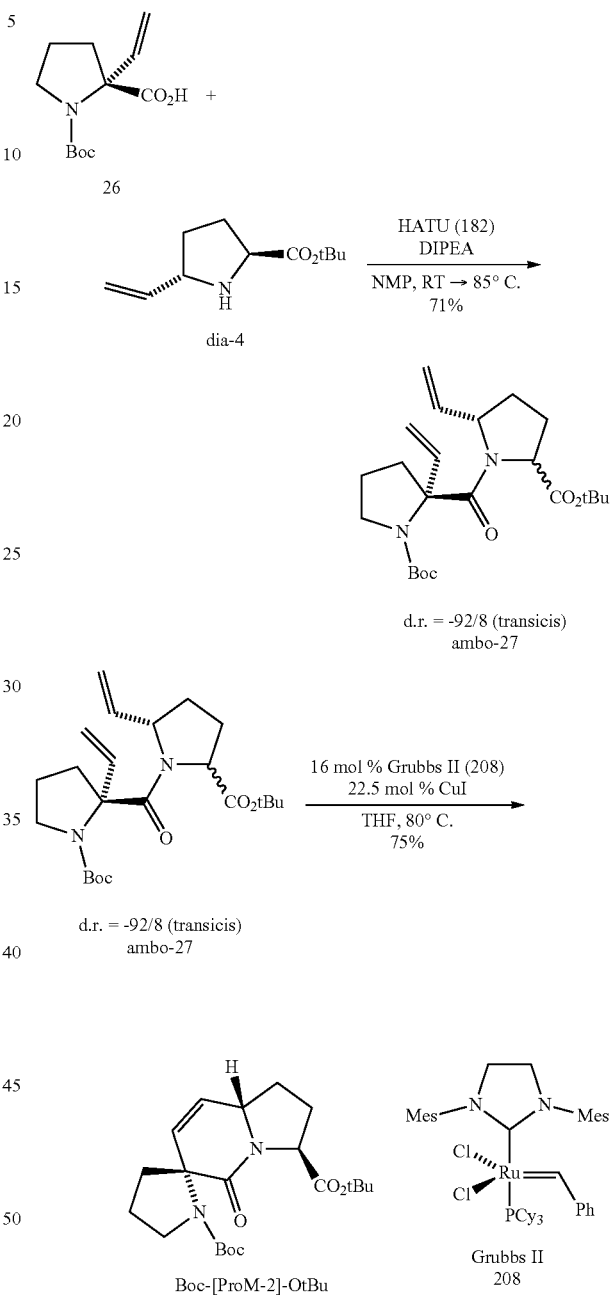

Scheme 22: Grubbs II (208)-mediated ring-closing metathesis of the spiro-dipeptide ambo-27 with the addition of catalytic amounts of CuI.

The final manipulation of the protecting groups for the preparation of Fmoc-[ProM-2]-OH has already given good yields of 80-90%. In cooperation with Reuter, however, it was possible to increase it even further by carrying out the N-terminal Fmoc protection not only in saturated, but by adding more solid $NaHCO_3$ in supersaturated aqueous $NaHCO_3$ solution. After global acidic deprotection with TFA, basic Fmoc protection and subsequent column chromatographic purification of the crude product using a Reveleris flash column chromatography system (DCM/MeOH), the targeted mimic Fmoc-[ProM-2]-OH could be isolated in almost quantitative yield (Scheme 23).

Scheme 4.23: Final protecting group manipulation for the formation of Fmoc-[ProM-2]-OH

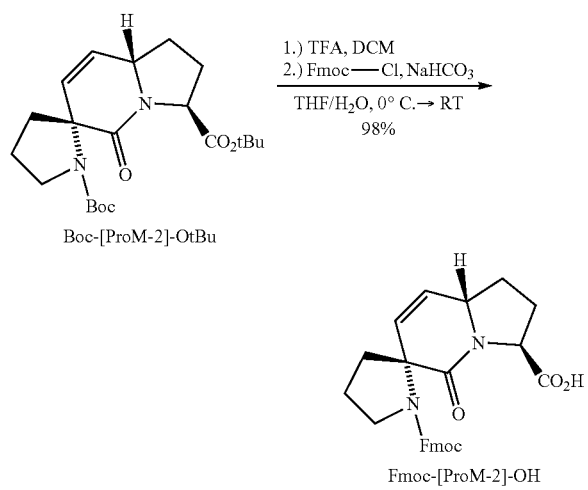

Preparation of Boc-[ProM-2]-OH

To optimize the ligand synthesis developed in this work in the liquid phase, there was a demand for an N-terminal Boc-instead of Fmoc-protected version of the free acid of ProM-2. However, first attempts to synthesize this compound starting from Boc-[ProM-2]-OtBu, using a strategy similar to that used for the preparation of the Fmoc derivative, did not yield satisfactory results. For this reason, an approach to form the methyl esterified dipeptide 233 was developed (Scheme 24).

Scheme 24: Synthesis of the methyl esterified spiro dipeptide 233 starting from the spiro acid 26 and the fully protected trans-5-vinylproline building block 22.

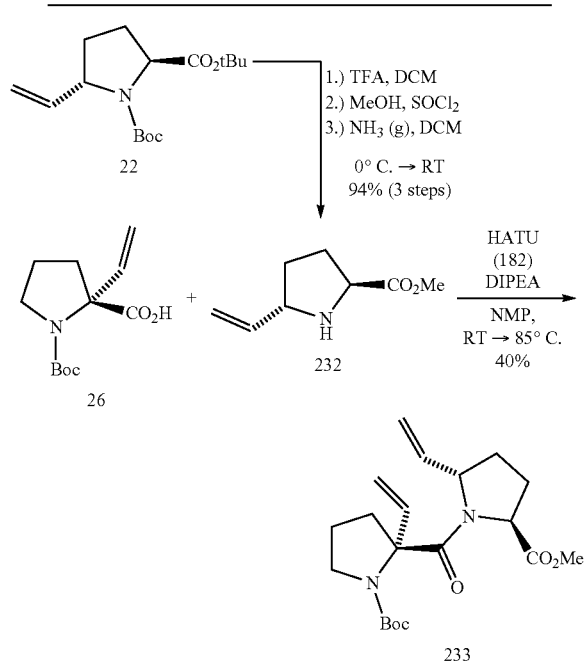

Under similar conditions as before for the tert-butyl ester derivative ambo-27, the cyclization of the spiro building block 233 was carried out by adding Grubbs II (208) and CuI in portions to the reaction mixture. In contrast, however, the solvent hexafluorobenzene (HFB) was used instead of toluene (Scheme 25), as this change in the synthesis of ProM-15 resulted in significantly improved metathesis results.

Scheme 25: Grubbs II (208)-mediated RCM of the spiro dipeptide 233 with the addition of catalytic amounts of CuI.

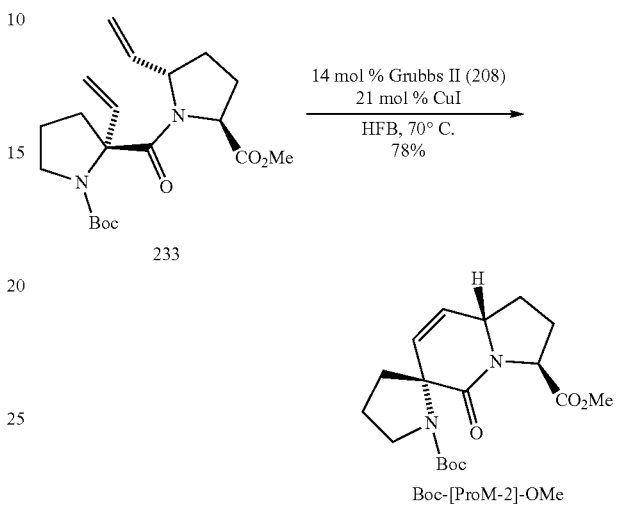

The final saponification of the methyl ester functionality could be carried out without problems and in quantitative yield in an aqueous alkaline medium (Scheme 26).

Scheme 26: saponification of the methyl ester of Boc[ProM-2]-OMe.

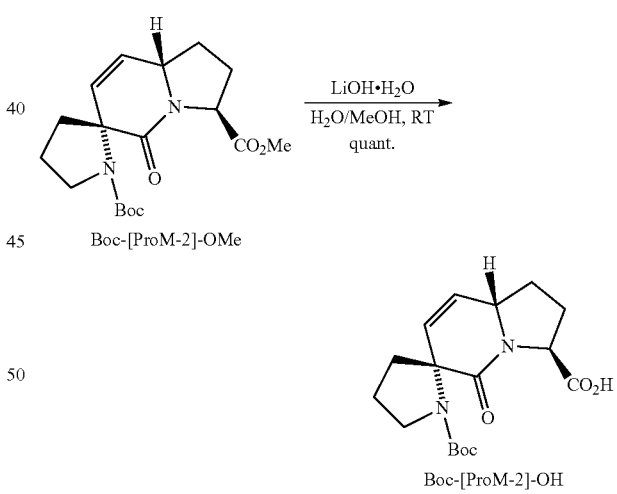

Ligand Synthesis in the Liquid Phase

Development of the Coupling Methodology-"Fmoc Route"

After the developed ProM-based Ena/VASP-EVH1 inhibitor delivered convincing and remarkable biological results in in vitro studies, it was planned to examine its properties in vivo. For this reason, large amounts of substance (>2 g) of the peptide ligand 113 were required. The known building blocks Fmoc-[ProM-1]-OH, Fmoc-[ProM-2]-OH and the commercially available L-2-chloro-phenyl-alanine (L-2Cl-F) had to be used in order to develop an efficient synthesis of the ligand in the liquid phase and to provide sufficient amounts of the inhibitor 113 (Scheme 27).

Scheme 27: Top: Retrosynthetic disassembly of ligand 113. Bottom: Peptide coupling strategy.
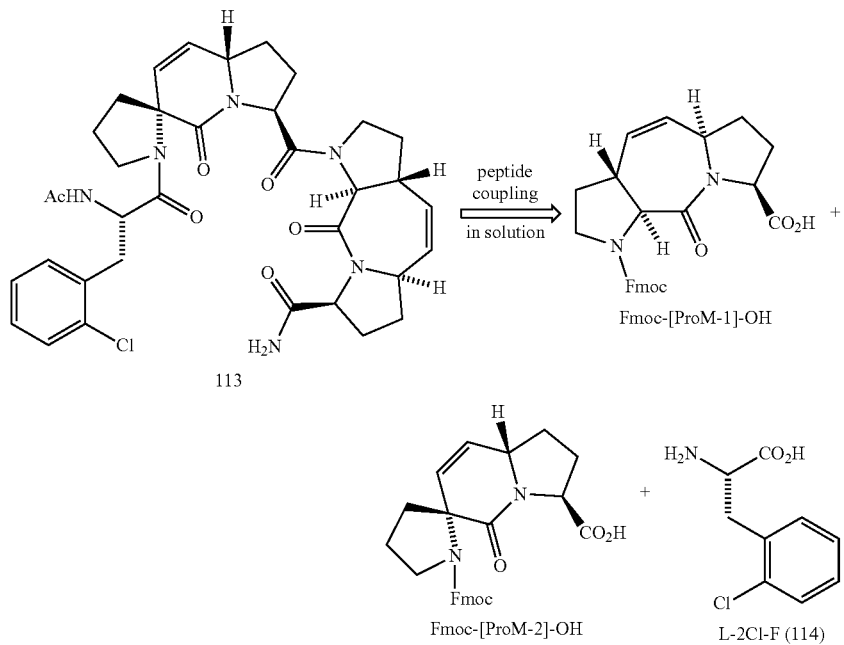
Coupling strategy of Dai et al.:[161]
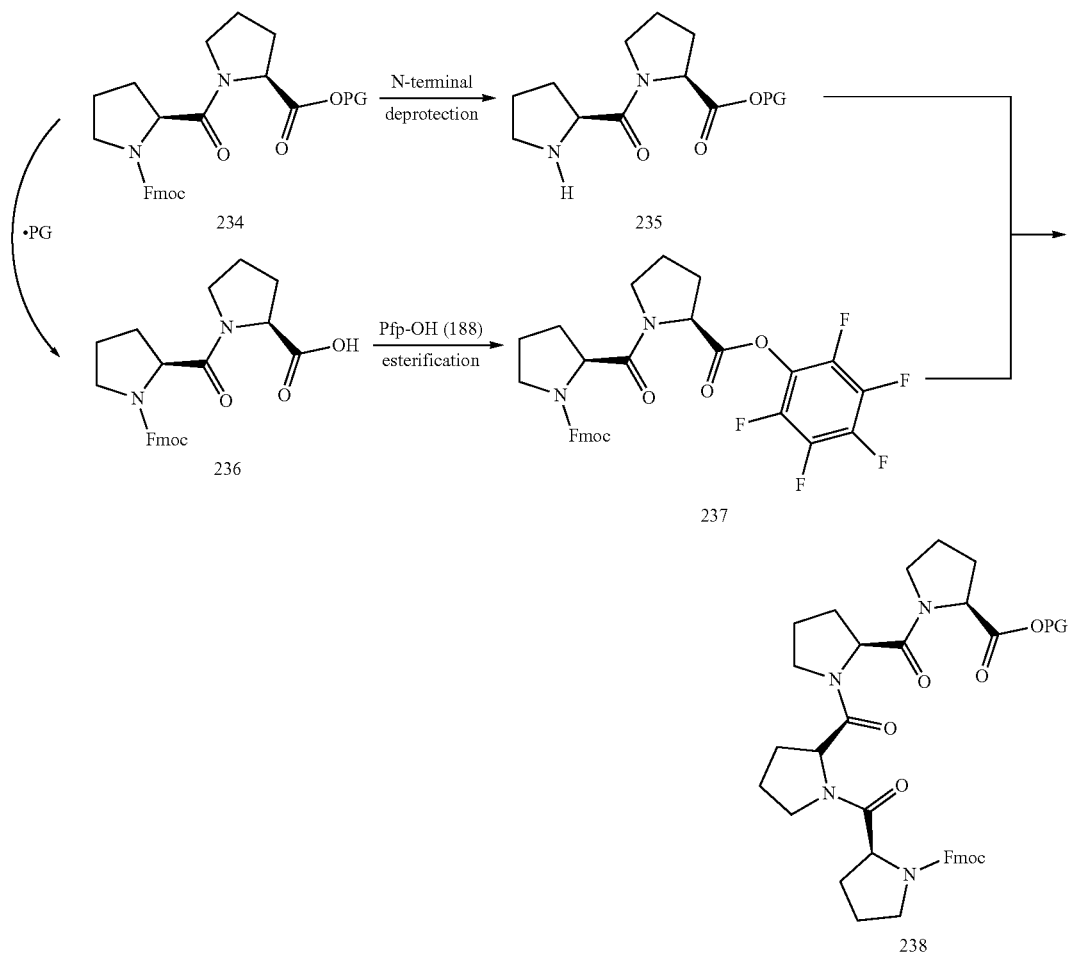

Following this strategy, it made sense to build up the ligand from the C terminus, as in solid phase peptide synthesis. For this purpose, the ProM-1 scaffold was first protected at the C-terminus by converting it into the methyl-esterified building block Fmoc-[ProM-1]-OMe (Scheme 28).

Scheme 28: Methyl esterification of Fmoc-[ProM-1]-OH using TMS-diazomethane.

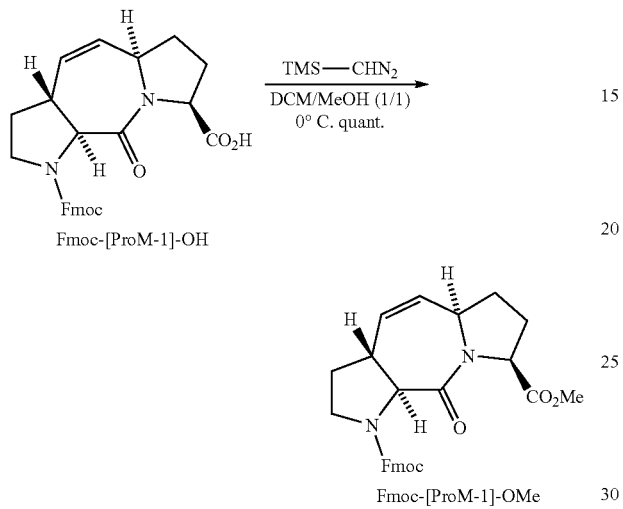

After the individual ligand building blocks could be provided in good yields and on a multi-gram scale, the two ProM scaffolds were then linked according to the methodology described by Dai et al. (Scheme 29).

Scheme 29: N-terminal deprotection of Fmoc-[ProM-1]-OMe with piperidine and subsequent peptide coupling of the free amine NH-[ProM-1]-OMe with Fmoc-[ProM-2]-OPfp for the synthesis of the tetrapeptide 241.

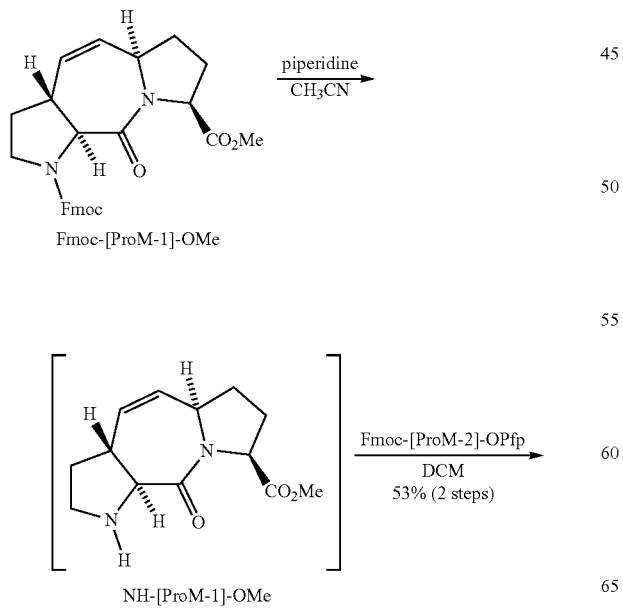

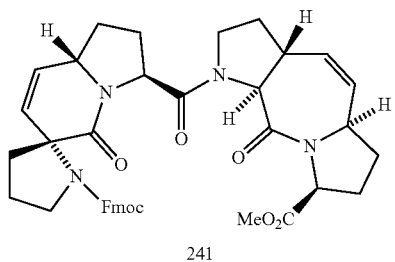

The final coupling to build up the peptide ligand ambo-242 was carried out using an identical procedure (Scheme 30).

Scheme 30: Final peptide coupling for building up the peptide ligand ambo-242.

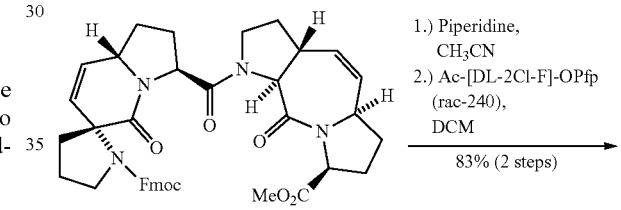

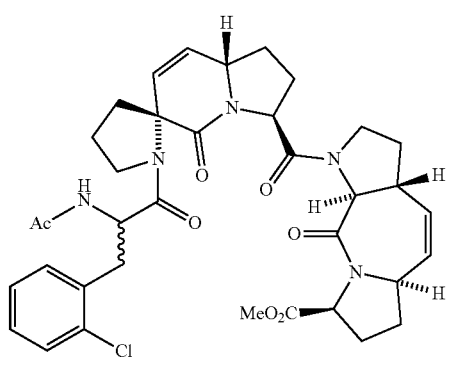

The final conversion of the methyl ester ambo-242 into the amide ambo-113 was achieved in two steps and with an overall yield of 77% (Scheme 31).

Scheme 31: Synthesis of the amide ambo-113 by saponification of the methyl ester ambo-242 and subsequent amidation of the free acid ambo-43.

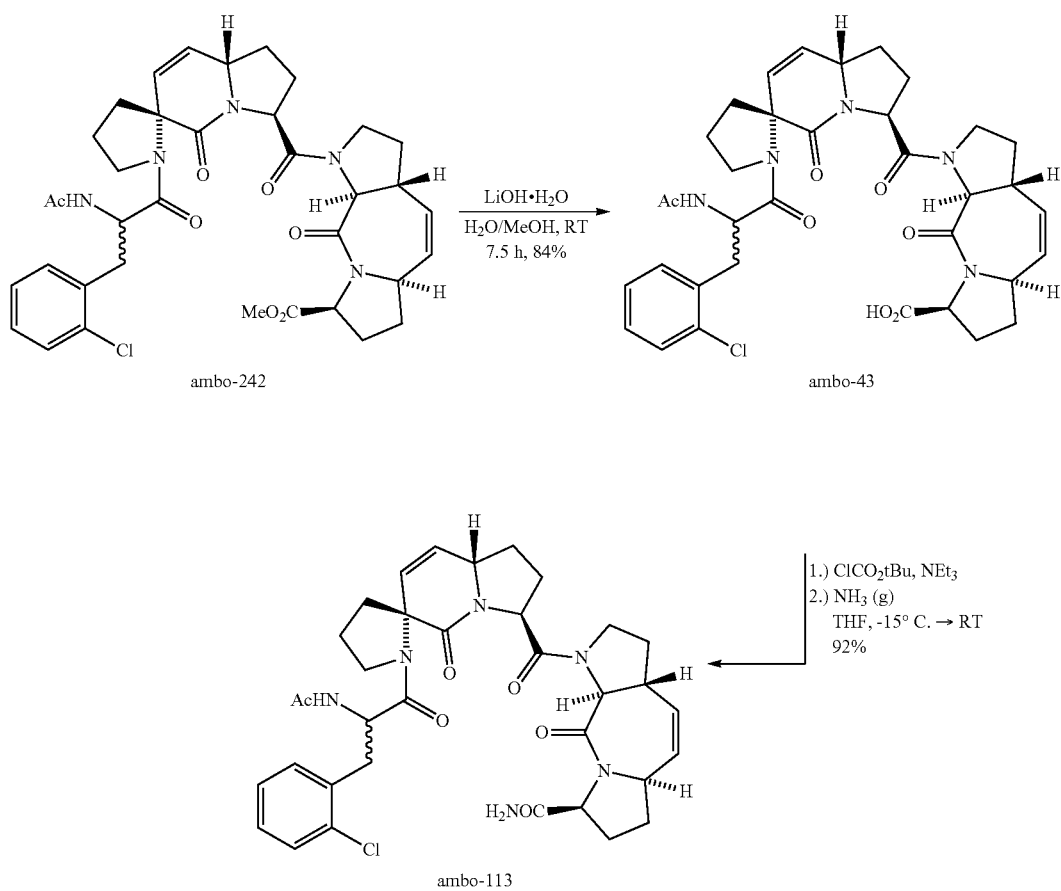

In summary, it was possible for the first time to link the ProM building blocks in the liquid phase and thus to realize the synthesis of the Ena/VASP-EVH1 inhibitor ambo-113 on a preparative scale.

Optimization of the Coupling Conditions-"Boc Route"

Although the developed methodology provides efficient access to the Ena/VASP-EVH1 inhibitors Ac-[L-2Cl-F]-[ProM-2]-[ProM-1]-OMe/OH/NH$_2$ ambo-242, ambo-43 and ambo-113, respectively, there were various reasons for optimizing the coupling sequence. An attempt was therefore made to develop a coupling sequence that was as base-free as possible without deviating too much from the actual strategy of the Pfp ester. To this end, a "simple" N-terminal change of protecting group from fluorenylmethoxycarbonyl (Fmoc), cleavable under basic conditions, to tert-butyloxycarbonyl (Boc), removable under acidic conditions, seemed appropriate. The linkage of the ProM scaffolds could subsequently be implemented using a strategy based on the "Fmoc route" (Scheme 32).

Scheme 32: N-terminal acidic deprotection of Boc-[ProM-1]-OMe with TFA, deprotonaion of the resulting ammonium cation with solid Na$_2$CO$_3$ and final linkage of the ProM building blocks.

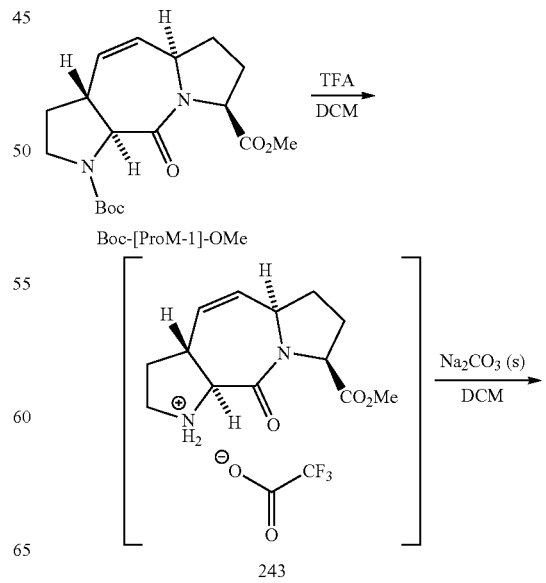

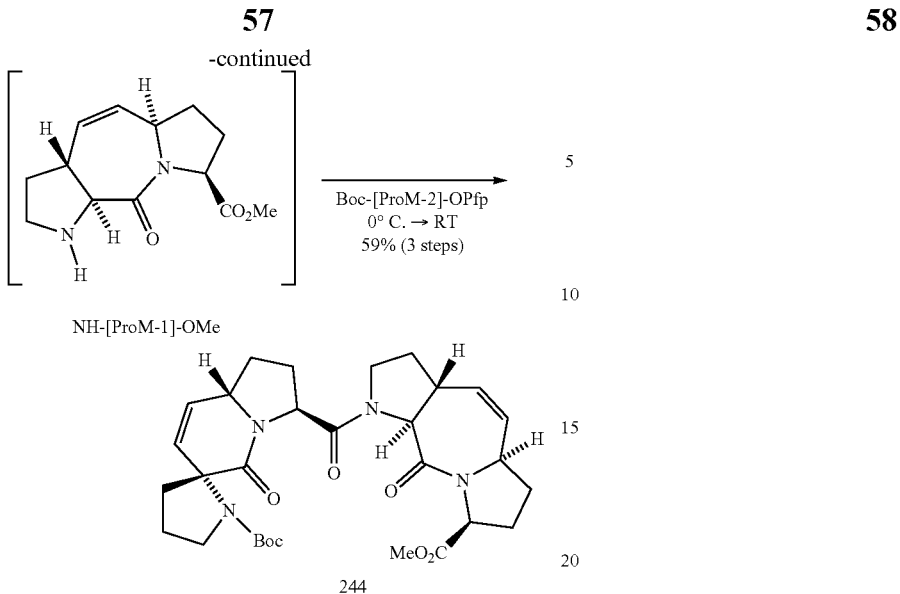

In addition, an epimerization-free access to Ac-[L-2Cl-F]-[ProM-2]-[ProM-1]-OMe was made possible. The methodology developed was followed accordingly at this point (Scheme 33).
Followed Accordingly (Scheme 4.60).

Scheme 33: Final peptide coupling for building up the diastereomerically pure peptide ligand 242 by linking the tetrapeptide 244 with Fmoc-[L-2Cl-F]-OH and subsequent change of protecting groups.

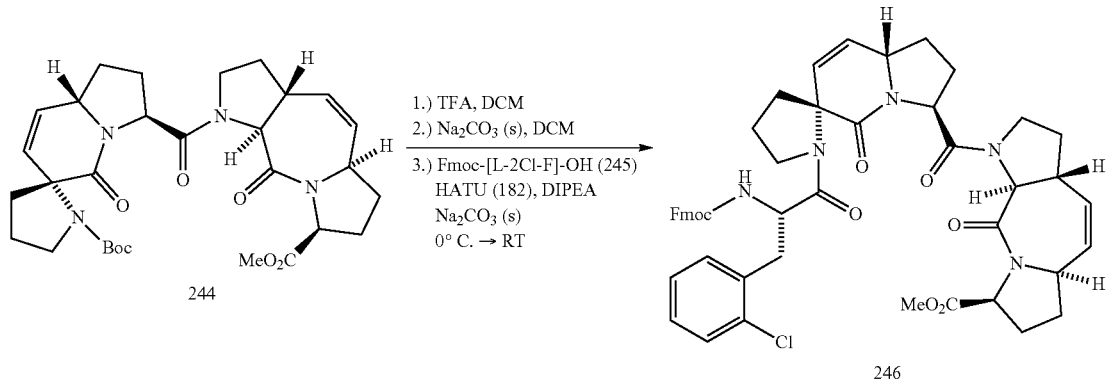

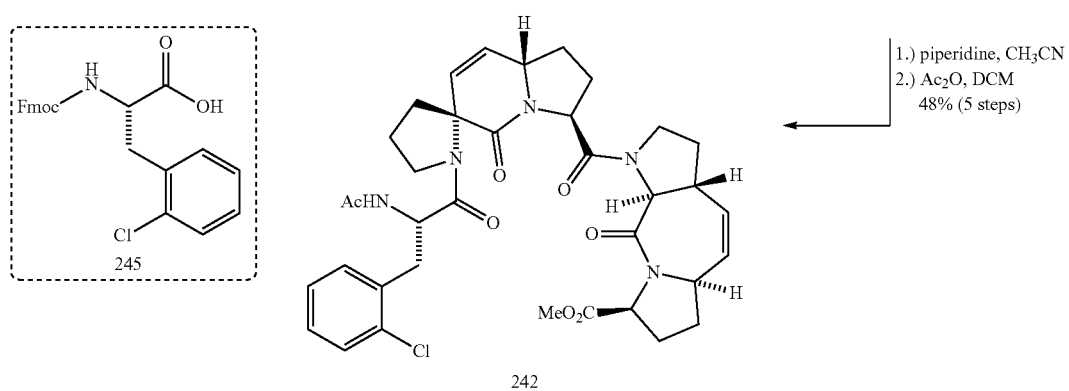

Synthesis of ProM-15 Containing Ligands

After the development of an efficient ligand synthesis in the liquid phase, it was finally also necessary to synthesize ProM-15-containing peptide ligands and to evaluate their binding affinity to the EVH1 domain. As already explained in detail in Chapter 3, it was planned to use the ProM-15 building block as a replacement for the ProM-1 scaffold used up to now. Initially, the glycine derivative of ProM-15 was deliberately chosen in order to exclude the influence of a further substituent on the binding affinity and to be able to make an optimal comparison with the ProM-1 or ProM-9-containing ligands (Scheme 34).

Scheme 34: Restrosynthetic considerations for building up the ProM-15-containing ligand 247.

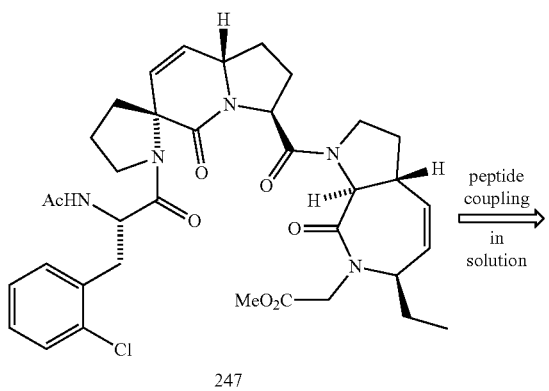

247

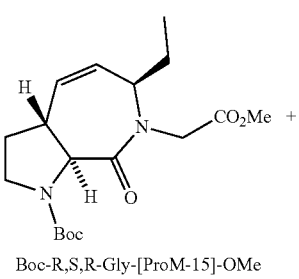

Boc-R,S,R-Gly-[ProM-15]-OMe

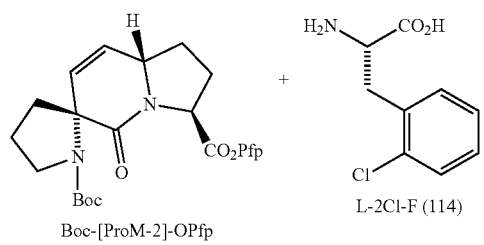
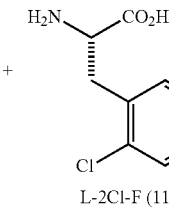
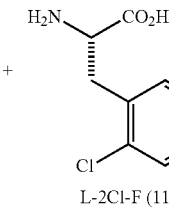

Boc-[ProM-2]-OPfp      L-2Cl-F (114)

The resulting target structure Ac-[L-2Cl-F]-[ProM-2]-[R,S,R-Gly-ProM-15]-OMe (247) was first created by linking the two ProM scaffolds (Scheme 35).

Scheme 35:
Linking the ProM scaffolds to build the tetrapeptide 248 under established conditions.

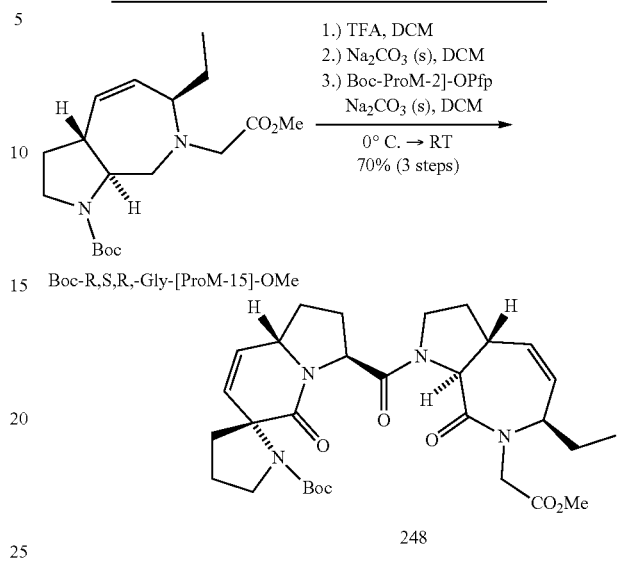

Boc-R,S,R,-Gly-[ProM-15]-OMe

248

The desired tetrapeptide 248 could be prepared without complications under the established conditions and, after purification by column chromatography, isolated as a white solid in a yield of 70% over 3 steps. At this point, too, the double sets of signals visible in the NMR were attributed to the presence of rotamers by H,H-NOESY spectroscopy. In particular, the two signals of the C! proton in the ProM-2 scaffold (4.79 ppm & 4.93 ppm) could be clearly identified as exchange signals.

A diastereomeric purity of the peptide 248 can thus also be assumed here as very likely and again substantiates the assumption that the coupling proceeds free of epimerization under the selected conditions.

The synthesis of ProM-15 ligand 247 coincided in time with the discovery of the 2-chlorophenyl-alanine racemization, at which point it could not be determined whether a prompt solution to this problem could be found. In order to provide material for the intended biological investigations (binding measurements to, and crystallization with the EVH1 domain), wherein the presence of a diastereomeric mixture was of no importance, the tetrapeptide 248 was initially coupled with the racemic active ester rac-240 (Scheme 36).

Scheme 36:
Final peptide coupling to build the peptide ligand ambo-247 by linking the tetrapeptide 248 with racemic
Ac-(L-2Cl—F)—OPfp rac-240).

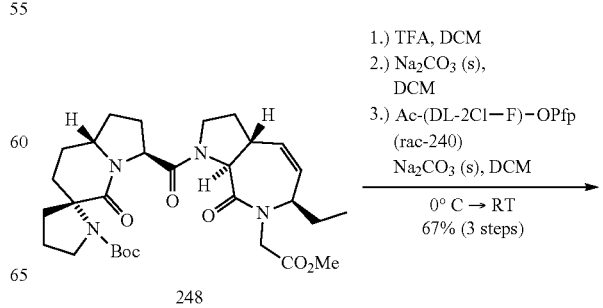

248

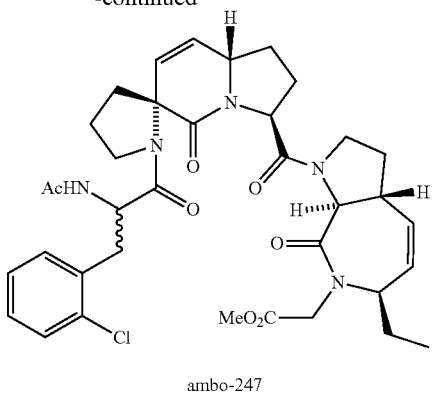

ambo-247

Using the same methodology as for the first coupling step, the final ligand ambo-247 was synthesized as a mixture of diastereomers in a comparable yield of 67% over 3 steps. A diastereomeric ratio could not be determined from the complex NMR spectrum. In addition, the 1H and 13C NMR spectra of ambo-247 and the pure substance 247 synthesized later, as in the case of the ProM-1 ligands ambo-242 and 242, were congruent.

In addition to the methyl ester ambo-247, it was also planned to make the free acid of the compound ambo-249 available for the biological investigations. This saponification was achieved without problems using lithium hydroxide in aqueous-methanolic solution at rt in only 4 h (Scheme 37).

Scheme 37: Saponification of the methyl ester ambo-247 for the synthesis of the free acid ambo-249.

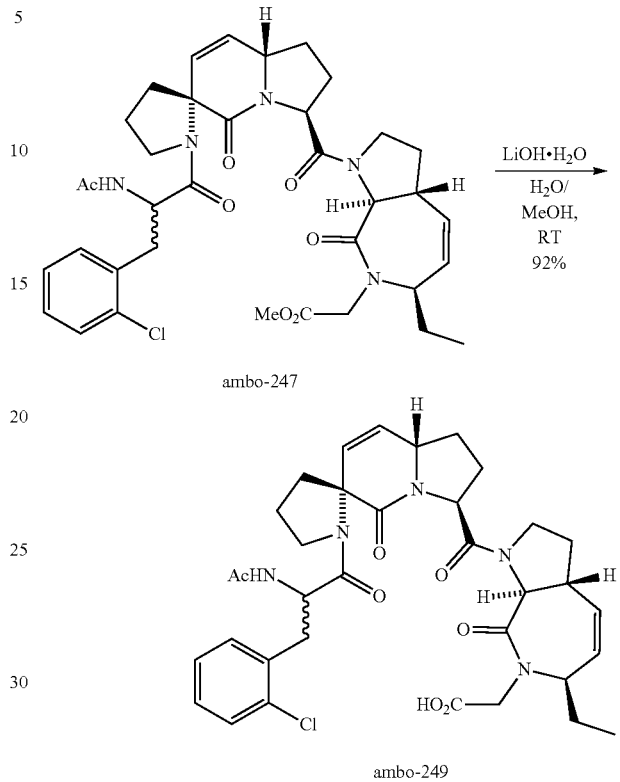

The desired product ambo-249 was obtained in a yield of 92% as an almost white solid which no longer required any further purification. In the end, however, the synthesis of the diastereomerically pure ligand 247 could be realized within the scope of this work (Scheme 38).

Scheme 38: Final peptide coupling to build the diastereomerically pure peptide ligand 247 by linking the tetrapeptide 248 with Fmoc-[L-2Cl—F]—OH (245) and subsequent change of protection groups.

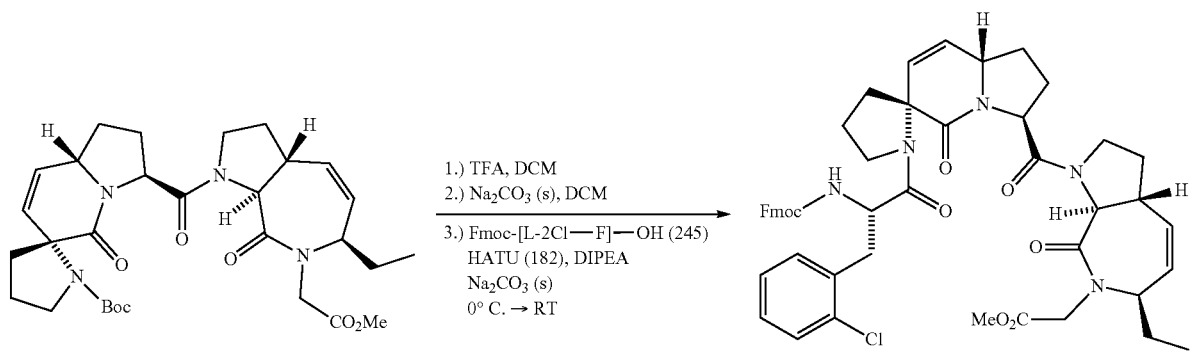

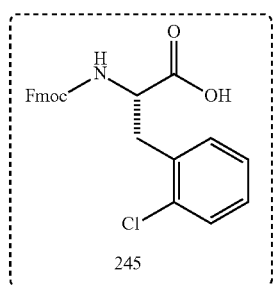

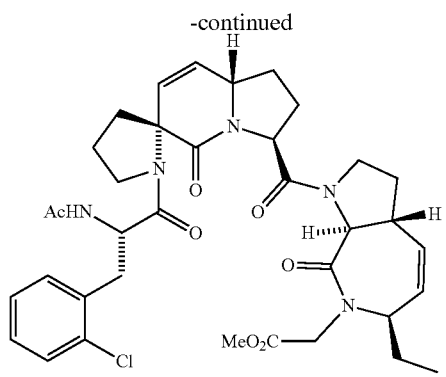

1.) piperidine, CH$_3$CN
2.) Ac$_2$O, DCM
87% (3 steps)

247

As already described for the ProM-1 ligand 242, here also N-terminal deprotection of the tetrapeptide 248 was followed by HATU-mediated coupling with Fmoc-protected L-2-chlorophenylalanine 245. The separation of the resulting urea derivative was also in this case not possible by column chromatography, but it was also not a problem in this case for the subsequent change in protecting group and could ultimately be separated from the final ligand 247 without complications. The final acetylation of the ligand was carried out with acetic anhydride, after which the final target compound of this work, the Ena/VASP-EVH1 inhibitor 247, could be isolated diastereomerically pure in a yield of 87% over 5 steps as a slightly brownish solid. The significantly improved yield compared to the synthesis of ProM-1 ligand 242 (48%) was due to a washing step with acetonitrile.

The Na$_2$CO$_3$ added to the reaction seemed to bind larger amounts of the free amine of the deprotected tetrapeptide 248, which accordingly were no longer available for the coupling. By using acetonitrile this could be prevented and the yield increased significantly. This washing step should consequently be carried out for all couplings in the future in order to minimize possible losses in yield.

Biological Studies

After the successful synthesis of various new Ena/VASP-EVH1 ligands, it was finally necessary to evaluate their binding affinity for the EVH1 domain. Ligand Ac-[L-2Cl-F]-[ProM-2]-[ProM-1]-OEt served as the reference substance.

The binding data of the ligands to the domain was determined by means of isothermal titration calorimetry (ITC) or fluorescence titration (FT) and presented in the form of the dissociation constant (K$_d$) or the free energy (ΔG0). A stronger binding of the ligand to the domain is expressed by a smaller K$_d$ value or a correspondingly more negative ΔG0 value. The relationship between the two parameters is shown in equation (a):

$$K_d = \frac{[\text{ligand}][\text{domain}]}{[\text{complex}]} = e^{\frac{\Delta G^0}{RT}} \quad (a)$$

First binding studies were carried out for the EVH1 ligand 113, which was produced by liquid-phase peptide synthesis within the scope of this work and, compared to the "starting ligand" 44, had an amide function at the C-terminus. It was expected that this change would generate a compound with a similar binding affinity as the ethyl ester 44 used to date, but which could have a higher metabolic stability. Accordingly, it was first necessary to investigate the affinity of the amide derivative 113 for the EVH1 domain (Table 1).

TABLE 1

Binding affinities of various ProM-1-based ligands with respect to the EnaH-EVH1 domain. The dissociation constants (K$_d$) determined by isothermal titration calorimetry (ITC) are stated with the corresponding standard errors in brackets:

| # | Ligand | ITC K$_d$ [µM] |
|---|---|---|
| 1 | Ac-[L-2Cl—F]-[ProM-2]-[ProM-1]-OEt (44) | 7.8 (0.4) |
| 2 | Ac-[L-2Cl—F]-[ProM-2]-[Prom-1]-OMe (242) | 6.8 (0.7) |
| 3 | Ac-[L-2Cl—F]-[ProM-2]-[ProM-1]-NH$_2$ (113) | 7.0 (0.7) |

It was found that the change in the C-terminal masking, as expected in silico, had no influence on the binding affinity. Both the methyl ester 242 obtained first during the liquid-phase peptide synthesis and the final amide derivative 113 produced therefrom had almost identical binding affinities as the ethyl ester 44.

As further investigations also revealed that cell permeabilities, but also the metabolic stabilities of all three derivatives 44, 242 and 113 were almost identical, the decision was made for future work to eliminate the final change in functionalization of the methyl ester 242 forming 113, and as a result, the synthesis sequence was shortened by two steps.

As already explained, computer modeling studies carried out suggested that the ProM-15-based peptide ligand 247, wherein the ProM-1 scaffold was replaced by a ProM-15 building block, could have a significantly higher binding affinity to the EVH1 domain. Due to its pronounced C-terminal flexibility, the ProM-15 derivative 247 should be able to form an additional hydrogen bond and thus provide a gain in affinity. Furthermore, the ProM-15 design was based on the ProM-1-related, but, by introducing an additional methyl group, "structurally optimized" ProM-9 scaffold. With a drastic gain in affinity, it addressed a hydrophobic pocket of the domain, which should also be addressed by the flexible ethyl substituent in ProM-15. In combination with the additional hydrogen bond, a further increase in the binding affinity to the EVH1 domain was expected, which could even exceed that of the already advanced ProM-9-based ligand.

After the successful synthesis of the ProM-15 scaffold and also of the ligand Ac-[L-2Cl-F]-[ProM-2]-[R,S,R-Gly- ProM-15]-OMe (247) these effects postulated in silico could now finally be investigated experimentally.

Table 2 Summarizes the Binding Affinities of the Relevant Ligands.

In fact, by replacing ProM-1 with ProM-15, a remarkable gain in affinity by a factor of 9-10 compared with the ProM-1-based predecessor ligands 44 and 242 could be achieved. The nanomolar $K_d$ value here is, however, in a similar range as for the ProM-9-containing ligand 251, which means that the expected additional gain in affinity was initially not achieved.

TABLE 2

Binding affinities of various ProM-based ligands with respect to the EnaH-EVH1 domain. The dissociation constants ($K_d$) determined by fluorescence titration (FT) and the free energy (ΔG0) are stated with the corresponding standard errors in brackets:

| # | Ligand | FT $K_d$ [µM] | ΔG⁰ [kJ/mol] |
|---|---|---|---|
| 1 | Ac-[L-2Cl—F]-[ProM-2]-[ProM-1]-OEt (44) | 4.1 (0.3) | −30.8 (0.2) |
| 2 | Ac-[L-2Cl—F]-[ProM-2]-[ProM-1]-OMe (242) | 4.4 (0.7) | −30.6 (0.4) |
| 3 | Ac-[L-2Cl—F]-[ProM-2]-[R,S,R-Gly-ProM-15]-OMe (247) | 0.47 (0.03) | −36.1 (0.1) |
| 4 | Ac-[L-2Cl—F]-[ProM-2]-[ProM-9]-OEt (251) | 0.38 (0.05) | −36.6 (0.3) |

The binding affinities of other ProM-based ligands with regard to the EnaH-EVH1 domain were tested. In particular, further derivatives based on the ProM-15, ProM-17 and ProM-21 scaffolds were analyzed. Combinations of ProM-1 or ProM-2 together with ProM-15, ProM-17 or ProM-21 show particularly good affinities with regard to the EnaH-EVH1 domain and have higher affinities for the preferred target than the ProM-2-ProM-1 derivatives of previous generations.

TABLE 3

Binding affinities of other ProM-based ligands with regard to the EnaH-EVH1 domain. The dissociation constants ($K_d$) determined by fluorescence titration (FT) are stated.

| Ligand | $K_D$ |
|---|---|
| Ac-[2Cl-Phe]-[ProM-2]-[ProM-15]-OMe | $K_D$ = 0.47 µM |
| Ac-[2Cl-Phe]-[ProM-1]-[ProM-15]-OMe | $K_D$ = 0.9 µM |
| Ac-[2Cl-Phe]-[ProM-2]-[ProM-17]-OMe | $K_D$ = 0.54 µM |
| Ac-[2Cl-Phe]-[ProM-1]-[ProM-17]-OMe | $K_D$ = 2.2 µM |
| Ac-[2Cl-Phe]-[ProM-2]-[ProM-21]-OMe | $K_D$ = 0.26 µM |
| Ac-[2Cl-Phe]-[ProM-1]-[ProM-21]-OMe | $K_D$ = 2.1 µM |

It was also possible to crystallize Ac-[L-2Cl-F]-[ProM-2]-[R,S,R-Gly-ProM-15]-OMe (247) in a complex with EnaH-EVH1 and to obtain a crystal structure of the ligand domain complex. FIG. 15 shows a superposition of the two ligands 247 and 252 on the protein surface, which allows conclusions to be drawn about the binding situation.

As can be seen on the left in FIG. 15, the ProM-15 ligand 247 binds canonically in the binding groove and the structures of the ligands 247 and 252 are almost identical on the surface. Interestingly, however, a clearly different orientation of the C-terminal carbonyl function can be seen (red arrow), which, in the case of the ProM-15 compound 247, is pointing in the direction of the protein surface, whereas in the case of the ProM-9 ligand 252 it is oriented away from it.

The picture on the right shows a more detailed view of ProM-15 and ProM-9. Surprisingly, the ethyl group of ProM 15 points along the pyrrolidine ring of ProM-9, and not, as expected, in the direction of the PROM 9-methyl substituents (red arrow). ProM-15 reproduces the original proline ring instead of addressing also the hydrophobic pocket addressed by ProM-9. Concluding from these observations, the drastic gain in affinity achieved by the ProM-15 ligand 247 can basically not be attributed to the same effects as with ProM-9, although it is in the same range. Since the hydrophobic region is apparently not addressed by the ethyl substituent, the C-terminus is presumably mainly responsible for the gain in affinity. A closer look at the electron density of ligand 247 in the binding pocket is shown in FIG. 16.

The shape of the electron density around the C-terminal carbonyl oxygen suggests that the carbonyl function in the orientation shown rests on the epitope and points accordingly to the nitrogen atom of the tryptophan 23 (Trp23) below. Measurements of the distance between the two atoms revealed that the distance between these two functionalities would be optimal for the formation of a hydrogen bond via a water molecule, which would also correspond to the gain in affinity. Last but not least, the in silico design of ProM-15 with its greater C-terminal flexibility led to speculation on the formation of such a hydrogen bond, which is why it has been assumed to date that this interaction is responsible for the drastic gain in affinity. At the time of the completion of this work it had not been possible to completely solve the crystal structure, but first refinements seem to confirm the presence of a water molecule between Trp23 and the carbonyl function and thus support the postulated conjecture. Detailed evaluations are in progress and should be communicated as soon as possible.

In terms of the conceptual idea, the ProM-15 building block seems to represent the most promising structural optimization of the ProM-1 initial scaffold to date. Although the in silico predicted addressing of the hydrophobic binding pocket by the ethyl substituent did not occur, it was probably possible for the first time to form an additional hydrogen bond with the domain due to the increased C-terminal flexibility. This resulted in a significant gain in affinity by a factor of 9-10 and a ligand binding in the (higher) nanomolar range 247. Due to the simple modular structure of ProM-15, the newly developed palladium-catalyzed allylic amination should allow a simple modification of the ethyl substituent and thus also enable addressing the previously unaddressed hydrophobic binding pocket. In this way, the originally targeted combination of binding effects could still be achieved and a further gain in affinity for the EVH1 domain could be generated.

SUMMARY

Polyproline type-2 helix (PPII helix) mediated protein-protein interactions between so-called proline-rich motifs (PRMs) and the corresponding binding domains (PBDs) play a significant role in many essential biological processes, which is why their modulation of great scientific and pharmacological interest. In this context, the inventors developed rationally designed, modularly structured diproline analogs in PPII conformation (ProMs), whose use as a Pro-Pro equivalent in the core motif of a PRM enabled the targeted inhibition of the above-mentioned interactions. The present work contributes to the optimization of the highly selective Ena/VASP-EVH1 inhibitor 43 resulting from these studies (Scheme 39).

Scheme 39: Structural development of the Ena/VASP-EVH1 inhibitor 43.

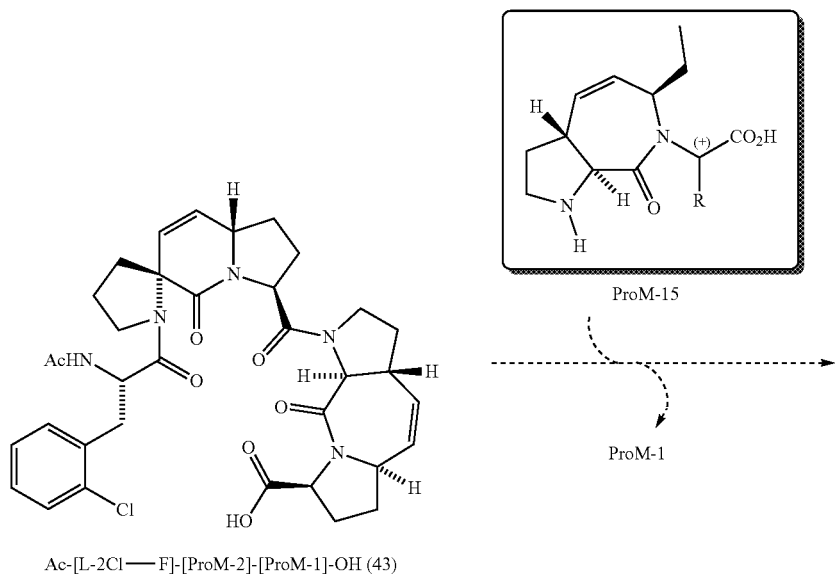

Ac-[L-2Cl——F]-[ProM-2]-[ProM-1]-OH (43)

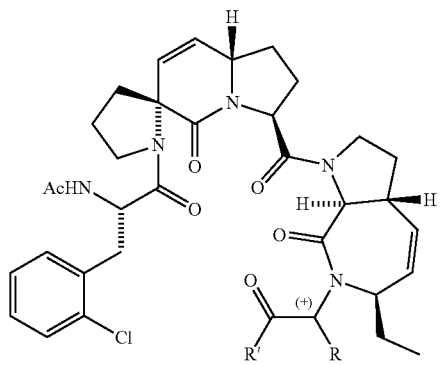

Ac-[L-2Cl——F]-[ProM-2]-[ProM-15]-R' (115)

The substitution of the ProM-1 scaffold by the bicyclic structure ProM-15 should lead to a peptide mimetic 115 that is significantly more flexible at the C-terminus, which could form additional hydrophobic and hydrophilic interactions with the EVH1 domain and thus have a significantly increased binding affinity to it. In addition to the greater flexibility, the in silico designed ProM-15 building block offers another variable interaction site "R", via which interactions with the domain are also possible, but which also represents an option for addressing new PBDs.

Following an established, tried and tested synthetic strategy for building ProM building blocks, ProM-15 could be derived from the already known acid building block 3 and the so far little researched allylamines 112 by ring-closing metathesis and peptide coupling (Scheme 40).

Scheme 40:
Retrosynthetic considerations for building the ProM-15 scaffold.

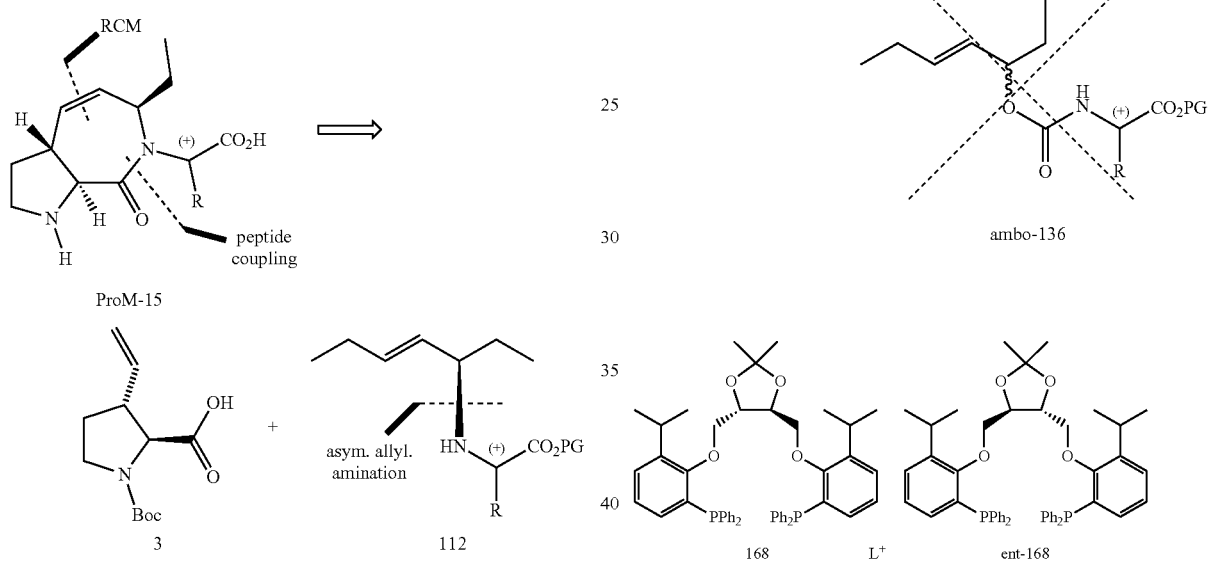

Palladium-Catalyzed Asymmetric Allylic Aminations

The stereoselective synthesis of N-allylated amino acid esters of type 112 was accordingly a challenge and the essential prerequisite for the provision of ProM-15, which could be successfully achieved through the development of a novel, highly selective, asymmetric allylic amination using the racemic carbonate rac-83 and various α-amino acid esters 110 (Scheme 41).

Scheme 41: Synthesis of allylamines of type 112* or 153* by the palladium-catalyzed asymmetric N-allylation of α-amino acid esters 110 developed in this work. Under the optimized reaction conditions, the formation of carbamate by-products ambo-136 could be completely suppressed.

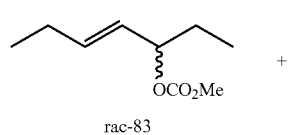

rac-83

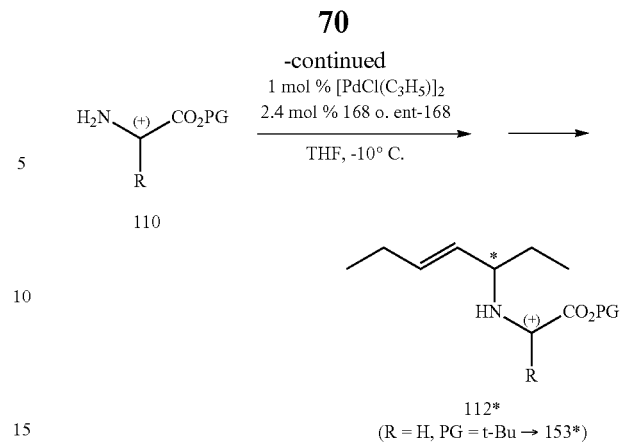

After optimizing the reaction conditions, using only 1 mol % of a palladium source and 2.4 mol % of the chiral bisphosphine ligands 168 or ent-168, the synthesis of a total of 19 (novel) allylamines 112* and their complete characterization was carried out successfully for the first time (FIG. 17). The conditions found made it possible not only to prepare the glycine-based compound 153* in 95% ee, but also to achieve excellent selectivities and good yields when using chiral nucleophiles 110, with the few examples for similar transformations described in the literature being clearly exceeded.

Stereoselective Synthesis of New Dipeptide Mimetics

Starting from the stereoselectively produced allylamines 112*, the synthesis of seven novel ProM-15 scaffolds was subsequently achieved using the established strategy, with the final steps being adapted or optimized to the new system.

Scheme 42 shows an example of the synthesis of the glycine-based ProM-15 with the targeted absolute configuration, as well as the other novel dipeptide analogs:

Scheme 42: Synthesis strategy for building ProM-15 and the structures produced in this work.

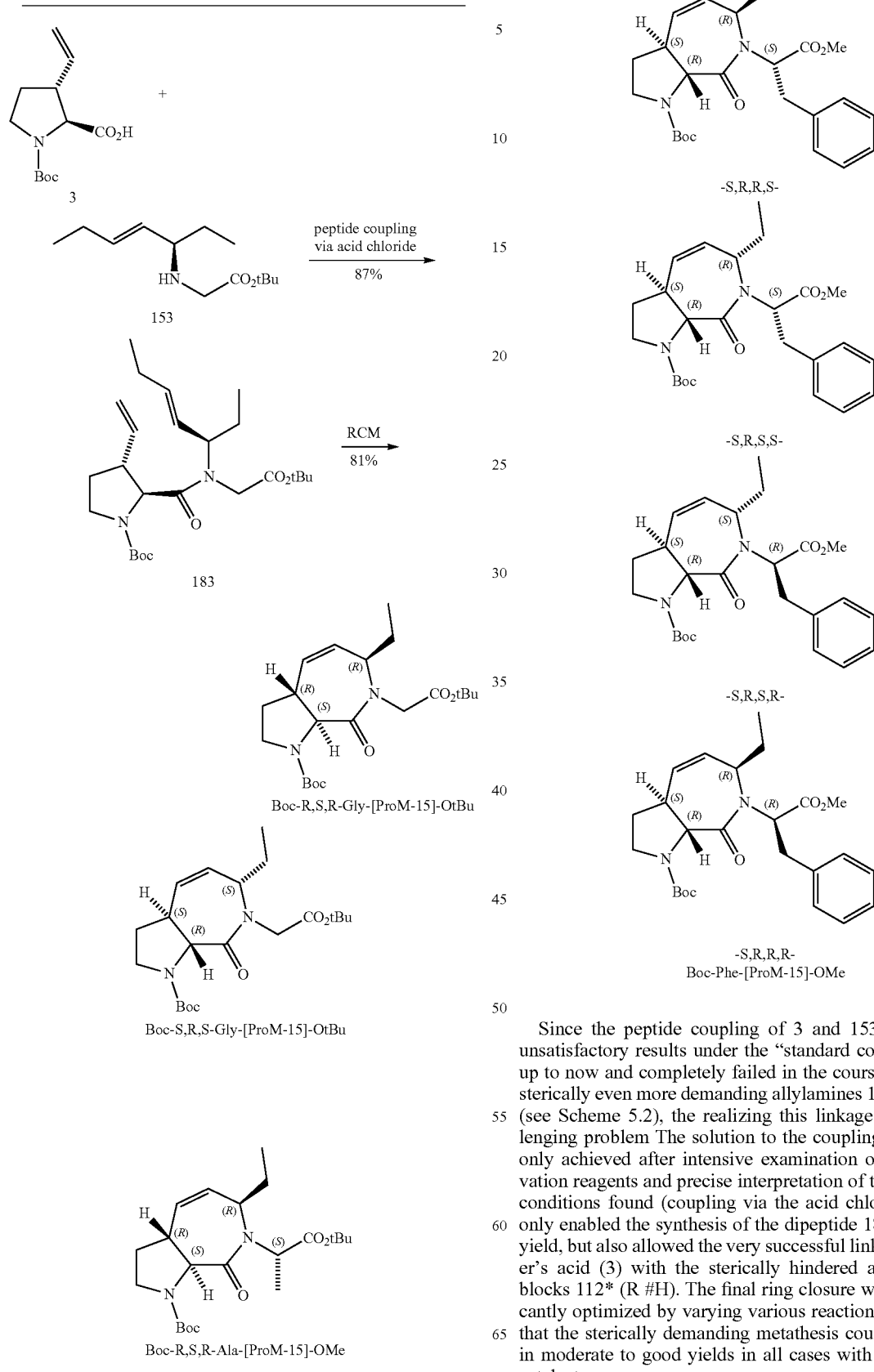

Since the peptide coupling of 3 and 153 only yielded unsatisfactory results under the "standard conditions" used up to now and completely failed in the course of the use of sterically even more demanding allylamines 112* with R #H (see Scheme 5.2), the realizing this linkage posed a challenging problem The solution to the coupling problem was only achieved after intensive examination of various activation reagents and precise interpretation of the results. The conditions found (coupling via the acid chloride of 3) not only enabled the synthesis of the dipeptide 183 in excellent yield, but also allowed the very successful linkage of Zaminer's acid (3) with the sterically hindered amine building blocks 112* (R #H). The final ring closure was also significantly optimized by varying various reaction parameters so that the sterically demanding metathesis could be achieved in moderate to good yields in all cases with only 6 mol % catalyst.

Finally, all newly produced ProM-15 scaffolds could also be crystallized and the relative configuration of the stereocenters verified by X-ray crystal structure analysis.

Ligand Synthesis in the Liquid Phase

In the context of this invention, the synthesis of the final ProM-based PPII peptide mimetics could also be realized in the liquid phase. The interest in such a synthesis route that can be carried out on a multi-gram scale was based on the need to provide large amounts of substance for desired in vivo experiments, which were not accessible via the previously used solid-phase peptide synthesis. Starting from the commercially available L-2-chlorophenylalanine (114) and the already known building blocks Fmoc-[ProM-2]-OH (whose synthesis has also been optimized) and Fmoc-[ProM-1]-OH, an efficient coupling methodology based on pentafluorophenol esters has been developed (Scheme 43).

Scheme 43: Structure of the peptide ligand ambo-113 starting from L-2-chlorophenylalanine (114) and the two ProM scaffolds Fmoc-[ProM-2]-OH and Fmoc-[ProM-1]-OH.

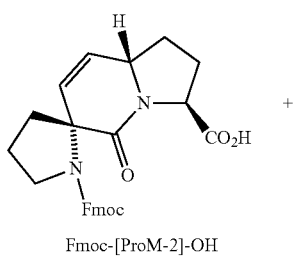

114

+

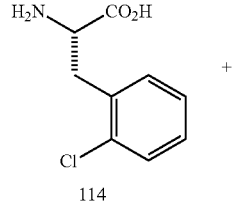

Fmoc-[ProM-2]-OH

+

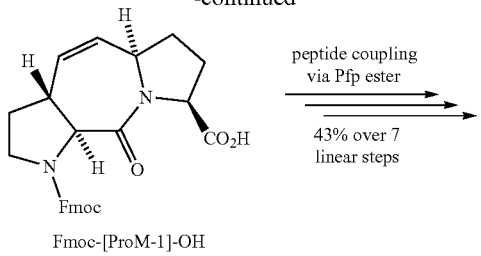

Fmoc-[ProM-1]-OH peptide coupling via Pfp ester

43% over 7 linear steps

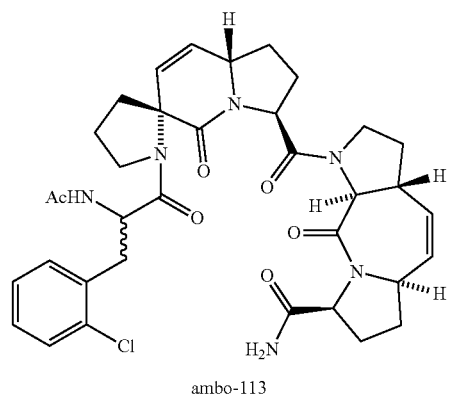

ambo-113

Ligand 113 was built under mild conditions after methyl esterification of the ProM-1 scaffold and provision of the activated coupling partners, starting from the C-terminus, followed by change of 75 functionality. However, the methodology found turned out to be not optimal for several reasons, with the epimerization of the 2-chlorophenylalanine stereocenter being the greatest disadvantage. Nevertheless, with a total yield of 43% over seven linear steps starting from the ProM-1 building block, initially a total of approximately 2.5 g of the peptide ligand ambo-113, as a mixture of diastereomers, could be synthesized and made available for the targeted in vivo experiments.

An initial optimization of the synthesis sequence was then achieved, which included a switch to Boc protective groups and a combination of Pip ester and HATU activation, so that the desired ligand was now accessible in diastereomerically pure form. The improved methodology was then used to prepare a ProM-15-containing ligand 247, the synthesis of which is shown in Scheme 44:

Scheme 44: Synthesis of the ligand Ac-[L-2Cl—F]-[ProM-2]-[R,S,R-Gly-ProM-15]-OMe (247) under optimized coupling conditions.

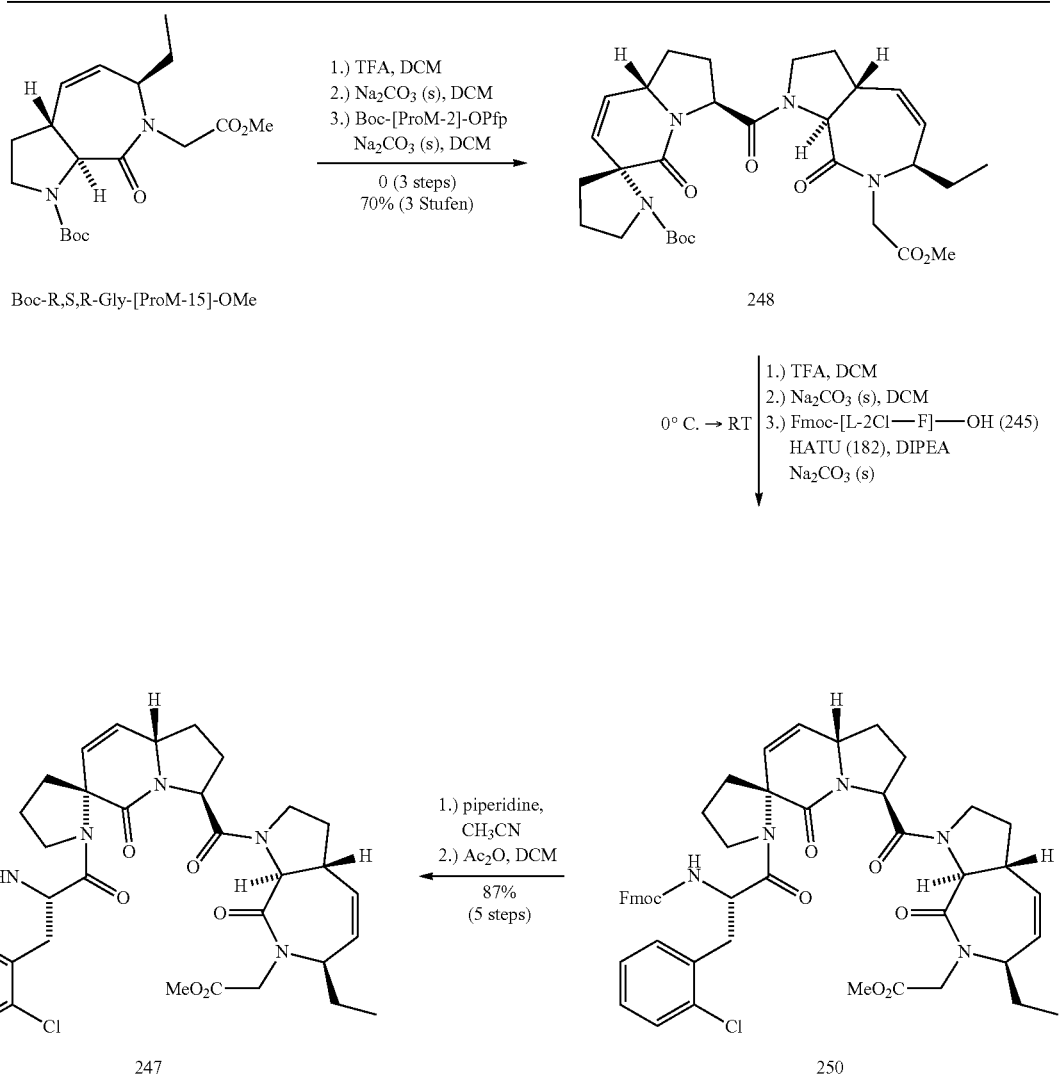

Biological Investigations of the ProM-15-Containing Ligand 247

As already indicated in the introduction to this chapter, the computer modeling studies carried out suggested that a ProM-15-based peptide ligand, due to its pronounced C-terminal flexibility, could have a significantly higher binding affinity to the EVH1 domain than the rigid ProM-1-containing previous version. Furthermore, findings from the ProM-1-related, but "structurally optimized" ProM-9 scaffold were incorporated into the ProM-15 design (Scheme 45).

Scheme 45: Derivation of the ProM-15 scaffold from the known structures ProM-1 and ProM-9.

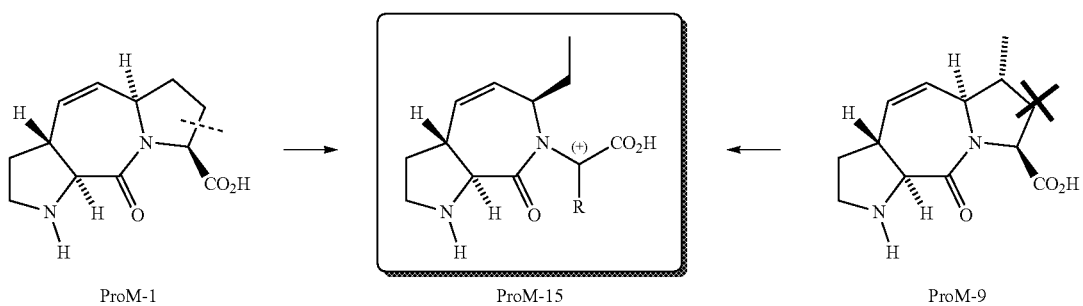

By introducing an additional methyl group, ProM-9 was able to address a hydrophobic pocket in the domain and thus a peptide ligand with an impressively increased binding affinity was created.

The flexible ethyl substituent in ProM-15 should also address this interaction surface and, in combination with an additional newly formed hydrogen bond, lead to a further increase in affinity.

After successfully finding access to ProM-15 and synthesizing the peptide ligand 247, the effects postulated in silico could be experimentally checked in the FMP in Berlin.

The novel compound Ac-[L-2CI-F]-[ProM-2]-[R,S,R-Gly-ProM-15]-OMe (247) showed, compared with the ProM-1-based predecessor ligands 44 and 242, actually had an impressively increased binding affinity for the EVH1 domain by a factor of 9-10 and was thus in the same range as the ProM-9 version 251, which had the best binding to date.

Due to the orientation of the C-terminal carbonyl function, the drastic gain in affinity was attributed to the formation of the desired hydrogen bond, although the second interaction of the ethyl substituent with the hydrophobic pocket of the domain could not be achieved. Although the combination of both effects failed, ProM-15 still seems to represent the most promising structural optimization of the ProM-1 scaffold in terms of the conceptual idea. The formation of the novel hydrogen bond and the resulting significant gain in affinity can initially be regarded as a great success, wherein the palladium-catalyzed allylic amination developed within the scope of this work should allow a derivatization of ProM-15 in a simple manner (Scheme 46).

Scheme 46: A further development of the ProM-15 scaffold could be achieved by branching the ethyl substituent. This derivatization should be accessible in a simple manner by using a slightly modified catalytic substrate rac-83-R'.

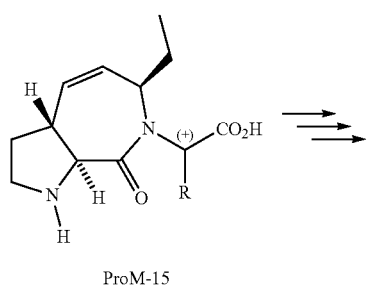

ProM-15

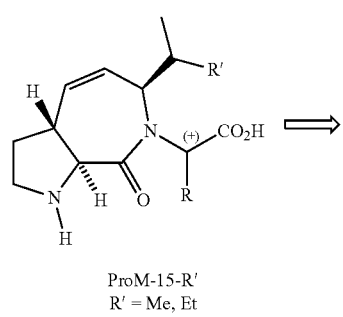

ProM-15-R'
R' = Me, Et

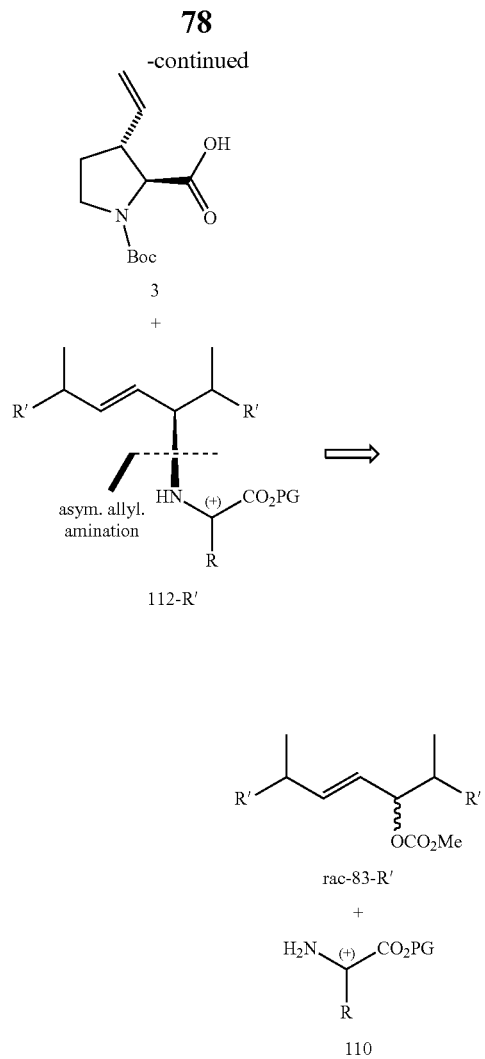

By choosing an appropriately modified catalytic substrate rac-83-R', a targeted introduction of various substituents should be possible. The novel ProM-15-R' derivatives could, for example, carry a branched iso-propyl or iso-butyl group as useful structural proposals, which should make it possible to address the hydrophobic pocket Synthesis of the peptide ligand Ac-[L-2CI-F]-[ProM-2]-[R,S,R-Gly-ProM-15]-OMe (247)

Synthesis of Boc-[ProM-2]-[R,S,R-Gly-ProM-15]-OMe (248)

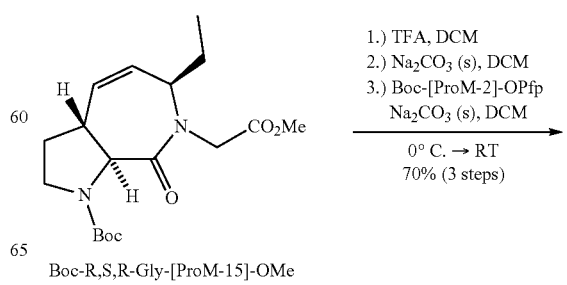

Boc-R,S,R-Gly-[ProM-15]-OMe

1.) TFA, DCM
2.) Na₂CO₃ (s), DCM
3.) Boc-[ProM-2]-OPfp
   Na₂CO₃ (s), DCM

0° C. → RT
70% (3 steps)

-continued

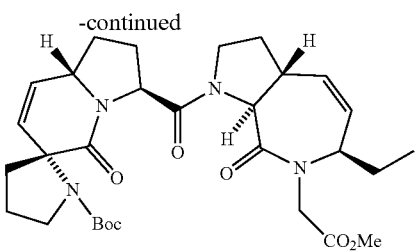

248

Under non-inert conditions, a solution of 220 mg (0.624 mmol, 1 eq.) Boc-R,S,R-Gly-[ProM-15]-OMe in 1.4 ml DCM was treated dropwise at 0° C. with 0.72 ml (9.36 mmol, 15 eq.) TFA. The ice bath was removed, stirred for 1.5 h at rt, then all volatile constituents were removed under reduced pressure, concentrated twice again from DCM and finally dried in vacuo. The residue obtained was taken up in 12.5 ml of DCM, 3 spatulas of solid $Na_2CO_3$ were added (solid material stuck together somewhat) and the mixture was stirred for 5 minutes. It was then filtered, the solvent was removed under reduced pressure and dried in vacuo.

The residue now obtained was taken up in 12.5 ml of abs. DCM under an argon atmosphere, another 3 spatulas of solid $Na_2CO_3$ were added and then 376 mg (0.749 mmol, 1.2 eq.) Boc-[ProM-2]-OPfp were added. After stirring overnight (15 h) at rt, the mixture was filtered and the solvent was removed under reduced pressure. Purification by column chromatography on silica gel (DCM/MeOH=20/1) and drying in vacuo at 60° C. allowed 250 mg (0.438 mmol, 70% over 3 steps) of the desired tetrapeptide 248 to be isolated as a white solid.

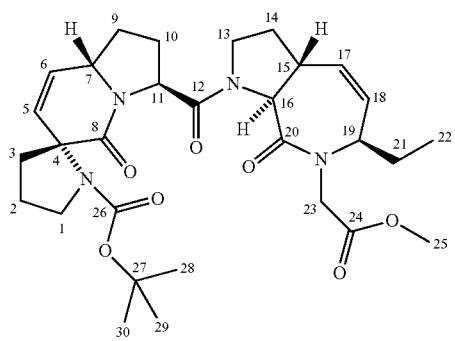

$C_{30}H_{42}N_4O_7$
M: 570.68 g/mol.
TLC: R1=0.22 (silica, DCM/MeOH=20/1), $KMnO_4$ reagent.

1H-NMR (500 MHZ, $CDCl_3$, rotamer mixture 95): 0 [ppm]=1.01 (t, $^3J$=7.2 Hz, 3H, H-22) 1.35, 1.44 (2× s, 9H, H-28/29/30); 1.52-1.63 (m, 1.55H, H-9rot1/21); 1.69-1.82 (m, 2.45H, H-2/9rot2/21'); 1.84-1.93 (m, 2H, H-3/14); 1.95-2.03 (m, 1H, H-2'); 2.12-2.22 (m, 3H, H-9'/10/14'); 2.26-2.31 (m, 1H, H-3'); 2.40-2.46 (m, 1H, H-10'); 2.94-3.03 (m, 1H, H-15); 3.43-3.52 (m, 1H, H-1); 3.56-3.70 (m, 4.45H, H-1'rot2/13/25); 3.73-3.78 (m, 1.55H, H-1'rot1/23); 4.24 (ψ t, J=8.8 Hz, 0.45H, H-13'rot2); 4.30 (ψ t, J=8.7 Hz, 0.55H, H-13'rot1); 4.35-4.39 (m, 1H, H-7); 4.68-4.81 (m, 2.55H, H-11rot1/19/23'); 4.93 (ψ t, J=8.1 Hz, 0.45H H-11rot2); 5.11 (Y t, J=11.9 Hz, 1H, H-16); 5.56-5.59 (m, 1H, H-17); 5.74-5.79 (m, 1.1H, H-5rot1/6rot1); 5.83-5.89 (m, 1.9H, H-5rot2/6rot2/18).

$^{13}C$-NMR (125 MHZ, $CDCl_3$, rotamer mixture 95): δ[ppm]=11.7 (C-22); 22.7, 23.1 (C-2); 26.2, 26.2 (C-21); 28.3 (C-10); 28.5, 28.7 (C-28/29/30); 31.1, 31.1 (C-14); 31.4, 31.5 (C-9); 38.6, 39.8 (C-3); 42.3 (C-15); 43.2 (C-23); 47.6, 47.7 (C-13); 48.1, 48.5 (C-1); 52.1, 52.1 (C-25); 55.4, 55.5 (C-19); 56.3, 56.3 (C-11); 58.9, 59.0 (C-7); 60.3, 60.3 (C-16); 64.1, 64.3 (C-4); 79.5, 79.7 (C-27); 121.9, 123.1 (C-5 o. C-6); 130.7, 130.7, 130.8 (C-17/18); 133.0, 133.6 (C-5 o. C-6); 154.2, 154.4 (C-26); 168.2, 168.4 (C-8); 170.4, 170.4 (C-24); 171.7, 171.9 (C-12); 172.2 (C-20).

HR/MS (ESI): calculated for: $[M+H]^+$ 571.3126; found: 571.3130; calculated for $[M+Na]^+$ 593.2946; found: 593.2943.

Synthesis of Fmoc-[L-2Cl-F]-[ProM-2]-[R,S,R-Gly-ProM-15]-OMe (250)

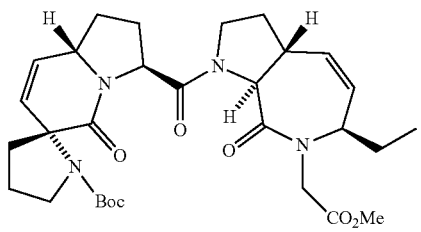

1.) TFA, DCM
2.) $Na_2CO_3$ (s), DCM
3.) Fmoc-[L-2Cl—F]—OH (245)
   HATU (182), DIPEA
   $Na_2CO_3$ (s),
   0° C. → RT

248

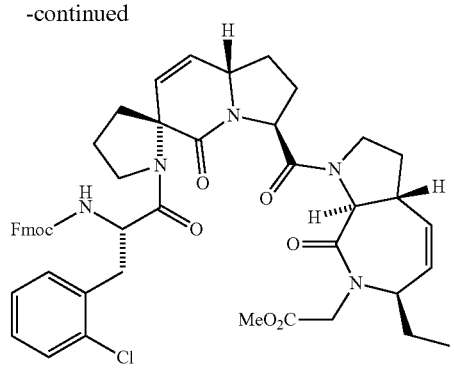

250

1.) Synthesis of the active ester: Under an argon atmosphere, a solution of 318 mg (0.753 mmol, 2 eq.) Fmoc-[L-2Cl-F]-OH (245) and 358 mg (0.942 mmol, 2.5 eq.) HATU in 4.7 ml abs. DCM at rt was treated with 0.13 ml (0.753 mmol, 2 eq.) DIPEA and the mixture was stirred for 45 min (cloudy, slightly yellowish solution).

2.) Synthesis of the ligand 250:215 mg (0.377 mmol, 1 eq.) of the tetrapeptide 248 were dissolved in 0.87 ml of DCM under non-inert conditions and 0.44 ml (5.65 mmol, 15 eq.) of TFA were added dropwise at 0° C. The ice bath was removed and the mixture was stirred at rt for 1 h, then all volatile constituents were removed under reduced pressure, concentrated twice from DCM and finally dried in vacuo. The residue obtained was taken up in 5 ml of DCM, 3 spatulas of solid $Na_2CO_3$ were added (solid material stuck together somewhat) and the mixture was stirred for 5 minutes. It was then filtered, the brownish filter cake was washed with a little $CH_3CN$ (brown discoloration dissolves), the solvent was removed under reduced pressure and dried in vacuo. The residue now obtained was taken up in 4.7 ml of abs DCM under an argon atmosphere and a few drops of dry $CH_3CN$ were added (just enough for the polar solid to dissolve). Then 3 spatulas of solid $Na_2CO_3$ and then the solution of the previously synthesized active ester (see above) were added.

After stirring overnight at rt, the $Na_2CO_3$ was filtered off over a little silica (eluent: DCM/MeOH=15/1), the solvent was removed under reduced pressure and the residue was purified by column chromatography on silica gel (DCM/MeOH=15/1). After drying in vacuo, 486 mg (150%) of a slightly brownish solid could be isolated.

It was not possible at this point to completely purify the desired product 250. Both the urea species (Rt=0.35, silica, DCM/MeOH=15/1, $KMnO_4$) and traces of DIPEA (Rt=0.22, silica, DCM/MeOH-15/1, $KMnO_4$) could not be separated by column chromatography. However, since these impurities had no influence on the subsequent chemical reactions, no product fractions contaminated with them were discarded in order to avoid yield losses. The 1H-NMR spectrum of the brownish solid showed the expected characteristic signals of the ligand 250, as well as the signals of the impurities mentioned. For this reason, a complete characterization and determination of the yield has not been carried out here. A quantitative reaction was assumed for the next step.

$C_{49}H_{52}ClN_5O_8$, M: 874.42 g/mol.

TLC: Rt=0.29 (silica, DCM/MeOH=15/1), $KMnO_4$ reagent.

HR/MS (ESI): calculated for: $[M+H]^+$874.3577; found: 874.3591; calculated for $[M+Na]^+$896.3397; found: 896.3403.

Synthesis of Ac-[L-2Cl-F]-[ProM-2]-[R,S,R-Gly-ProM-15]-OMe (247)

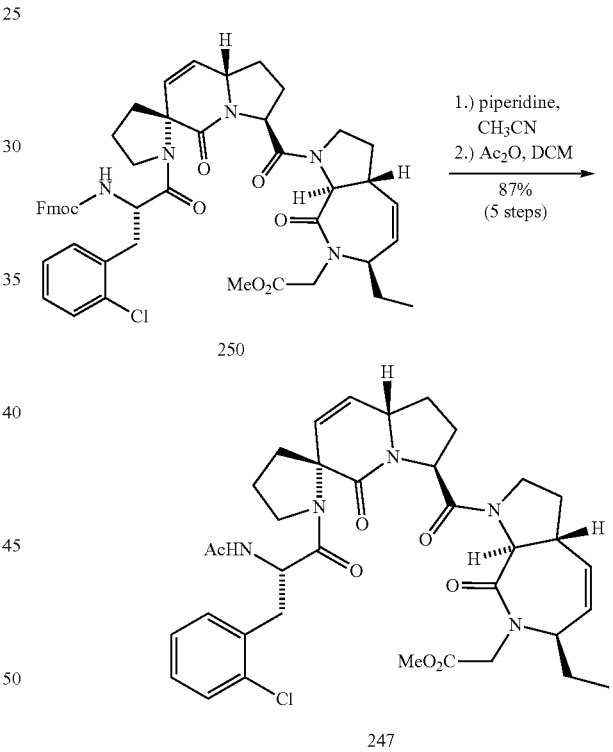

247

The previously synthesized ligand 250 (6.19.2) was dissolved in 6.8 ml of dry $CH_3CN$ under an argon atmosphere and 1.7 ml of piperidine were added dropwise at rt (corresponds to 20% piperidine in $CH_3CN$).

After stirring for 1 h at rt, the solvent was changed on the Schlenk line: First, $CH_3CN$ and piperidine were carefully removed and evaporated to dryness. The residue was then taken up in ~ 2 ml of DCM, freed again from solvent and piperidine residues and this procedure was repeated one more time. The residue was then taken up in 15.3 ml of abs. DCM under an argon atmosphere and treated dropwise with 1.7 ml acetic anhydride at rt (corresponds to 10% AC2O in DCM). After stirring overnight, all volatile constituents were removed under reduced pressure, concentrated again from DCM and the crude product was subsequently purified by column chromatography on silica gel (DCM/MeOH=15/1). After drying in vacuo, 227 mg (0.327 mmol, 87% over 5 steps) of the desired ligand 247 could be isolated as a slightly brownish solid.

$C_{36}H_{44}ClN_5O_7$, M: 694.22 g/mol.

TLC: Rt=0.17 (silica, DCM/MeOH=15/1), KMnO$_4$ reagent.

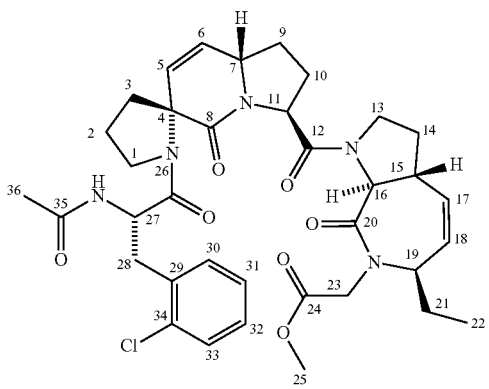

$^1$H-NMR (600 MHZ, CDCl$_3$, rotamer mixture 98): δ [ppm]=0.98-1.02 (m, 3H, H-22); 1.54-1.62 (m, 1H, H-21); 1.68-2.22 (m, 12H, H-2/3/9/10/14/21'/36); 2.29 (ψ dt, J=12.2 Hz, J=5.9 Hz, 0.3H, H-3'rot2); 2.38 (ψ dt, J=12.9 Hz, J=6.4 Hz, 0.7H, H-3'rot1); 2.45-2.50 (m, 0.7H, H-10'rot1); 2.53-2.58 (m, 0.3H, H-10'rot2); 2.85 (dd, $^2$J=14.2 Hz, $^3$J=10.7 Hz, 0.7H, H-28rot1); 2.92-3.03 (m, 1.3H, H-15/28rot2); 3.14 (dd, $^2$J=13.0 Hz, $^3$J=6.1 Hz, 0.3H, H-28'rot2); 3.36 (dd, $^2$J=14.2 Hz, $^3$J=3.8 Hz, 0.7H, H-28'rot1); 3.44-3.48 (m, 0.3H, H-1 rot2); 3.54-3.61 (m, 1H, H-13); 3.67, 3.67 (2× s, 3H, H-25); 3.76-3.80 (m, 1H, H-23); 3.89-3.96 (m, 1.7H, H-1rot1/1'); 4.10 (ψ t, J=9.0 Hz, 0.3H, H-13'rot2); 4.19 (ψ t, J=8.8 Hz, 0.7H, H-13'rot1); 4.32-4.36 (m, 0.3H, H-7rot2); 4.38-4.41 (m, 0.7H, H-7rot1); 4.67-4.76 (m, 2.6H, H-5rot2 0.6rot2/19/23'/27rot2); 4.83 (ψ t, J=8.3 Hz, 0.3H, H-11rot2); 4.96 (ψ t, J=8.1 Hz, 0.7H, H-11rot1); 5.06 (d, $^3$J=12.1 Hz, 0.3H, H-16rot2); 5.11-5.17 (m, 1.4H, H-16rot1/27rot1); 5.54-5.89 (m, 3.7H, H-5rot1/6 o. H-5/6rot1 und H-17/18); 6.13 (d, $^3$J=10.3 Hz, 0.3H, NHrot2); 6.17 (d, $^3$J=8.8 Hz, 0.7H, NHrot1); 7.13-7.34 (m, 4H, H-30/31/32/33).

$^{13}$C-NMR (150 MHz, CDCl$_3$, rotamer mixture 98): δ [ppm]=11.7, 11.7 (C-22); 22.2, 24.1 (C-2); 23.0, 23.0 (C-36); 26.2 (C-21); 28.2, 28.5 (C-10); 31.0, 31.0, 31.2, 31.4 (C-9/14); 36.0, 37.9 (C-28); 38.2, 41.1 (C-3); 42.3, 42.3 (C-15); 43.2 (C-23); 47.5 (C-13); 48.7, 48.8 (C-1); 50.5, 50.7 (C-27); 52.1 (C-25); 55.4, 55.6 (C-19); 56.4, 57.0 (C-11); 59.2, 59.6 (C-7); 60.2, 60.3 (C-16); 64.7, 65.5 (C-4); 123.1, 125.6 (C-5 o. C-6); 126.6, 126.8, 128.6, 128.6, 129.4, 129.6 (C-31/32/33); 130.0, 130.6, 130.8, 130.8, 131.3 (C-5 o. C-6/17/18); 131.8, 132.0 (C-30); 134.4, 134.6, 134.7, 135.4 (C-29/34); 166.7, 167.1 (C-8); 169.7, 170.2, 170.4, 171.3, 171.7 (C-12/24/26/35); 172.1, 172.2 (C-20).

HR/MS (ESI): calculated for: [M+H]$^+$694.3002; found: 694.3014; calculated for [M+Na]$^+$716.2821; found: 716.2824.

Further Synthesis of the Ligands According to the Invention

In the course of this work, an improved methodology for assembling the ProM building blocks was developed, which not only requires fewer steps, but above all delivers the products in higher yield and purity. The novel, improved ligand synthesis differs from previous methods in that the substances are aligned or produced from "left to right". First N-Fmoc-protected (L)-2-chlorophenylalanine is linked with the "first" (central) ProM building block, then, after ester hydrolysis, the "right" (C-terminal) ProM building block is attached. Finally, the Fmoc group is exchanged for the acetyl group (or also for other acyl residues).

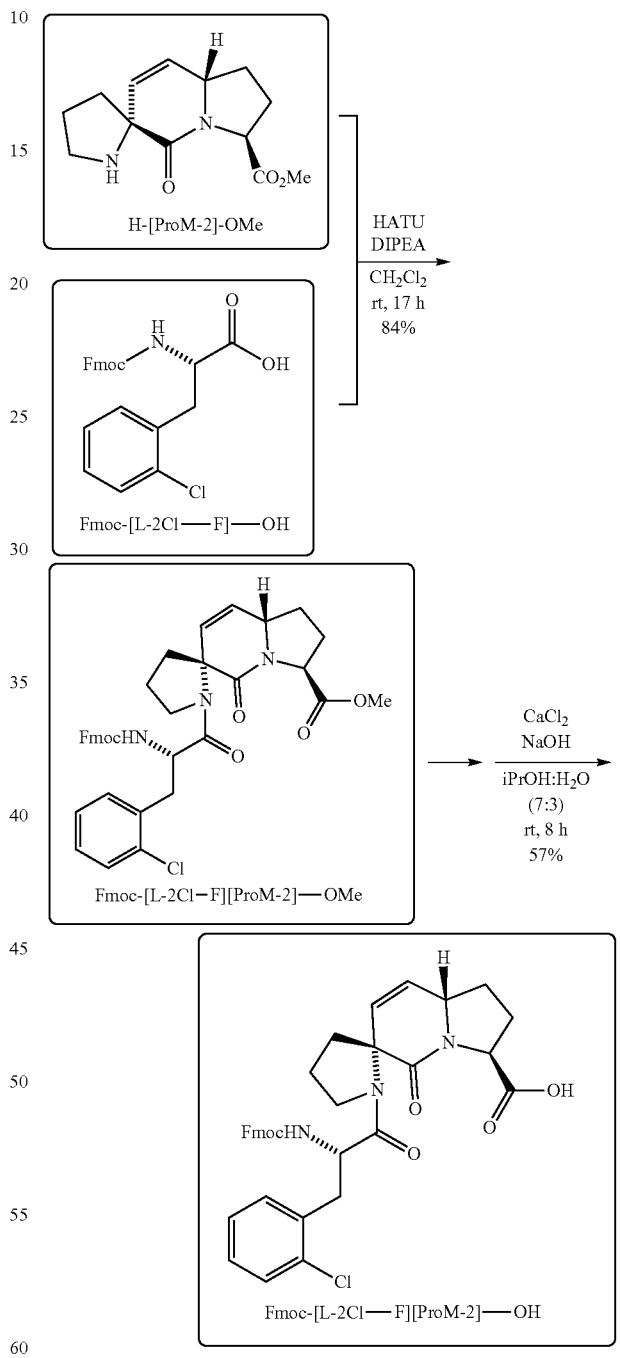

-continued
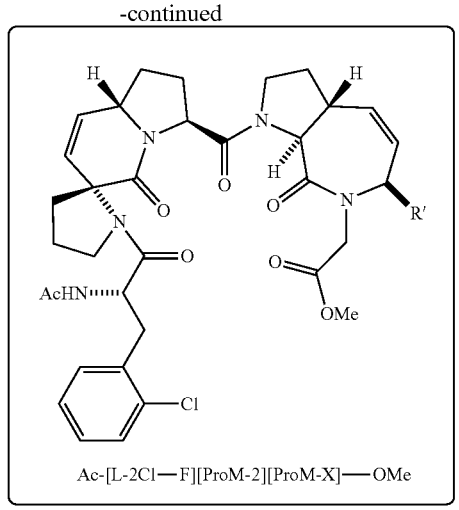
Ac-[L-2Cl—F][ProM-2][ProM-X]—OMe
for R' = nPr: 39% over three steps
for R' = iBu; 47% over three steps
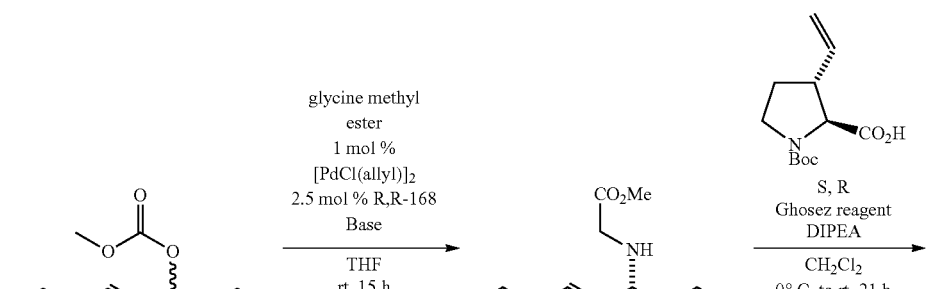
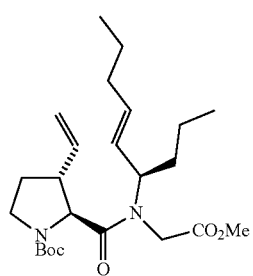
S,R,R
Hoveyda II
toluene
70° C., 25 h
42%

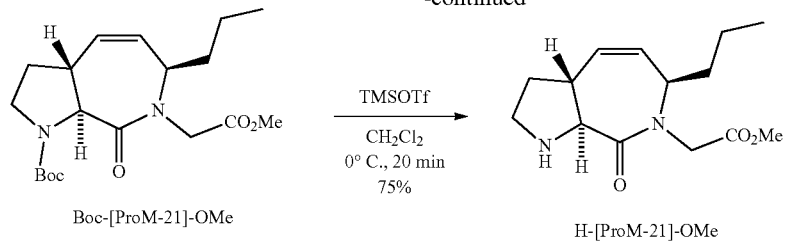

Characteristic data of H-[ProM-17]-OMe

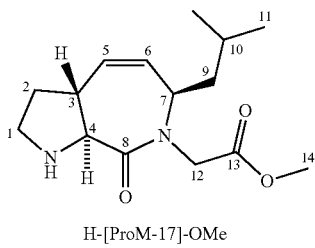 [SMILES: COC(=O)CN1C(=O)[C@H]2NCC[C@@H]2C=C[C@H]1CC(C)C]

H-[ProM-17]-OMe $C_{15}H_{24}N_2O_3$.

280.368 g/mol.

TLC: ($SiO_2$, $CH_2Cl_2$/MeOH 20:1): $R_f$=0.13.

$^1$H-NMR: (500 MHZ, $CDCl_3$) δ=5.90 (dt, $^3J$=11.1, 4J=2.4 Hz, 1H, H5), 5.49 (dt, $^3J$=11.1, 4J=3.0 Hz, 1H, H6), 4.75-4.70 (m, 1H, H7), 4.46 (d, $^3J$=11.9 Hz, 1H, H4), 4.41 (d, $^3J$=17.5 Hz, 1H, H12a), 3.99 (d, $^3J$=17.6 Hz, 1H, H12b) 3.71 (s, 3H, H14), 3.22 (dd, $^3J$=9.5, 3J=4.7 Hz, 2H, H1), 3.11 (bs, 1H,-NH), 2.62-2.55 (m, 1H, H3), 2.23-2.18 (m, 1H, H2a), 1.81-1.72 (m, 1H, H2b), 1.63 (dp, $^3J$=13.2, 3J=6.5 Hz, 1H, H10), 1.55-1.42 (m, 2H, H9), 0.96 (Wdd, $^3J$=15.8, 3J=6.5 Hz, 6H, H11).

$^{13}$C-NMR: (125 MHz, $CDCl_3$) δ=174.3 (s, C8), 170.3 (s, C13), 131.9 (d, C5), 130.3 (d, C6), 62.1 (d, C4), 52.3 (q, C14), 51.7 (d, C7), 45.4 (d, C3), 45.2 (t, C1), 43.7 (t, C12), 42.1 (t, C9), 32.5 (t, C2), 25.1 (d, C10), 23.2 (q, C11a), 21.8 (q, C11b).

FT-IR: (ATR) ν [cm 1]=3371 (b), 2954 (m), 2871 (w), 1751 (m), 1657 (s), 1455 (m), 1436 (m), 1384 (m), 1302 (w), 1260 (m), 1201 (s), 1177 (s), 1125 (m), 1076 (w), 1042 (w), 1008 (m), 938 (w), 913 (w), 823 (w), 775 (m), 734 (w), 690 (m), 635 (m), 561 (m).

GC-MS: m/z (%)=280 (12), 251 (5), 223 (17), 195 (44), 179 (5), 158 (100), 137 (5), 122 (44), 106 (24), 91 (19), 69 (29), 41 (26).

HR-MS (ESI):

| exact mass [u] | measured mass [u] | error [ppm] |
|---|---|---|
| 281.1859 [M + H]$^+$ | 281.1859 [M + H]$^+$ | +0.06 |
| 303.1679 [M + Na]$^+$ | 303.1678 [M + Na]$^+$ | −0.23 |

$[α]_λ^{20}$: (0.50 g/100 ml in $CHCl_3$): $[α]_{365}$=−278.6°, $[α]_{436}$=−175.6°, $[α]_{546}$=−103.5°, $[α]_{579}$=−90.8°, $[α]_{589}$=−88.1°.

Characteristic Data of H-[ProM-21]-OMe

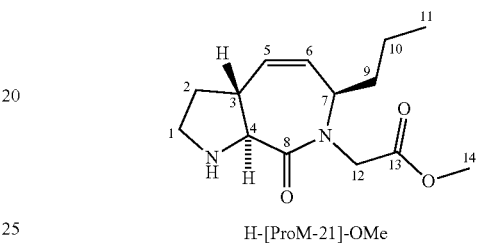

H-[ProM-21]-OMe $C_{14}H_{22}N_2O_3$.

266.341 g/mol.

TLC: ($SiO_2$, CyHex/EtOAc/MeOH 2:2:1): R+=0.10.

$^1$H-NMR: (600 MHZ, $CDCl_3$) δ=5.90 (dt, $^3J$=11.1 Hz, 4J=2.4 Hz, 1H, H5), 5.52 (dt, $^3J$=11.1 Hz, 4J=3.0 Hz, 1H, H6), 4.65-4.62 (m, 1H, H7), 4.44-4.35 (m, 2H, H4 und H12a), 4.04 (d, $^3J$=17.6 Hz, 1H, H12b), 3.71 (s, 3H, H14), 3.23-3.17 (m, 2H, H1), 2.60-2.54 (m, 1H, H3), 2.22-2.17 (m, 1H, H2a), 1.75 (tt, $^3J$=12.3 Hz, $^3J$=9.5 Hz, 1H, H2b), 1.70-1.50 (m, 2H, H9), 1.50-1.30 (m, 2H, H10), 0.98 (t, $^3J$=7.3 Hz, 3H, H11).

$^{13}$C-NMR: (125 MHZ, $CDCl_3$) δ=174.4 (s, C8), 170.4 (s, C13), 132.0 (d, C5), 130.1 (d, C6), 62.1 (d, C4), 53.8 (d, C7), 52.3 (q, C14), 45.4 (d, C3), 45.1 (t, C1), 43.7 (t, C12), 35.2 (t, C9), 32.6 (t, C2), 20.3 (t, C10), 13.9 (q, C11).

FT-IR: (ATR) ν [cm 1]=3321 (b), 3020 (w), 2956 (w), 2873 (w), 1751 (m), 1651 (s), 1454 (m), 1436 (m), 1384 (m), 1301 (w), 1253 (m), 1202 (s), 1178 (s), 1163 (s), 1114 (m), 1078 (w), 1047 (w), 1009 (m), 943 (w), 909 (w), 890 (w), 845 (w), 783 (m), 732 (m), 689 (m), 638 (m), 558 (m), 485 (m).

GC-MS: m/z (%)=266 (27), 237 (16), 223 (49), 209 (10), 195 (53), 179 (5), 165 (10), 144 (100), 122 (31), 108 (26), 94 (15), 80 (24), 56 (6), 41 (11).

HR-MS (ESI):

| exact mass [u] | measured mass [u] | error [ppm] |
|---|---|---|
| 267.1703 [M + H]$^+$ | 267.1704 [M + H]$^+$ | +0.24 |
| 289.1522 [M + Na]$^+$ | 289.1523 [M + Na]$^+$ | +0.20 |

Characteristic data of Ac-[I-2Cl-F] [ProM-1] [ProM-15]-OMe

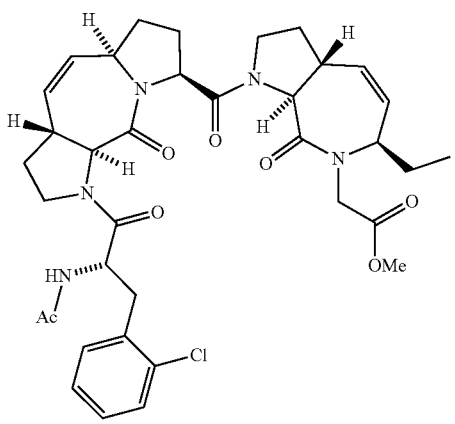

Ac-[L-2Cl-F][ProM-1][ProM-15]-OMe $C_{36}H_{44}N_5O_7Cl_1$.
694.226 g/mol.
$^{13}$C-NMR: (125 MHZ, CDCl$_3$) δ=172.2, 171.2, 171.0, 170.9, 170.8, 170.5, 170.5, 169.6, 168.8, 168.7, 135.2, 134.8, 134.7, 134.6, 132.2, 132.0, 130.8, 130.7, 130.6, 130.0, 129.5, 129.5, 129.7, 128.8, 128.6, 128.0, 127.9, 126.9, 126.8, 62.8, 62.3, 60.3, 60.2, 59.1, 59.0, 58.0, 55.5, 55.4, 52.1, 51.6, 50.5, 47.9, 47.7, 46.9, 43.2, 42.4, 42.0, 40.6, 38.6, 37.0, 33.4, 33.2, 31.8, 31.1, 29.9, 27.3, 26.2, 23.5, 23.2, 22.8, 14.3, 11.8, 11.8.
HR-MS (ESI):

| exact mass [u] | measured mass [u] | error [ppm] |
|---|---|---|
| 694.3002 [M + H]⁺ | 694.3012 [M + H]⁺ | +1.46 |
| 716.2821 [M + Na]⁺ | 716.2823 [M + Na]⁺ | +0.33 |

Characteristic data of Ac-[I-2Cl-F] [ProM-1] [ProM-17]-OMe

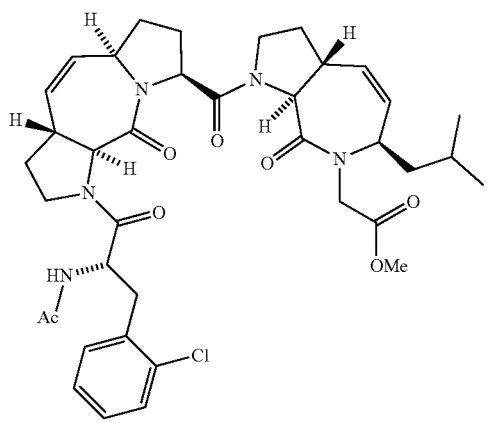

Ac-[L-2Cl-F][ProM-1][ProM-17]-OMe $C_{36}H_{48}N_5O_7Cl_1$.
722.280 g/mol.
13C-NMR: (125 MHz, CDCl$_3$) δ=172.3, 171.1, 171.0, 170.9, 170.7, 170.0, 168.9, 168.9, 134.7, 134.6, 134.5, 132.2, 132.1, 130.9, 130.8, 130.7, 130.6, 129.9, 129.5, 129.5, 129.2, 128.9, 128.6, 128.1, 128.1, 127.0, 126.9, 62.8, 62.3, 60.3, 59.2, 58.1, 52.2, 51.6, 50.7, 48.0, 47.7, 47.0, 46.1, 43.3, 42.4, 42.2, 40.6, 38.6, 36.8, 33.4, 33.2, 32.1, 31.8, 31.1, 31.0, 29.9, 27.25, 25.1, 23.6, 23.1, 22.7, 22.1, 21.7, 14.3.
HR-MS (ESI):

| exact mass [u] | measured mass [u] | error [ppm] |
|---|---|---|
| 722.3315 [M + H]⁺ | 722.3319 [M + H]⁺ | +0.53 |
| 744.3134 [M + Na]⁺ | 744.3132 [M + Na]⁺ | −0.26 |

Characteristic data of Ac-[I-2Cl-F] [ProM-2] [ProM-17]-OMe

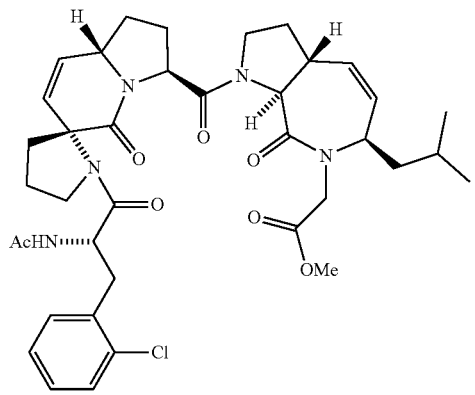

Ac-[L-2Cl-F][ProM-2][ProM-17]-OMe $C_{38}H_{48}N_5O_7Cl_1$
722.280 g/mol.
$^{13}$C-NMR: (125 MHz, CDCl$_3$) δ=172.3, 172.2, 171.6, 171.6, 171.1, 170.5, 170.46, 170.2, 169.4, 168.2, 167.2, 166.7, 135.4, 134.9, 134.7, 134.6, 132.2, 132.1, 131.8, 131.5, 131.0, 130.9, 130.7, 130.1, 129.6, 129.4, 128.5, 126.8, 126.6, 125.5, 123.1, 77.4, 77.0, 65.5, 64.6, 60.3, 60.2, 59.6, 59.2, 57.1, 56.4, 52.2, 52.1, 51.5, 51.5, 50.6, 50.4, 48.7, 47.5, 43.3, 42.4, 42.4, 42.2, 41.2, 38.3, 38.0, 36.2, 31.5, 31.0, 29.8, 28.2, 25.1, 24.1, 23.4, 23.3, 23.2, 22.8, 22.2, 21.9, 21.9, 14.3.
HR-MS (ESI):

| exact mass [u] | measured mass [u] | error [ppm] |
|---|---|---|
| 722.3315 [M + H]⁺ | 722.3320 [M + H]⁺ | +0.75 |
| 744.3134 [M + Na]⁺ | 744.3132 [M + Na]⁺ | −0.28 |

Characteristic data of Ac-[I-2CI-F] [ProM-1] [ProM-21]-OMe

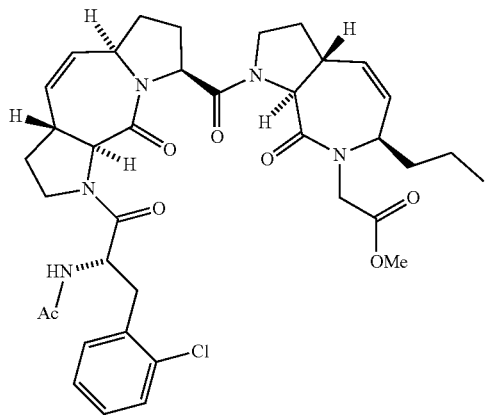

Ac-[L-2Cl-F][ProM-1][ProM-21]-OMe $C_{37}H_{46}N_5O_7Cl_1$.
708.253 g/mol.
$^{13}$C-NMR: (125 MHz, CDCl$_3$) δ=172.2, 171.1, 171.0, 170.9, 170.5, 170.5, 169.6, 168.8, 168.7, 168.7, 135.1, 134.8, 134.7, 134.6, 132.2, 132.0, 130.9, 130.8, 130.8, 130.7, 130.0, 129.5, 129.5, 129.2, 128.8, 128.6, 128.0, 127.9, 126.9, 126.8, 77.4, 62.8, 62.3, 60.2, 59.1, 59.0, 59.0, 58.1, 58.0, 53.6, 52.1, 52.1, 51.6, 50.5, 47.9, 47.7, 46.9, 43.3, 42.4, 42.0, 40.6, 37.0, 35.4, 33.3, 33.2, 31.8, 31.1, 31.0, 29.9, 27.3, 23.5, 23.2, 23.1, 20.4, 14.0.
HR-MS (ESI):

| exact mass [u] | measured mass [u] | error [ppm] |
|---|---|---|
| 708.3158 [M + H]$^+$ | 708.3165 [M + H]$^+$ | +0.95 |
| 730.2978 [M + Na]$^+$ | 730.2972 [M + Na]$^+$ | −0.75 |

Characteristic data of Ac-[I-2CI-F] [ProM-2] [ProM-21]-OMe

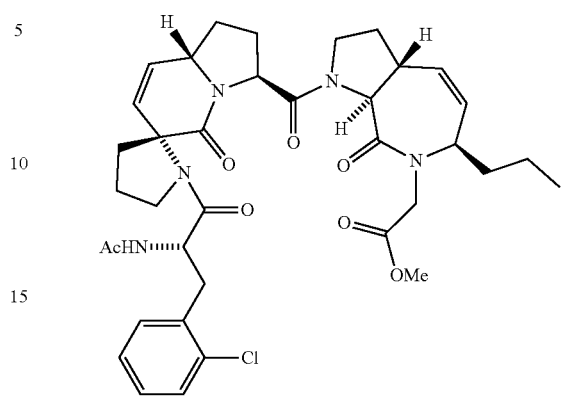

Ac-[L-2Cl-F][ProM-2][ProM-21]-OMe $C_{37}H_{46}N_5O_7Cl_1$.
708.253 g/mol.
$^{13}$C-NMR: (125 MHZ, CDCl$_3$) δ=172.2, 172.1, 171.7, 171.5, 171.3, 171.1, 170.4, 170.2, 169.3, 167.1, 166.6, 135.4, 134.9, 134.6, 134.5, 132.0, 131.8, 131.5, 131.1, 130.6, 130.1, 129.5, 129.4, 128.5, 126.7, 126.5, 125.5, 123.0, 77.4, 77.2, 76.9, 65.5, 64.6, 60.3, 60.2, 59.6, 59.2, 57.0, 56.4, 56.3, 53.7, 53.6, 52.9, 52.2, 52.1, 50.6, 50.3, 48.7, 48.7, 47.5, 43.2, 43.1, 42.3, 41.5, 41.2, 38.5, 38.3, 38.0, 36.2, 35.3, 32.1, 31.4, 31.2, 31.1, 29.8, 28.6, 28.2, 24.1, 23.3, 23.2, 22.8, 22.2, 20.3, 19.8, 14.0, 14.0.
HR-MS (ESI):

| exact mass [u] | measured mass [u] | error [ppm] |
|---|---|---|
| 708.3158 [M + H]$^+$ | 708.3162 [M + H]$^+$ | +0.56 |
| 730.2978 [M + Na]$^+$ | 730.2974 [M + Na]$^+$ | −0.44 |

The invention claimed is:

1. A compound according to formula I:

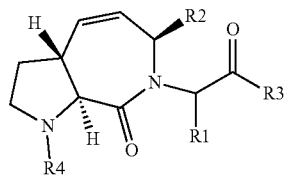

wherein

R1 is H or a side chain selected from the group consisting of alkyl, aryl, heteroaryl, cycloalkyl, hydroxyalkyl, arylalkyl, alkylheteroaryl, aminoalkyl, aminocarbonyl, alkylaminocarbonyl, alkylcarbonyl, mercaptoalkyl, sulfidoalkyl, and a side chain of an amino acid, the side chains mentioned being optionally substituted, R2 is alkyl, aryl, alkoxyalkyl, cycloalkyl, mercaptoalkyl, sulfidoalkyl, arylalkyl, or fluoroalkyl, R3 is OH or a side chain selected from the group consisting of alkyl; O-alkyl; O-aryl; NRR', wherein R, R' are H or alkyl; and NROR', wherein R, R' are H, alkyl, or heteroaryl, R4 is H or a side chain selected from the group consisting of alkyl, acyl, aryl, heteroaryl, cycloalkyl, alkylheteroaryl, alkylcarbonyl, arylalkyl, arylcarbonyl, alkoxycarbonyl, aminocarbonyl, aryloxycarbonyl, alkylsulfonyl, arylsulfonyl, aminoacyl, and peptidyl, the side chains mentioned being optionally substituted, R5 is:

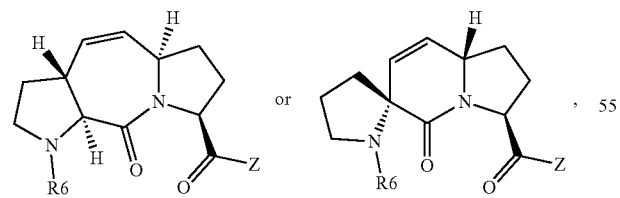

Z is a bond to the structure according to formula I,

R6 is H or a side chain selected from the group consisting of alkyl, aryl, cycloalkyl, alkylcarbonyl, arylcarbonyl, alkoxycarbonyl, arylalkyl, aminocarbonyl, aryloxycarbonyl, alkylsulfonyl, arylsulfonyl, aminoacyl, and peptidyl, the side chains mentioned being optionally substituted, or

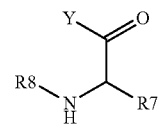

Y is a bond to the structure according to R5,

R7 is H or a side chain selected from the group consisting of alkyl, aryl, heteroaryl, cycloalkyl, hydroxyalkyl, arylalkyl, alkylheteroaryl, aminoalkyl, aminocarbonyl, alkylaminocarbonyl, alkylcarbonyl, mercaptoalkyl, sulfidoalkyl, and a side chain of an amino acid, the side chains mentioned being optionally substituted, and R8 is H or a side chain selected from the group consisting of alkyl, aryl, acyl, heteroaryl, cycloalkyl, alkylheteroaryl, alkylcarbonyl, arylalkyl, arylcarbonyl, alkoxycarbonyl, aminocarbonyl, aryloxycarbonyl, alkylsulfonyl, arylsulfonyl, aminoacyl, and peptidyl, the side chains mentioned being optionally substituted.

2. The compound of to claim 1, according to formula II-a or formula II-b:

Formula II-a

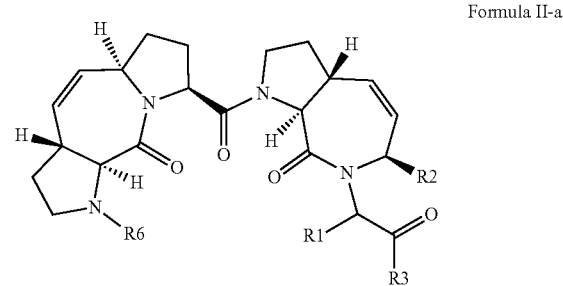

Formula II-b

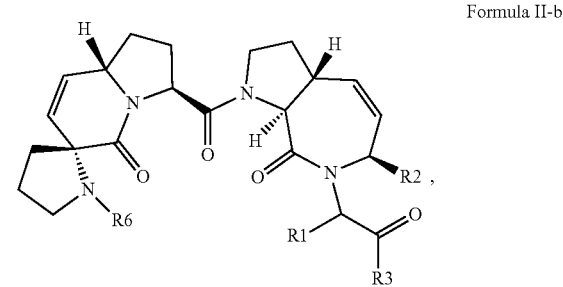

wherein;

R1 is H or a side chain selected from the group consisting of alkyl, aryl, heteroaryl, cycloalkyl, hydroxyalkyl, arylalkyl, alkylheteroaryl, aminoalkyl, aminocarbonyl, alkylaminocarbonyl, alkylcarbonyl, mercaptoalkyl, sulfidoalkyl, and a side chain of an amino acid, the side chains mentioned being optionally substituted, R2 is alkyl, aryl, alkoxyalkyl, cycloalkyl, mercaptoalkyl, sulfidoalkyl, arylalkyl, or fluoroalkyl, R3 is OH or a side chain selected from the group consisting of alkyl; O-alkyl; O-aryl; NRR', wherein R, R': H or alkyl; and NROR', wherein R, R': H, alkyl, or heteroaryl, R6 is H or a side chain selected from the group consisting of alkyl, aryl, cycloalkyl, alkylcarbonyl, arylcarbonyl, alkoxycarbonyl, arylalkyl, aminocarbonyl, aryloxycarbonyl, alkylsulfonyl, arylsulfonyl, aminoacyl and peptidyl, the side chains mentioned being optionally substituted, or

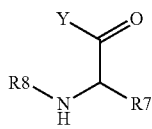

Y is a bond to the structure according to formula II-a or II-b,

R7 is H or a side chain selected from the group consisting of alkyl, aryl, heteroaryl, cycloalkyl, hydroxyalkyl, arylalkyl, alkylheteroaryl, aminoalkyl, aminocarbonyl, alkylaminocarbonyl, alkylcarbonyl, mercaptoalkyl, sulfidoalkyl, and a side chain of an amino acid, the side chains mentioned being optionally substituted, and R8 is H or a side chain selected from the group consisting of alkyl, aryl, acyl, heteroaryl, cycloalkyl, alkyl-heteroaryl, alkylcarbonyl, arylalkyl, arylcarbonyl, alkoxycarbonyl, aminocarbonyl, aryloxycarbonyl, alkylsulfonyl, arylsulfonyl, aminoacyl and or peptidyl, the side chains residues mentioned being optionally substituted.

3. The compound according to claim 1, wherein:
R1 is a side chain of an amino acid which is derived from a natural (canonical) or unnatural D- or L-configured amino acid.

4. The compound according to claim 3, wherein:
R2 is CH$_2$OMe, CH$_2$SMe, CH$_2$CH$_2$OR, CH$_2$CH$_2$SR, wherein R: C1-C4 alkyl or H, benzyl, CH$_2$-benzyl or CH$_2$CH$_2$-benzyl, or
R2 is C1-C4 alkyl,
or
R2 is methyl, propyl, iso-propyl, butyl, iso-butyl, or sec-butyl.

5. The compound according to claim 1, wherein when R3 is OH, and wherein the compound is present as a salt.

6. The compound according to claim 1, wherein R4 and R6 can be the same or different, wherein R4 and R6 are H or a side chain selected from the group consisting of alkyl, aryl, acyl, peptidyl, alkylsulfonyl, of arylsulfonyl, and heteroaryl, wherein the side chains residues mentioned being optionally substituted.

7. The compound according to claim 2, wherein:
R6 is:

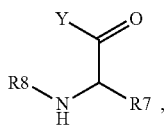

Y is a bond to the structure according to formula II-a or II-b,

R7 is H or a side chain selected from the group consisting of alkyl, aryl, heteroaryl, cycloalkyl, hydroxyalkyl, arylalkyl, alkylheteroaryl, aminoalkyl, aminocarbonyl, alkylaminocarbonyl, alkylcarbonyl, mercaptoalkyl, sulfidoalkyl, and a side chain of an amino acid, the side chains mentioned being optionally substituted, and R8 is H or a side chain selected from the group consisting of alkyl, aryl, acyl, peptidyl, alkylsulfonyl, arylsulfonyl, and heteroaryl, the side chains mentioned being optionally substituted.

8. The compound according to claim 2, wherein:
R7 is CH$_2$-aryl, the substituent being positioned at the ortho position of the phenyl group.

9. The compound according to claim 2, wherein R6 is N-acyl-(2-chlorophenyl) alaninoyl.

10. The compound according to claim 1, wherein optionally substituted means that one or more hydrogen atoms of the hydrocarbon group are replaced by one or more substituents selected from the group consisting of halogen, —OH, —CN, —SH, amine, —NO$_2$, and -alkyl, wherein alkyl is optionally substituted by one or more substituents.

11. The compound according to claim 1, according to formula III:

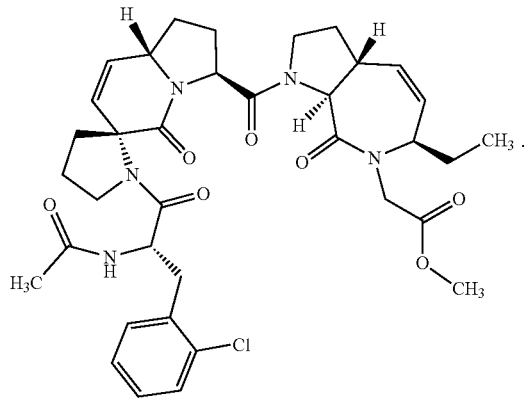 [SMILES: CC[C@@H]1C=C[C@H]2CCN(C(=O)[C@@H]3CC[C@H]4C=C[C@]5(CCCN5C(=O)[C@H](Cc5ccccc5Cl)NC(C)=O)C(=O)N43)[C@@H]2C(=O)N1CC(=O)OC]

12. A method for inhibiting an Ena/VASP-EVH1-mediated protein-protein interaction in a cell or a subject in need thereof, comprising administering to the cell or a subject in need a compound according to claim 1.

13. A pharmaceutical composition comprising a compound according to claim 1, further comprising a pharmaceutically acceptable carrier.

14. A method for treating a tumor, comprising administering a compound according to claim 1 to a subject in need thereof.

15. The method of claim 14, comprising inhibiting chemotaxis and/or motility of tumor cells based on disrupting actin filament synthesis.

16. The method according to claim 12, wherein the compound has a dissociation constant (K$_d$) in complex with an Ena/VASP-EVH1 domain of ≤5 μM.

17. The method of claim 14, wherein the tumor is breast cancer.

18. The method of claim 14, wherein the tumor is a metastatic tumor.

19. The compound according to claim 4, wherein the C1-C4 alkyl in the R2 position is methyl, ethyl, propyl, iso-propyl, butyl, iso-butyl, or sec-butyl.

20. The compound according to claim 10, wherein the alkyl has 1, 2, 3 or 4 substituents.

\* \* \* \* \*